US008426332B2

(12) United States Patent
Yilmaz et al.

(10) Patent No.: US 8,426,332 B2
(45) Date of Patent: Apr. 23, 2013

(54) METAL-BRIDGED PILLARED SILICATE COMPOUNDS AND PROCESS FOR THEIR PRODUCTION

(75) Inventors: Bilge Yilmaz, Union, NJ (US); Ulrich Müller, Neustadt (DE); Trees De Baerdemaeker, Merchtem (BE); Hermann Gies, Sprockhövel (DE); Feng-Shou Xiao, Changchun (CN); Takashi Tatsumi, Kawasaki (JP); Xinhe Bao, Dalian (CN); Weiping Zhang, Dalian (CN); Dirk de Vos, Holsbeek (BE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/175,125

(22) Filed: Jul. 1, 2011

(65) Prior Publication Data

US 2012/0004332 A1 Jan. 5, 2012

Related U.S. Application Data

(63) Continuation of application No. PCT/CN2010/074920, filed on Jul. 2, 2010.

(51) Int. Cl.
*B01J 29/04* (2006.01)

(52) U.S. Cl.
USPC .......... 502/60

(58) Field of Classification Search .......... 502/60
See application file for complete search history.

(56) References Cited

U.S. PATENT DOCUMENTS

| | | | |
|---|---|---|---|
| 4,176,090 A | 11/1979 | Lussier et al. | |
| 4,968,652 A | 11/1990 | Johnson et al. | |
| 6,475,944 B1 * | 11/2002 | Yang et al. | 502/84 |
| 6,703,501 B1 | 3/2004 | Kim et al. | |
| 7,947,244 B2 | 5/2011 | Mueller et al. | |
| 2006/0094594 A1 | 5/2006 | Koch et al. | |
| 2010/0119442 A1 | 5/2010 | Mueller et al. | |
| 2011/0135567 A1 | 6/2011 | Muller et al. | |

FOREIGN PATENT DOCUMENTS

| | | |
|---|---|---|
| WO | WO-2005/100242 | 10/2005 |
| WO | WO-2007/042531 | 4/2007 |
| WO | WO-2008/122579 | 10/2008 |

OTHER PUBLICATIONS

Dorset, Douglas L. et al., “Crystal Structure of MCM-65: An Alternative Linkage of Ferrierite Layers”, *J. Phys. Chem. B 2004, 108* 2004 , 15216-15222.

Ikeda, T. et al., “Preparation and Crystal Structure of RUB-18 Modified for Synthesis of Zeolite RWR by Topotactic Conversion”, *Microporous and Mesoporous Materials 110* 2008 , 488-500.

Kruger, H. et al., “Vermischen im Hochzahen, Plastischen, Pastosen und Teigigen Zustand”, *Ullmanns Encyklopadie der Technischen Chemie, 4th Edition*, vol. 2 1972 , 20 pages.

Latzel, S. et al., “Synthesis and General Characterisation of RUB-22: A New Microporous Silicate Possessing and Interrupted Framework Structure”, *From Zeolites to Porus MOF Materials—The 40th Anniversary of International Zeolite Conference*, vol. 170 Aug. 17, 2007 , 9 pgs.

Li, Zhaofei et al., “A New Layer Silicate with Structural Motives of Silicate Zeolites: Synthesis, Crystals Structure, and Properties”, *Chem. Mater. 2008, 20*2008 , 1896-1901.

Oberhagemann, Uwe et al., “A Layer Silicate: Synthesis and Structure of the Zeolite Precursor RUB-15”, *Angew. Chem. Int. Ed. Engl. 1996, 35*, No. 23/24 1996 , 2869-2872.

Ruan, Juanfang et al., “Structural Characterization of Interlayer Expanded Zeolite Prepared From Ferrierite Lamellar Precursor”, *Chem. Mater.*, vol. 21, No. 13 2009 , 2904-2911.

Song., J. et al., “Zeolites Synthesis in the System”, *Studies in Surface Science and Catalysis*, vol. 154 2004 , 295-300.

Wu, Peng et al., “Methodology for Synthesizing Crystalline Metallosilicates with Expanded Pore Windows Through Molecular Alkoxysilylation of Zeolitic Lamellar Precursors”, *J. Am. Chem. Soc.* Jun. 4, 2008 , 8178-8187.

“PCT International Search Report for PCT/IB2011/052913”, Nov. 3, 2011, 5 pages.

Kim, Sun J. et al., “Synthesis and characterization of transition metal oxide-pillared materials with mesoporosity from layered silicate ilerite”, *J. Porous Mater*, vol. 13 2006 , 27-35.

“IPRP in PCT/IB2011/052913”, dated Sep. 20, 2012, 6 pgs.

* cited by examiner

*Primary Examiner* — Kuo-Liang Peng
(74) *Attorney, Agent, or Firm* — Servilla Whitney LLC

(57) ABSTRACT

The present invention relates to a pillared silicate compound comprising a layered silicate structure, and bridging metal atoms located between adjacent silicate layers of the silicate structure, wherein said bridging metal atoms form at least one covalent bond to each of the adjacent silicate layers, as well as a process for the preparation of a pillared silicate compound, and further includes a pillared silicate compound obtainable and or obtained according to said process, as well as a method of catalyzing a chemical reaction comprising the step of contacting one or more chemical compounds with the any of the aforementioned pillared silicate compounds.

29 Claims, 30 Drawing Sheets

METAL-BRIDGED PILLARED SILICATE COMPOUNDS AND PROCESS FOR THEIR PRODUCTION

CROSS-REFERENCE TO RELATED APPLICATIONS

This application claims benefit under 35 USC 120 and 365(c) of PCT application PCT/CN 2010/074920 filed on Jul. 2, 2010. The foregoing application is hereby incorporated herein by reference in its entirety.

TECHNICAL FIELD

The present invention relates to a pillared silicate compound comprising a layered silicate structure and bridging metal atoms located between the silicate layers of the silicate structure as well as to a process for the preparation of such a pillared silicate compound, and further relates to a pillared silicate compound obtainable or obtained by said process. Furthermore, the present invention concerns the use of a pillared silicate compound in various applications.

BACKGROUND

In the field of catalysis, and also, for example, in the field of adsorption or adsorption processes, providing novel framework topologies with novel pore architectures plays a crucial role in the development of catalysts, catalyst components, and catalyst support materials displaying novel reactivity and/or improved performance. In this respect, the condensation of layered silicates into new zeolitic frameworks via topotactic procedures is intensively investigated in past and present research.

Thus, synthesis and characterization of products resulting from the reaction of selected layered silicates having MWW-type, FER-type and CDO-type layers with diethoxy dimethyl silane is disclosed in P. Wu et al.; J. Am. Chem. Soc., 130, 2008, pp. 8178-8187. In particular, silylation products described therein are obtained by a method of refluxing specific layered silicate precursors in nitric acid followed by a calcinations procedure. As a result of said procedure, it is possible to obtain a pillared silicate compound having a layered silicate structure, wherein the silicate layers are covalently bound to one another via bridging silicon atoms thus forming a three-dimensional framework.

As further discussed in J. Ruan et al.; Chem. Mater., 21, 2009, pp. 2904-2911, with respect to the alkoxysilylation of an FER lamellar precursor (PREFER), calcinations of the pillared silicate product leads to further reaction of the bridging silicon moieties with one another, such that these become bridged to one another via bridging oxygen atoms. Furthermore, Ruan et al. expand the alkoxysilylation methodology to include the use of hydrothermal methods for inducing silylation.

Accordingly, pillared silicate compounds comprising a layered silicate structure, wherein silicate layers of the silicate structure are bridged by silicon moieties are known in the art. Furthermore, it is known that calcination of said pillared silicate compounds leads to further bridging via condensation of bridging silicon moieties thus forming further Si—O—Si bridging in the interlayer space. Consequently, it is known from the prior art that covalent pillaring of layered silicate compounds may be achieved by an alkoxysilylation procedure, thus affording three-dimensional zeolitic materials.

It would desirable to provide novel pillared silicate compounds displaying novel and improved properties, in particular with respect to the physical properties and catalytic activity thereof.

SUMMARY

Embodiments of the present invention expand the pillaring concept to new types of pillaring structures. According to one or more embodiments, this can be achieved by the pillared silicate compounds according to the present invention, and by the inventive process for obtaining such compounds.

The present invention includes the following embodiments, wherein these include the specific combinations of embodiments as indicated by the respective interdependencies defined therein:

1. A pillared silicate compound comprising
   a layered silicate structure, and
   bridging metal atoms located between adjacent silicate layers of the silicate structure, wherein said bridging metal atoms form at least one covalent bond to each of the adjacent silicate layers.
2. The pillared silicate compound of embodiment 1, wherein the layered silicate structure comprises silicate layers selected from the group consisting of zeolite-type layers, preferably from the group consisting of HEU-type layers, FER-type layers, MWW-type layers, RWR-type layers, CAS-type layers, SOD-type layers, RRO-type layers, or combinations of two or more different types of these zeolite-type layers, wherein even more preferably the layered silicate structure comprises FER-type layers.
3. The pillared silicate compound of embodiment 1 or 2, wherein the layered silicate structure originates from one or more layered silicate compounds and/or is derived or derivable from one or more layered silicate compounds, said one or more layered silicate compounds comprising one or more layered silicates selected from the group consisting of MCM-22, PREFER, Nu-6(2), CDS-1, PLS-1, MCM-47, ERS-12, MCM-65, RUB-15, RUB-18, RUB-20, RUB-36, RUB-38, RUB-39, RUB-40, RUB-42, RUB-51, BLS-1, BLS-3, ZSM-52, ZSM-55, kanemite, makatite, magadiite, kenyaite, revdite, montmorillonite, and combinations of two or more thereof, wherein the one or more layered silicate compounds preferably comprise RUB-36 and/or RUB-39, and even more preferably comprise RUB-36.
4. The pillared silicate compound of any of embodiments 1 to 3, wherein the silicate layers of the layered silicate structure are isomorphously substituted, preferably with one or more elements selected from the group consisting of Al, B, Fe, Ti, Sn, Ga, Ge, Zr, V, Nb, Zn, Li, Be and mixtures of two or more thereof, more preferably from the group consisting of Al, B, Fe, Ti, Sn, Zr, and mixtures of two or more thereof, more preferably from the group consisting of Al, Ti, B, and mixtures of two or more thereof, and wherein even more preferably, the silicate structure is isomorphously substituted with Al and/or Ti.
5. The pillared silicate compound of any of embodiments 1 to 4, wherein the bridging metal atoms comprise one or more metals selected from the group consisting of Li, Be, B, Mg, Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd, Hg, Al, Ga, In, Tl, Ge, Sn, Pb, Bi, Ce, Pr, Nd, Pm, Sm, Eu, Gd, Tb, Dy, Ho, Er, Tm, Yb, Lu, Ac, Th, Pa, U, Np, Pu, and combinations of two or more thereof,
   preferably from the group consisting of Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn Cd, Hg, Al, Ga, In, Tl, Sn, Pb, Bi, Ce, Pr, Nd, Pm, Sm, Eu, Gd, Tb, Dy, Ho, Er, Tm, Yb, Lu, Ac, Th, Pa, U, Np, Pu, and combinations of two or more thereof, and even more preferably from the group consisting of Al, Sn, Ti, Mo, Mn, Fe, Co, Cu, Zn, Zr, Ru, Pd, Ag, Pt, Au, Sm, Eu, and combinations of two or more thereof.

6. The pillared silicate compound of any of embodiments 1 to 5, wherein the bridging metal atoms do not comprise one or more elements selected from the group consisting of Al, B, and Ti, preferably one or more elements selected from the group consisting of Al, B, Fe, Ti, Sn, and Zr, and even more preferably one or more elements selected from the group consisting of Al, B, Fe, Ti, Sn, Ga, Ge, Zr, V, Nb, Zn, Li, and Be.

7. The pillared silicate compound of any of embodiments 3 to 6, wherein when using the Cu K(alpha 1) wavelength in the diffraction experiment, the 2 theta diffraction angle for the maximum peak (100% intensity) in the X-ray diffraction pattern of the pillared silicate compound is from 0.05 to 1.45° 2 theta lower than the 2 theta diffraction angle of the corresponding maximum peak (100% intensity) in the X-ray diffraction pattern of the layered silicate compound, more preferably from 0.10 to 0.95° 2 theta lower, more preferably from 0.15 to 0.75° 2 theta lower, more preferably from 0.20 to 0.55° 2 theta lower, more preferably from 0.25 to 0.50° 2 theta lower, more preferably from 0.30 to 0.45° 2 theta lower, and even more preferably from 0.35 to 0.40° 2 theta lower.

8. The pillared silicate compound of any of embodiments 1 to 7, having an X-ray diffraction pattern of which the maximum peak (100% intensity) is located at a 2 theta diffraction angle in the range of from 3 to 14° 2 theta when using the Cu K(alpha 1) wavelength in the diffraction experiment, preferably in the range of from 4 to 12° 2 theta, more preferably in the range of from 5 to 11° 2 theta, more preferably in the range of from 6.0 to 9.5° 2 theta, more preferably in the range of from 6.5 to 8.7° 2 theta, more preferably of from 7.0 to 8.2° 2 theta, more preferably of from 7.2 to 8.0° 2 theta, more preferably of from 7.40 to 7.80° 2 theta, more preferably of from 7.45 to 7.75° 2 theta, more preferably of from 7.50 to 7.70° 2 theta, and even more preferably of from 7.55 to 7.65° 2 theta.

9. The pillared silicate compound of any of embodiments 1 to 8, having a BET surface area determined according to DIN 66135 in the range of from 50 to 950 $m^2/g$, preferably of from 100 to 800 $m^2/g$, more preferably of from 200 to 600 $m^2/g$, more preferably of from 250 to 470 $m^2/g$, more preferably of from 280 to 450 $m^2/g$, more preferably of from 300 to 430 $m^2/g$, more preferably of from 320 to 420 $m^2/g$, and even more preferably of from 360 to 400 $m^2/g$.

10. A process for the preparation of a pillared silicate compound according to any one of embodiments 1 to 9, comprising the steps of (1) providing an acidic mixture comprising one or more layered silicate compounds, one or more metal compounds, and one or more solvents; and (2) reacting the mixture obtained in step (1) to obtain at least one pillared silicate compound.

11. The process of embodiment 10, wherein the reacting of the mixture in step (2) comprises heating said mixture, wherein said heating is preferably performed under autogenous pressure, more preferably under solvothermal conditions, and even more preferably under hydrothermal conditions.

12. The process of embodiment 11, wherein the heating in step (2) is carried out at a temperature in the range of from 50 to 250° C., preferably of from 90 to 230° C., more preferably of from 110 to 210° C., more preferably of from 130 to 190° C., more preferably of from 140 to 180° C., more preferably of from 145 to 175° C., more preferably of from 150 to 170° C., and even more preferably of from 155 to 165° C.

13. The process of any of embodiments 10 to 12 wherein the one or more solvents comprised in the acidic mixture comprise water, preferably distilled water.

14. The process of any of embodiments 10 to 13, wherein one or more acids are further provided in step (1), said one ore more acids preferably comprising one or more Brønsted acids, more preferably one or more mineral acids, more preferably hydrochloric and/or nitric acid, and even more preferably hydrochloric acid.

15. The process of any of embodiments 10 to 14, wherein the one or more metal compounds comprise one or more Lewis acids, the Lewis acidity being in particular with respect to the one or more solvents, wherein in addition to said one or more Lewis acids, the mixture preferably comprises no hydrochloric acid, more preferably no hydrochloric and/or nitric acid, more preferably no mineral acid, more preferably no Brønsted acid, and even more preferably no acid in addition to the one or more Lewis acids and/or secondary acid products of the one or more Lewis acids.

16. The process of any of embodiments 10 to 15, wherein the pH of the mixture provided in step (1) is in the range of from −0.5 to 5, preferably of from 0 to 4, more preferably of from 0.1 to 3, more preferably of from 0.2 to 2, more preferably of from 0.3 to 1, and even more preferably of from 0.4 to 0.6.

17. The process of any of embodiments 10 to 16, wherein the one or more layered silicate compounds comprise one or more layered silicates selected from the group consisting of MCM-22, PREFER, Nu-6(2), CDS-1, PLS-1, MCM-47, ERS-12, MCM-65, RUB-15, RUB-18, RUB-20, RUB-36, RUB-38, RUB-39, RUB-40, RUB-42, RUB-51, BLS-1, BLS-3, ZSM-52, ZSM-55, kanemite, makatite, magadiite, kenyaite, revdite, montmorillonite, and combinations of two or more thereof, wherein the one or more layered silicate compounds preferably comprise RUB-36 and/or RUB-39, and even more preferably comprise RUB-36.

18. The process of any of embodiments 10 to 17, wherein one or more of the one or more layered silicate compounds are isomorphously substituted, preferably with one or more elements selected from the group consisting of Al, B, Fe, Ti, Sn, Ga, Ge, Zr, V, Nb, Zn, Li, Be and mixtures of two or more thereof, more preferably from the group consisting of Al, B, Fe, Ti, Sn, Zr, and mixtures of two or more thereof, more preferably from the group consisting of Al, Ti, B, and mixtures of two or more thereof, and wherein even more preferably, the silicate structure is isomorphously substituted with Al and/or Ti.

19. The process of any of embodiments 10 to 18, wherein the one or more metal compounds comprise one or more metals selected from the group consisting of Li, Be, B, Mg, Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn Cd, Hg, Al, Ga, In, Tl, Ge, Sn, Pb, Bi, Ce, Pr, Nd, Pm, Sm, Eu, Gd, Tb, Dy, Ho, Er, Tm, Yb, Lu, Ac, Th, Pa, U, Np, Pu, and combinations of two or more thereof, preferably from the group consisting of Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn Cd, Hg, Al, Ga, In, Tl, Sn, Pb, Bi, Ce, Pr, Nd, Pm, Sm, Eu, Gd, Tb, Dy, Ho, Er, Tm, Yb, Lu, Ac, Th, Pa, U, Np, Pu, and combinations of two or more thereof, and even more preferably from the group consisting of Al, Sn, Ti, Mo, Mn, Fe, Co, Cu, Zn, Zr, Ru, Pd, Ag, Pt, Au, Sm, Eu, and combinations of two or more thereof.

20. The process of any of embodiments 10 to 19, wherein the one or more metal compounds comprise one or more metal compounds selected from the group consisting of metal salts, metal complexes, organometallic compounds, and combinations of two or more thereof.

21. The process of embodiment 20, wherein the group of metal salts comprises one or more compounds selected from the group consisting of metal halides, metal hydroxides, metal carbonates, metal carboxylates, metal nitrates, metal nitrites, metal phosphates, metal phosphites, metal phosphonates, metal phosphinates, metal sulfates, metal sulfites, metal sulfonates, metal alkoxides, metal complexes, and combinations and/or mixtures of two or more thereof,
   preferably from the group consisting of metal halides, metal hydroxides, metal carbonates, metal carboxylates, metal nitrates, metal sulphates, metal alkoxides, and combinations and/or mixtures of two or more thereof,
   more preferably from the group consisting of metal halides and/or metal alkoxides, wherein more preferably the metal salts comprise one or more metal halides, and even more preferably one or more metal chlorides.

22. The process of embodiment 20 or 21, wherein the group of organometallic compounds comprises one or more organometallic compounds selected from the group consisting of organoaluminum compounds, organotitanium compounds, organomanganese compounds, organoiron compounds, organocobalt compounds, organocopper compounds, organozinc compounds, organopalladium compounds, organosilver compounds, organotin compounds, organoplatinum compounds, organogold compounds, and mixtures thereof, wherein the organometallic compounds preferably comprise one or more organotin compounds.

23. The process of any of embodiments 10 to 22, wherein the mixture is reacted in step (2) for a period of from 1 to 72 h, preferably of from 8 to 48 h, more preferably of from 10 to 36 h, more preferably of from 12 to 32 h, more preferably of from 14 to 28 h, more preferably of from 16 to 24 h, and even more preferably of from 18 to 22 h.

24. The process of any of embodiments 10 to 23, which further comprises the steps of
   (3) separating the pillared silicate from the mixture obtained according to step (2); and/or
   (4) washing and/or drying the pillared silicate obtained from step (3).

25. The process of any of embodiments 10 to 24, which further comprises the step of
   (5) calcining the pillared silicate obtained in step (2) and/or (3) and/or (4), said calcining preferably being effected at a temperature in the range of from 250 to 850° C., more preferably at a temperature of from 350 to 750° C., more preferably of from 450 to 650° C., more preferably of from 460 to 600° C., more preferably of from 470 to 560° C., more preferably of from 480 to 540° C., and even more preferably of from 490 to 520° C.

26. A pillared silicate compound obtainable or obtained by a process according to any of embodiments 10 to 25, said pillared silicate compound preferably having an X-ray diffraction pattern of which the maximum peak (100% intensity) is at a 2 theta diffraction angle which is from 0.05 to 1.45° 2 theta lower than the 2 theta diffraction angle of the corresponding maximum peak (100% intensity) of at least one of the at least one layered silicate compound provided in step (1) when using the Cu K(alpha 1) wavelength in the diffraction experiment, more preferably from 0.10 to 0.95° 2 theta lower, more preferably from 0.15 to 0.75° 2 theta lower, more preferably from 0.20 to 0.55° 2 theta lower, more preferably from 0.25 to 0.50° 2 theta lower, more preferably from 0.30 to 0.45° 2 theta lower, and even more preferably from 0.35 to 0.40° 2 theta lower.

27. The pillared silicate compound of embodiment 26, having an X-ray diffraction pattern of which the maximum peak (100% intensity) is located at a 2 theta diffraction angle in the range of from 3 to 14° 2 theta when using the Cu K(alpha 1) wavelength in the diffraction experiment, preferably at a 2 theta diffraction angle in the range of from 4 to 12° 2 theta, more preferably of from 5 to 11° 2 theta, more preferably of from 6.0 to 9.5° 2 theta, more preferably of from 7.0 to 8.2° 2 theta, more preferably of from 7.2 to 8.0° 2 theta, more preferably of from 7.40 to 7.80° 2 theta, more preferably of from 7.45 to 7.75° 2 theta, more preferably of from 7.50 to 7.70° 2 theta, and even more preferably of from 7.55 to 7.65° 2 theta.

28. The pillared silicate compound of embodiment 26 or 27, having a BET surface area determined according to DIN 66135 in the range of from 50 to 950 $m^2/g$, preferably of from 100 to 800 $m^2/g$, more preferably of from 200 to 600 $m^2/g$, more preferably of from 250 to 470 $m^2/g$, more preferably of from 280 to 450 $m^2/g$, more preferably of from 300 to 430 $m^2/g$, more preferably of from 320 to 420 $m^2/g$, and even more preferably of from 360 to 400 $m^2/g$.

29. The pillared silicate of any of embodiments 1 to 9 and 26 to 28, comprised in a molding.

30. Use of a pillared silicate compound according to any of embodiments 1 to 9 and 26 to 29 as a molecular sieve, catalyst, catalyst component, catalyst support or binder thereof, as absorbents, for ion exchange, for the production of ceramics, and/or in polymers.

BRIEF DESCRIPTION OF THE DRAWINGS

FIG. 1 further includes the line pattern of the RUB-36 structure for comparison.

DETAILED DESCRIPTION

Figure 1:
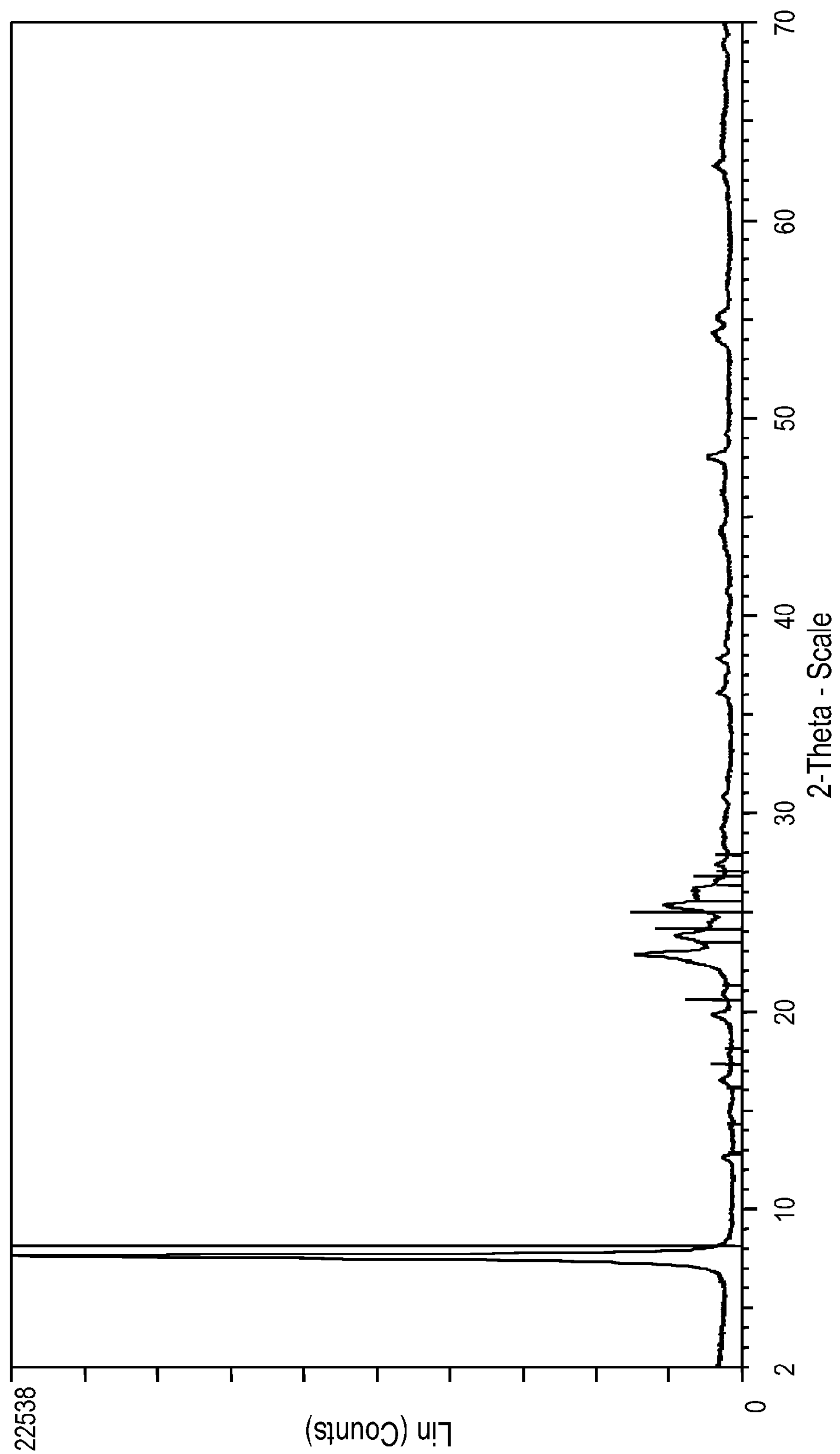
FIG. 1 shows the X-ray diffraction pattern of the pillared silicate compound obtained according to Example 1.

Embodiments of the present invention relates to a pillared silicate compound comprising a layered silicate structure, and bridging metal atoms located between adjacent silicate layers of the silicate structure, wherein said bridging metal atoms form at least one covalent bond to each of the adjacent silicate layers.

It is herewith noted that within the meaning of the present invention, and in particular with respect to specific embodiments thereof, the term “comprising” is preferably used as meaning “consisting of”.

Thus, according to embodiments of the present invention, a pillared silicate compound is surprisingly provided, wherein the bridging elements between adjacent silicate layers of the pillared silicate compound comprise metal atoms forming covalent bonds to the neighboring silicate layers. Within the meaning of the present invention, “adjacent” or “neighboring” layers refers to layers which immediately follow one another in the stacking of a layered structure, and between which a further layer is not comprised.

In particular, it has surprisingly been found that it is possible to introduce catalytically active centers in a layered silicate structure as covalent bridging elements between the silicate layers. More specifically, it has surprisingly been found that a pillared silicate compound may be provided containing catalytically active centers in accurately predefined positions displaying a highly specific environment in a layered silicate structure. Thus, as opposed to catalysts of the prior art which rely on impregnation methods and the like for the loading of catalytically active metals onto a silicate support material, the inventive compounds surprisingly display a very specific incorporation thereof in a predefined manner. For example, according to the present invention, it is actually possible to specifically load a silicate with monoatomic metals at predifined positions, i.e. in a predefined environment.

It must be emphasized, that this greatly contrasts with silicate compounds of the prior art, wherein metals are incorporated in a statistical manner, meaning that they are practically spread over a practically endless number of possible positions of a silicate substrate, in particular with respect to the different environments which may be found at practically every single position of the individual metal atoms. Furthermore, when using the impregnating methods or the like known in the art, it is not possible to avoid the formation of metal clusters and similar aggregations. This not only concerns the loading process itself, but even more applies to the use of such loaded silicates, for example, in catalytic applications involving high temperatures and extreme chemical conditions, wherein diffusion processes greatly accentuate said highly undesirable effect. Thus, according to the present invention, it is possible to provide a silicate structure loaded with metal atoms, wherein said metal atoms not only occupy highly defined positions in an extremely uniform manner, but are also highly stabilized due to covalent bonding with neighboring silicate layers. Without being bound to theory, it is believed that a chelating effect of the neighboring silicate layers to which the bridging metal atoms is responsible for the surprisingly high stability of said positions, which contributes to the considerable advantages of the present invention, in particular with respect to catalytic applications thereof.

Consequently, it is surprisingly possible according to embodiments of the present invention to provide a completely unique and highly designable pillared silicate compound which is tremendously advantageous, in particular since a highly optimized efficiency of the catalytic activity of metal centers may be provided, in addition to a tremendous uniformity of the catalytic activity due to the selective positioning of the metal atoms in a highly ordered silicate structure.

Thus, a catalyst design is provided which is by no means possible according to the known methods, wherein random loading and cluster formation greatly inhibit the possibility of providing catalyst structures exhibiting both a very high activity and selectivity in addition to a tremendous efficiency with respect to the amount of metal which must be loaded for achieving said activity. As a result of this, the present invention also affords an extremely cost-effective catalyst design, since the activity of the catalyst sites is highly optimized, such that only a fraction of the amount of often costly metals usually employed in loaded catalyst structures must be employed for achieving a comparable activity. Furthermore, the amount of the catalyst itself may be greatly reduced due to its tremendous efficiency, as a result of which a highly cost-effective catalyst is provided, which may be used in considerably smaller amounts than conventional catalysts, and is furthermore highly resistant to aging during use, in particular due to increased cluster formation or other forms of deactivation encountered in catalytic applications.

Within the meaning of the present invention, the term "pillared silicate compound" generally refers to any conceivable layered silicate structure, wherein the silicate layers are covalently bound to one another by suitable chemical moieties as bridging elements. Furthermore, according to said definition, bridging is achieved between the surfaces of neighboring silicate layers of a layered silicate structure, wherein a sufficient portion of the respective surfaces forms covalent bonds to said bridging elements. Within the meaning of the present invention, a sufficient portion of a silicate layer surface is covalently bound to bridging elements, preferably when 10% or more of the atoms or chemical moieties located on the silicate layer surface which is capable of forming covalent bonds to said bridging elements actually engage in such chemical bonding, thus forming a covalent bridge to the neighboring silicate layers. Preferably, a sufficient portion of the silicate layer refers to pillared silicate compounds wherein 30% or more of said surface atoms or chemical moieties of the respective silicate layer surfaces engage in such covalent bonds, more preferably 50% or more, more preferably 70% or more, more preferably 80% or more, more preferably 90% or more, more preferably 95% or more, more preferably 98% or more, more preferably 99% or more, more preferably 99.9% or more and even more preferably 99.99% or more.

Furthermore, the term "layered silicate structure" as used in the present invention generally refers to a structure comprising a regular array of silicate sheet layers which are stacked in parallel. In the present invention, the layers contained in said layered silicate structures are accordingly referred to as "silicate layers". Thus, within the meaning of the present invention, a layered silicate structure may refer to such arrangements of silicate layers as may be found in phyllosilicates or also to regular stackings of silicate layers as may be found in layer-based zeolite structures and layered precursors of such layer-based zeolite structures, wherein according to particularly preferred embodiments of the present invention, the layered silicate structure is selected from layer-based zeolite structures and/or layered precursors of such layer-based zeolite structures such as, for example, MCM-22, PREFER, Nu-6(2), CDS-1, PLS-1, MCM-47, ERS-12, MCM-65, RUB-15, RUB-18, RUB-20, RUB-36, RUB-38, RUB-39, RUB-40, RUB-42, RUB-51, BLS-1, BLS-3, ZSM-52, ZSM-55, and combinations of two or more thereof.

Furthermore, the term "covalent" as employed in the present invention for defining the nature of chemical bonding, and in particular of chemical bonding present between the silicate layers and the bridging elements, refers to a chemical bonding interaction between two elements which is essentially non-ionic. More specifically, covalent bonding refers to a binding interaction between said elements which is achieved mainly by interaction of their respective atomic and/or molecular orbitals as opposed to electrostatic interaction as a result of a charge difference and/or polar interactions. Preferably, covalent within the meaning of the present invention defines a bond which is 10% or more of non-ionic nature, more preferably 20% or more, more preferably 30% or more, more preferably 50% or more, more preferably 70% or more, more preferably 90% or more, and even more preferably 95% or more non-ionic in chemical nature.

Accordingly, the pillared silicate compound of embodiments of the present invention does not exclude a certain amount of bridging interaction between the adjacent silicate layers due to ionic interactions and/or polar interactions present between the same and/or due to covalent bridging of the adjacent silicate layers by non-metal atoms, as long as the covalent bridging of said layers is essentially due to covalent bonding thereof via bridging metal atoms as defined herein. In particular, within the meaning of the present invention, the bridging of said layers is "essentially" due to covalent bonding thereof via bridging metal atoms when a sufficient portion of the respective silicate layer surfaces is covalently bound to bridging metal atoms, preferably when 10% or more of the atoms or chemical moieties located on the silicate layer surface which is capable of forming covalent bonds to said bridging metal atoms actually engage in such chemical bonding, thus forming a covalent bridge to the neighboring silicate layers. According to preferred embodiments of the present invention, as essential portion of the silicate layer refers to pillared silicate compounds wherein 30% or more of said surface atoms or chemical moieties of the respective silicate layer surfaces engage in such covalent bonds to the bridging metal atoms, more preferably 50% or more, more preferably 70% or more, more preferably 80% or more, more preferably 90% or more, more preferably 95% or more, more preferably 98% or more, more preferably 99% or more, more preferably 99.9% or more and even more preferably 99.99% or more. It is noted that within the meaning of the present invention, the term "non-metal" atoms generally includes the metalloids Si, As, Se, Sb, Te, Po, and At.

Therefore, according to preferred embodiments of the pillared silicate compound according to the present invention, the covalent bridging between the silicate layers in the pillared silicate compound is essentially due to the covalent bonds formed between the bridging metal atoms and the silicate layers.

In general, according to embodiments of the present invention, the type of covalent bonds formed between the silicate layers and the metal atoms is not particularly restricted, in particular regarding the element or chemical moiety of the silicate layer to which the metal forms said covalent bond. According to particularly preferred embodiments of the present invention, said covalent bonding of the bridging metal atoms refers to covalent bonding between the metal and one or more oxygen atoms contained in the respective silicate layers.

Furthermore, the number and type of covalent bonds formed between the bridging metal atoms and the adjacent silicate layers is not particularly restricted, provided that the bridging metal atoms covalently bind adjacent silicate layers to one another, meaning that at least one covalent bond is respectively formed between the bridging metal atoms and each of the two adjacent silicate layers between which the respective bridging metal atoms are located. Thus, according to certain embodiments, bridging metal atoms may form two or more covalent bonds to either or both of the two adjacent silicate layers between which they are respectively located. Within a preferred meaning of the present invention, two or more covalent bonds may refer to either two or more single bonds, one or more double or triple bonds, or combinations of single, double, and/or triple bonds.

According to the present invention, the pillared silicate compound may comprise any type of silicate layers, provided that said layers are suited for forming covalent bonds to bridging metal atoms located in between said silicate layers. According to preferred embodiments of the present invention, wherein the silicate layers comprise layers as may be found in a zeolite structure and/or in precursor compounds to layer-based zeolite structures, it is further preferred that said silicate layers are selected from the group consisting of zeolite-type layers. In general, such zeolite-type layers may be selected from any conceivable type of zeolite structure provided that these are suitable for forming a layered silicate structure and may suitably bind bridging metal atoms located between the layers in a covalent fashion, wherein said zeolite-type layers are preferably selected from the group consisting of HEU-type layers, FER-type layers, MWW-type layers, RWR-type layers, CAS-type layers, SOD-type layers, RRO-type layers, or combinations of two or more different types of said specific zeolite-type layers. According to particularly preferred embodiments, the pillared silicate compound comprises FER-type layers.

Therefore, according to preferred embodiments of the pillared silicate compound according to the present invention, the layered silicate structure comprises silicate layers selected from the group consisting of zeolite-type layers, preferably from the group consisting of HEU-type layers, FER-type layers, MWW-type layers, RWR-type layers, CAS-type layers, SOD-type layers, RRO-type layers, or combinations of two or more different types of these zeolite-type layers, wherein even more preferably the layered silicate structure comprises FER-type layers.

According to preferred embodiments of the present invention, the layered silicate structure of the pillared silicate compound actually originates from one or more layered silicate compounds, preferably from a layered silicate compound which has been used in its production. In general, the term “layered silicate compound” as employed in the present invention signifies any natural or synthetic layered silicate, wherein preferably said term refers to layered silicates employed as a catalyst and/or as a catalyst substrate in industrial processes. Alternatively or in addition thereto, the layered silicate structure is preferably derivable from one or more layered silicate compounds. Regarding said layered silicate compounds from which the layered silicate structure of the pillared silicate compound preferably originates and/or may be derived from, these include one or more of any conceivable layered silicate compound provided that it is suitable for forming covalent bonds to bridging metal atoms present between its layers and/or that a derivative thereof is capable of doing so. According to preferred embodiments of the present invention, the one or more layered silicate compounds comprise one or more zeolites. Within the meaning of the present invention, layered silicate compounds from which the layered silicate structure of the pillared silicate compound is preferably derived or derivable from includes derivatives of a layered silicate compound, wherein a derivative of a layered silicate compound generally refers to a layered silicate compound which has been subject to one or more physical and/or chemical modifications, preferably to one or more chemical and/or physical modifications for improving its suitability to covalently bind bridging metal atoms within the meaning of the present invention.

According to particularly preferred embodiments of the present invention, said one or more layered silicate compounds comprise one or more layered silicates selected from the group consisting of MCM-22, PREFER, Nu-6(2), CDS-1, PLS-1, MCM-47, ERS-12, MCM-65, RUB-15, RUB-18, RUB-20, RUB-36, RUB-38, RUB-39, RUB-40, RUB-42, RUB-51, BLS-1, BLS-3, ZSM-52, ZSM-55, kanemite, makatite, magadiite, kenyaite, revdite, montmorillonite, and combinations of two or more thereof, wherein the one or more layered silicate compounds preferably comprise RUB-36 and/or RUB-39, and even more preferably comprise RUB-36.

Therefore, according to preferred embodiments of the pillared silicate compound according to the present invention, the layered silicate structure originates from one or more layered silicate compounds and/or is derived or derivable from one or more layered silicate compounds, said one or more layered silicate compounds comprising one or more layered silicates selected from the group consisting of MCM-22, PREFER, Nu-6(2), CDS-1, PLS-1, MCM-47, ERS-12, MCM-65, RUB-15, RUB-18, RUB-20, RUB-36, RUB-38, RUB-39, RUB-40, RUB-42, RUB-51, BLS-1, BLS-3, ZSM-52, ZSM-55, kanemite, makatite, magadiite, kenyaite, revdite, montmorillonite, and combinations of two or more thereof, wherein the one or more layered silicate compounds preferably comprise RUB-36 and/or RUB-39, and even more preferably comprise RUB-36.

Regarding the specific layered silicate compounds defined in the foregoing, RUB-15 relates to a specific type of layered silicates of which the preparation is, for example, disclosed in U. Oberhagemann, P. Bayat, B. Marler, H. Gies, and J. Rius *Angew. Chem., Intern. Ed. Engl.* 1996, 35, pp. 2869-2872. RUB-18 refers to specific layered silicates of which the preparation is, for example, described in T. Ikeda, Y. Oumi, T. Takeoka, T. Yokoyama, T. Sano, and T. Hanaoka *Microporous and Mesoporous Materials* 2008, 110, pp. 488-500. RUB-20 relates to specific layered silicates which may be prepared as, for example, disclosed in Z. Li, B. Marler, and H. Gies *Chem. Mater.* 2008, 20, pp. 1896-1901. RUB-36 refers to specific silicates of which the preparation is, for example, described in J. Song, H. *Gies Studies in Surface Science and Catalysis* 2004, 15, pp. 295-300. RUB-39 relates to specific layered silicates of which the preparation is, for example, described in WO 2005/100242 A1, in particular in Examples 1 and 2 on pages 32 and 33, in WO 2007/042531 A1, in particular in Example 1 on page 38, Example 2 on page 39, Example 3 on page 40, Example 6 on page 41, and Example 7 on page 42, or WO 2008/122579 A2, in particular in Example 1 on page 36 and in Example 3 on page 37, respectively. RUB-51 refers to specific layered silicates of which the preparation is, for example, described in Z. Li, B. Marler, and H. Gies *Chem. Mater.* 2008, 20, pp. 1896-1901. ZSM-52 and ZSM-55 refer to specific layered silicates which may be prepared as, for example, described in D. L. Dorset, and G. J. Kennedy *J. Phys. Chem. B.* 2004, 108, pp. 15216-15222. Finally, RUB- 38, RUB-40, and RUB-42 respectively refer to specific layered silicates as, for example, presented in the presentation of B. Marler and H. Gies at the 15$^{th}$ International Zeolite Conference held in Beijing, China in August 2007.

In particular, according to particularly preferred embodiments of the present invention, wherein the one or more layered silicate compounds comprises RUB-36, it is further preferred that the RUB-36 has an X-ray diffraction pattern comprising at least the following reflections:

| Diffraction angle 2θ/° [Cu K(alpha 1)] | Intensity (%) |
|---|---|
| 7.85-8.05 | 100.0 |
| 17.04-17.24 | 1.6-5.6 |
| 20.26-20.46 | 1.7-5.7 |
| 23.89-24.09 | 4.2-12.2 |
| 24.73-24.93 | 4.8-12.8 |
| 25.30-25.50 | 2.6-6.6 |
| 26.52-26.72 | 0.7-4.7 |

wherein 100% relates to the intensity of the maximum peak in the X-ray diffraction pattern.

According to preferred embodiments of the present invention, the silicate layers of the layered silicate structure comprised in the pillared silicate compound are isomorphously substituted with one or more types of heteroatoms. In general, in said preferred embodiments, any conceivable type of heteroatom may isomorphously substitute at least a portion of the Si atoms in the silicate structure of the silicate layers, provided that the one or more types of heteroatoms are suitable for isomorphous substitution. In particular, it is preferred that the silicate layers are isomorphously substituted with one or more elements selected from the group consisting of Al, B, Fe, Ti, Sn, Ga, Ge, Zr, V, Nb, Zn, Li, Be and mixtures of two or more thereof, more preferably from the group consisting of Al, B, Fe, Ti, Sn, Zr, and mixtures of two or more thereof, more preferably from the group consisting of Al, Ti, B, and mixtures of two or more thereof, and wherein even more preferably, the silicate structure is isomorphously substituted with Al and/or Ti.

According to the present invention, there is no particular restriction with respect to the type of metal atoms used as bridging metal atoms in the pillared silicate compound, provided that said metals are suited for engaging in covalent bonding with the silicate layers of the layered silicate structure comprised therein. Furthermore, within the meaning of the present invention, the bridging metal atoms may comprise monoatomic as well as di-, tri- and polyatomic metal moieties, as well as combinations of two or more thereof, wherein mono- and/or diatomic bridging metal atoms are preferred, monoatomic bridging metal atoms being particularly preferred.

Furthermore, according to preferred embodiments of the present invention, the bridging metal atoms may further bind organic moieties in addition to the silicate layers, the organic moieties preferably only being bound to the bridging metal atoms. According to the present invention, there is no particular restriction with respect to organic moieties which may be further bound to the bridging metal atoms, provided that they do not impair the covalent binding of the metal atoms to the silicate layers.

Furthermore, according to yet further preferred embodiments of the inventive process, the silicate layers of the layered silicate structure may themselves may also contain organic moieties in addition to or alternatively to organic moieties bound to the bridging metal atoms, wherein again, there is no particular restriction with respect to organic moieties which may be contained in the silicate layers of the layered silicate structure, provided that these do not impair the covalent binding of the bridging metal atoms to the silicate layers.

According to preferred embodiments of the present invention, the bridging metal atoms comprise one or more metals selected from the group consisting of Li, Be, B, Mg, Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn Cd, Hg, Al, Ga, In, Tl, Ge, Sn, Pb, Bi, Ce, Pr, Nd, Pm, Sm, Eu, Gd, Tb, Dy, Ho, Er, Tm, Yb, Lu, Ac, Th, Pa, U, Np, Pu, and combinations of two or more thereof, preferably from the group consisting of Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn Cd, Hg, Al, Ga, In, Tl, Sn, Pb, Bi, Ce, Pr, Nd, Pm, Sm, Eu, Gd, Tb, Dy, Ho, Er, Tm, Yb, Lu, Ac, Th, Pa, U, Np, Pu, and combinations of two or more thereof, and even more preferably from the group consisting of Al, Sn, Ti, Mo, Mn, Fe, Co, Cu, Zn, Zr, Ru, Pd, Ag, Pt, Au, Sm, Eu, and combinations of two or more thereof.

According to particularly preferred embodiments of the present invention, the pillared silicate compound comprises two or more different types of bridging metals as bridging elements, thus forming bi- and multifunctional catalysts, respectively. In particular, it has surprisingly been found that bi- and multifunctional catalysts may be provided according to the present invention in the form of the inventive pillared silicate compounds comprising two or more different types of bridging metal atoms as the bridging element covalently binding the silicate layers comprised in the layered silicate structure thereof. Thus, it has unexpectedly been found that it is actually possible to load a silicate compound with two or more different types of bridging metal atoms to afford a catalyst having a specific arrangement of different metal functionalities. In particular, it is possible according to the present invention to provide catalytically active centers of a specific arrangement in a defined environment wherein different metal centers are located at specific positions and at a specific distance from a second type of metal which itself is also located at a specific position in a specific environment. It has, thus, quite unexpectedly been found that it is actually possible to provide specific bi- and multifunctional catalysts displaying a very specific catalytic behavior due to a chemical reactivity which may not be provided by conventional loading methods of a silicate compound. In particular, conventional means involving impregnation of a catalyst support are not suited for the provision of such bi- and multifunctional catalysts due to the complete randomness regarding both the positions at which different types of metals are located and their respective distance to a second type of metal. Furthermore, there is little to no control of cluster formation in the loading methodologies of the prior art, such that it is statistically not possible to provide a bi- or multifunctional catalyst via an impregnation method or the like due to the sheer indefinite possibilities with respect to the arrangement of two or more different types of metals in the loaded silicate compounds.

Consequently, with respect to bi- and multifunctional catalysts, the present invention provides absolutely unprecedented possibilities with respect to the provision of novel catalysts displaying a specific chemical behavior relying on the specific chemical interaction of two or more metal centers.

According to particularly preferred embodiments of a bi- or multifunctional catalyst according to the present invention, the two or more different types of bridging metal atoms are selected from combinations of molybdenum with copper and/ or nickel, said pillared silicate compounds being preferably used in the catalysis of methane to benzene dehydro-aromatization reactions.

Although there is no general restriction according to the present invention with respect to the covalently bridging metal atoms comprised in the pillared silicate compound, it is preferred according to certain embodiments that one or more specific types of metal compounds are not contained as bridging elements in the pillared silicate compound. Within the meaning of the present invention, a pillared silicate compound which does not contain a specific type of metal as covalent bridging element refers to compounds wherein not more than 10% of the total covalent bridging via metal atoms is due to said one or more specific metal elements, preferably not more than 5%, more preferably not more than 1%, more preferably not more than 0.5%, more preferably not more than 0.1%, more preferably not more than 0.01%, and even more preferably not more than 0.001%. Regarding the specific metal elements which the covalently bridging metal atoms of the inventive pillared silicate compound do not comprise, it is preferred that the bridging metal atoms do not comprise one or more elements selected from the group consisting of Al, B, and Ti, preferably one or more elements selected from the group consisting of Al, B, Fe, Ti, Sn, and Zr, and even more preferably one or more elements selected from the group consisting of Al, B, Fe, Ti, Sn, Ga, Ge, Zr, V, Nb, Zn, Li, and Be.

Therefore, according to preferred embodiments of the pillared silicate compound according to the present invention, the bridging metal atoms do not comprise one or more elements selected from the group consisting of Al, B, and Ti, preferably one or more elements selected from the group consisting of Al, B, Fe, Ti, Sn, and Zr, and even more preferably one or more elements selected from the group consisting of Al, B, Fe, Ti, Sn, Ga, Ge, Zr, V, Nb, Zn, Li, and Be.

According to preferred embodiments of the present invention wherein the layered silicate structure comprised in the pillared silicate compound originates from one or more layered silicate compounds and/or may be derived from one or more of said compounds, the presence of the covalent metal bridging according to the present invention generally results in a change in the crystal structure of the pillared silicate compound relative to the layered silicate compound itself, wherein said structural change may usually be detected by X-ray diffraction. In this respect, a common characteristic normally found in the diffraction pattern of both the pillared silicate compound and the layered silicate compound concerns the presence of the highest intensity reflection (100% intensity) at low 2 theta values in the corresponding X-ray diffractogramms. In particular, it may be observed that the highest intensity reflection found in the X-ray diffractogramm of the layered silicate compound is shifted to a new 2 theta value in the X-ray diffractogramm of the pillared silicate compound, wherein said highest intensity reflection of the layered silicate compound is usually located at lower 2 theta values due to interlayer expansion of the layered silicate compound.

According to particularly preferred embodiments of the present invention, when using the Cu K(alpha 1) wavelength in the diffraction experiment, the 2 theta diffraction angle for the maximum peak (100% intensity) in the X-ray diffraction pattern of the pillared silicate compound is from 0.05 to 1.45° 2 theta lower than the 2 theta diffraction angle of the corresponding maximum peak (100% intensity) in the X-ray diffraction pattern of the layered silicate compound, more preferably from 0.10 to 0.95° 2 theta lower, more preferably from 0.15 to 0.75° 2 theta lower, more preferably from 0.20 to 0.55° 2 theta lower, more preferably from 0.25 to 0.50° 2 theta lower, more preferably from 0.30 to 0.45° 2 theta lower, and even more preferably from 0.35 to 0.40° 2 theta lower.

In general, the shift of the highest intensity reflection in the X-ray diffractogramm of the pillared silicate compound relative to the X-ray diffractogramm of the layered silicate compound may refer to the X-ray diffractogramm obtained for the layered silicate compound and/or the pillared silicate compound which have been dried and/or subject to a calcination process, preferably to a calcination process as described below in the section on the inventive preparation process according to preferred embodiments of the present invention. Preferably, however, the shift of the highest intensity reflection refers to the X-ray diffractogramm obtained for the layered silicate compound which has not been subject to calcination compared to the X-ray diffractogramm of the pillared silicate compound which has been dried and/or subject to calcination, preferably to the X-ray diffractogramm of the calcined pillared silicate compound.

In general, there is no restriction according to the present invention as to the location of the highest intensity peak in the X-ray diffractogramm of the pillared silicate compound. According to preferred embodiments, the maximum peak (100% intensity) is located at a 2 theta diffraction angle in the range of from 3 to 14° 2 theta when using the Cu K(alpha 1) wavelength in the diffraction experiment, preferably in the range of from 4 to 12° 2 theta, more preferably in the range of from 5 to 11° 2 theta, more preferably in the range of from 6.0 to 9.5° 2 theta, more preferably in the range of from 6.5 to 8.7° 2 theta, more preferably of from 7.0 to 8.2° 2 theta, more preferably of from 7.2 to 8.0° 2 theta, more preferably of from 7.40 to 7.80° 2 theta, more preferably of from 7.45 to 7.75° 2 theta, more preferably of from 7.50 to 7.70° theta, and even more preferably of from 7.55 to 7.65° 2 theta. In this respect, the X-ray diffraction pattern may be obtained from the dried and/or calcined pillared silicate compound, wherein it is preferably obtained from the calcined pillared silicate compound. As mentioned in the foregoing, the term "calcined" preferably refers to a compound which has been subject to a calcination process as described below with respect to preferred embodiments of the inventive production process.

In general, there is no particular restriction regarding the surface area of the pillared silicate compound of the present invention. According to preferred embodiments, the BET surface area (Brunauer-Emmet-Teller; determined according to DIN 66131 by nitrogen adsorption at 77 K) of the pillared silicate compound is comprised in the range of from 50 to 950 $m^2/g$, preferably of from 100 to 800 $m^2/g$, more preferably of from 200 to 600 $m^2/g$, more preferably of from 250 to 470 $m^2/g$, more preferably of from 280 to 450 $m^2/g$, more preferably of from 300 to 430 $m^2/g$, more preferably of from 320 to 420 $m^2/g$, and even more preferably of from 360 to 400 $m^2/g$. In general, the BET surface area of the pillared silicate compound refers to the dried and/or calcined compound, wherein preferably the surface area refers to the calcined compound. Within the meaning of the present invention, the term "dried" preferably refers to a compound which has been subject to a drying procedure as defined below with respect to the inventive process for the preparation of a pillared silicate compound.

In addition to the pillared silicate compound of the present invention as described in the foregoing, the present invention also relates to a method for the preparation of a pillared silicate compound. In general, according to the present invention, there is no restriction whatsoever regarding the preparation of a pillared silicate compound as defined in the foregoing, provided that it displays the inventive features as defined herein. It has, however, surprisingly been found that a pillared silicate compound may be suitably prepared according to a procedure as outlined below.

Thus, an embodiments of the present invention also relates to a process for the preparation of a pillared silicate compound according to the present invention, comprising the steps of (1) providing an acidic mixture comprising one or more layered silicate compounds, one or more metal compounds, and one or more solvents; and (2) reacting the mixture obtained in step (1) to obtain at least one pillared silicate compound.

According to the present invention, there is no particular limitation as to the one or more layered silicate compounds which may be employed in the inventive process, provided that a pillared silicate compound may be obtained when used in combination with one or more metal compounds for affording at least one pillared silicate compound, i.e. provided that it is suitable for forming covalent bonds to bridging metal atoms present between its layers. Preferably, the one or more layered silicate compounds are selected from layered silicate compounds as defined in the foregoing with respect to preferred embodiments of the inventive pillared silicate compound. Thus, the term "layered silicate compound" as employed in the present invention with respect to the inventive process signifies any natural or synthetic layered silicate, wherein preferably said term refers to layered silicates employed as a catalyst and/or as a catalyst substrate in industrial processes. According to preferred embodiments of the present invention, the one or more layered silicate compounds comprise one or more zeolites. Within the meaning of the present invention, the one or more layered silicate compounds may also comprise one or more derivatives of a layered silicate compound which has been subject to one or more physical and/or chemical modifications, preferably to one or more chemical and/or physical modifications for improving its suitability to covalently bind bridging metal atoms within the meaning of the present invention.

According to particularly preferred embodiments of the inventive process, the one or more layered silicate compounds comprise one or more layered silicates selected from the group consisting of MCM-22, PREFER, Nu-6(2), CDS-1, PLS-1, MCM-47, ERS-12, MCM-65, RUB-15, RUB-18, RUB-20, RUB-36, RUB-38, RUB-39, RUB-40, RUB-42, RUB-51, BLS-1, BLS-3, ZSM-52, ZSM-55, kanemite, makatite, magadiite, kenyaite, revdite, montmorillonite, and combinations of two or more thereof, wherein the one or more layered silicate compounds preferably comprise RUB-36 and/or RUB-39, and even more preferably comprise RUB-36.

With respect to the one or more layered silicate compounds which may be employed in the inventive process, there is no particular restriction with respect to any counterions which may be contained therein, wherein preferably said counterions comprise one or more ions selected from the group consisting of alkali metals, alkaline earth metals, and tetraalkyl ammonium ions, more preferably from the group consisting of alkali metals and tetraalkyl ammonium ions, wherein even more preferably said counterions comprise tetraalkyl ammonium ions, in particular diethyldimethyl-ammonium ions.

Furthermore, according to embodiments of the inventive process which are particularly preferred, at least one layered silicate compound comprising one or more organic templating agents is used, in particular, comprising tetraalkyl ammonium compounds, since it is believed that this promotes the reaction with the one or more metal compounds for formation of the pillared silicate compound. In particular, it is believed that as opposed to alkali metal and/or alkaline earth metal counterions contained in layered silicate compounds, said organic templating agents and, in particular, tetraalkyl ammonium ions do not leave the interlayer space of the layered silicate compounds as a result of the acidity of the mixture provided in step (1). Accordingly, it is actually the presence of organic templating agents and, in particular, tetraalkyl ammonium compounds in one or more layered silicate compounds of preferred embodiments of the inventive process which is believed to allow the one or more metal compounds to form covalent bridges between the silicate layers of the one or more layered silicate compounds under acidic conditions which would otherwise not be possible when using layered silicate compounds containing alkali and/or alkaline earth metals instead of said organic templating agents as counterions. Within the meaning of the present invention, the term "organic templating agent" and "organotemplate" designate any conceivable organic compound used in the synthesis of one or more of the layered silicate compounds used in the inventive process, wherein the organic templating agent is contained in the one or more layered silicate compound provided in step (1).

Therefore, according to particularly preferred embodiments of the present invention, one or more of the one or more layered silicate compounds provided in step (1) preferably contain one or more organic templating agents, said one or more organic templating agents preferably comprising one or more tetraalkyl ammonium ions, and more preferably comprising diethyldimethylammonium.

According to the inventive process, one or more of the one or more layered silicate compounds employed therein may be isomorphously substituted with one or more types of heteroatoms. In general, in said preferred embodiments, any conceivable type of heteroatom may isomorphously substitute at least a portion of the Si atoms in the silicate structure of one or more of the layered silicate compounds, provided that the one or more types of heteroatoms are suitable for isomorphous substitution. According to particularly preferred embodiments of the inventive process, one or more layered silicate compounds used therein are isomorphously substituted with one or more elements selected from the group consisting of Al, B, Fe, Ti, Sn, Ga, Ge, Zr, V, Nb, Zn, Li, Be and mixtures of two or more thereof, more preferably from the group consisting of Al, B, Fe, Ti, Sn, Zr, and mixtures of two or more thereof, more preferably from the group consisting of Al, Ti, B, and mixtures of two or more thereof, and wherein even more preferably, the silicate structure is isomorphously substituted with Al and/or Ti.

With respect to the one or more metal compounds used in the inventive process, there is no restriction as to the type and/or number of metals used provided that they are suitable for covalent bridging of the silicate layers of the one or more layered silicate compounds to afford a pillared silicate compound. In particular, the one or more metal compounds may comprise monoatomic as well as di-, tri- and polyatomic metal species, as well as combinations of two or more thereof, wherein metal compounds comprising mono- and/or diatomic metal species are preferred, metal compounds comprising monoatomic metal species being particularly preferred. Furthermore, there is no particular restriction according to the inventive process regarding the oxidation state of the metal species contained in the one or more metal compounds, provided that a pillared silicate compound may be obtained when used in the inventive process.

According to particularly preferred embodiments of the inventive process, the one or more metal compounds comprise one or more metals selected from the group consisting of Li, Be, B, Mg, Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn Cd, Hg, Al, Ga, In, Tl, Ge, Sn, Pb, Bi, Ce, Pr, Nd, Pm, Sm, Eu, Gd, Tb, Dy, Ho, Er, Tm, Yb, Lu, Ac, Th, Pa, U, Np, Pu, and combinations of two or more thereof, preferably from the group consisting of Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn Cd, Hg, Al, Ga, In, Tl, Sn, Pb, Bi, Ce, Pr, Nd, Pm, Sm, Eu, Gd, Tb, Dy, Ho, Er, Tm, Yb, Lu, Ac, Th, Pa, U, Np, Pu, and combinations of two or more thereof, and even more preferably from the group consisting of Al, Sn, Ti, Mo, Mn, Fe, Co, Cu, Zn, Zr, Ru, Pd, Ag, Pt, Au, Sm, Eu, and combinations of two or more thereof.

As with respect to the one or more metals contained in the one or more metal compounds used in embodiments of the inventive process, there is also no particular limitation according to the present invention as to the particular form in which the one or more metal compounds are employed in the inventive process, provided that they may be reacted with the one or more layered silicate compounds for forming a pillared silicate compound containing one or more of said metals as bridging metal atoms covalently bridging the silicate layers. Preferably, the one or more metal compounds are used in the form of a metal salt, a metal complex, and/or as an organometallic compound.

Thus, according to preferred embodiments of the inventive process, the one or more metal compounds comprise one or more metal compounds selected from the group consisting of metal salts, metal complexes, organometallic compounds, and combinations of two or more thereof.

Regarding the metal salts preferably used in the inventive process, there is no particular restriction regarding the one or more types of counterions to the metal ions contained in said salts, provided that said metal salt is suitable for reacting with the layered silicate compound to form the pillared silicate compound. According to preferred embodiments, the metal salts are selected from the group consisting of metal halides, metal hydroxides, metal carbonates, metal carboxylates, metal nitrates, metal nitrites, metal phosphates, metal phosphites, metal phosphonates, metal phosphinates, metal sulfates, metal sulfites, metal sulfonates, metal alkoxides, metal complexes, and combinations and/or mixtures of two or more thereof, preferably from the group consisting of metal halides, metal hydroxides, metal carbonates, metal carboxylates, metal nitrates, metal sulphates, metal alkoxides, and combinations and/or mixtures of two or more thereof, more preferably from the group consisting of metal halides and/or metal alkoxides, wherein more preferably the metal salts comprise one or more metal halides, and even more preferably one or more metal chlorides.

With respect to the metal complexes which may be used in preferred embodiments of the inventive process, these are not particularly restricted, provided that they are suitable for reacting with one or more of the layered silicate compounds for affording a pillared silicate according to the present invention. Preferably the metal complexes are at least in part ionic, such that they constitute metal salts which are further preferred according to the present invention. Further preferred according to the present invention is the use of chelate complexes as the one or more metal complexes, wherein there is no particular restriction to the type of chelating ligand contained therein, in particular with respect to their denticity, wherein bi- and tridentate chelate ligands are preferred, bidentate chelate ligands being particularly preferred. Furthermore, it is preferred that the chelating ligand is an organic chelating ligand, and even more preferably a bidentate chelating ligand, wherein according to particularly preferred embodiments the chelating ligand is acetylacetonate.

Concerning the organometallic compounds which may be used in preferred embodiments of the inventive process, there is again no specific restriction as to the one or more organic moieties contained in said compound, provided that the organometallic compound is suited for reacting with the one or more layered silicate compounds to form a pillared silicate compound. According to preferred embodiments, the one or more organometallic compounds are selected from the group consisting of organoaluminum compounds, organotitanium compounds, organomanganese compounds, organoiron compounds, organocobalt compounds, organocopper compounds, organozinc compounds, organopalladium compounds, organosilver compounds, organotin compounds, organoplatinum compounds, organogold compounds, and mixtures thereof, wherein the organometallic compounds preferably comprise one or more organotin compounds. Among the organotin compounds preferably used according to the present invention, organoditin compounds containing the $Sn_2$ diatomic metal moiety are further preferred.

Finally, regarding the one or more solvents which may be used in the inventive process, there is no particular restriction the type of solvent or solvent mixture used therein provided that said one or more solvents allow for the reaction of the one or more metal compounds with the one or more layered silicate compounds to provide a pillared silicate compound according to the present invention. Thus, any conceivable solvent may be comprised in the acidic mixture including water and organic solvents such as alcohols and, in particular, methanol and/or ethanol, wherein preferably the one or more solvents comprise water and, more preferably, distilled water.

Regarding the acidity of the mixture provided in step (1) of the inventive process, said acidity is preferably due to the presence of one or more acids preferably selected from the group of Brønsted and/or Lewis acids. Thus, according to certain embodiments of the present invention, the acidity of the mixture in step (1) is at least in part due to the presence of one or more acids further provided in step (1), said one ore more acids preferably comprising one or more Brønsted acids, more preferably one or more mineral acids, more preferably hydrochloric and/or nitric acid, and even more preferably hydrochloric acid. According to preferred embodiments, wherein the one or more acids further provided in step (1) comprise nitric acid, it is further preferred that no chloride and, in particular, no halides are present in the reaction mixture, such that a chloride- and/or halide-free pillared silicate compound may be provided.

According to further embodiments of the present invention, the acidity of the mixture in step (1) is at least due to the presence of one or more Lewis acids, wherein said one or more Lewis acids preferably comprise one or more of the metal compounds provided in step (1) for reaction with the one or more layered silicate compounds. According to the present invention, the Lewis acidity is in particular given with respect to one or more of the solvents present in the mixture according to step (1) of the inventive process, i.e. one or more of the Lewis acids engages in a Lewis acid-Lewis base interaction with one or more of the solvents acting as the Lewis base.

According to embodiments of the present invention, wherein one or more of the metal compounds comprised in the mixture of step (1) displays Lewis acidity, it is further preferred that said mixture comprises no hydrochloric acid or, given the case that one or more of the Lewis acids and/or one or more further metal compounds is a chloride, no additional hydrochloric acid, such that a reaction mixture is provided which contains no chloride, or which contains no additional chloride in addition to any chloride contained in said one or more metal compounds. Even more preferably, the acidity of the mixture according to step (1) is substantially or entirely due to the one or more Lewis acids comprised in the one or more metal compounds, such that the mixture preferably contains no hydrochloric acid, more preferably no hydrochloric and/or nitric acid, more preferably no mineral acid, more preferably no Brønsted acid, and even more preferably no acid in addition to the one or more Lewis acids. Within the meaning of the present invention, further acid in addition to one or more Lewis acids comprised in the one or more metal compounds does not include secondary acid products which are generated by acid-base reaction of the one or more Lewis acids with one or more of the solvents, and in particular with water. Such reactions include, for example, the reaction of one or more Lewis acids comprised in the one or more metal compounds with water thus forming hydronium ions.

Therefore, according to preferred embodiments of the present invention, wherein the one or more metal compounds comprise one or more Lewis acids, the Lewis acidity being in particular with respect to the one or more solvents, it is further preferred that in addition to said one or more Lewis acids, the mixture comprises no further hydrochloric acid, more preferably no further hydrochloric and/or nitric acid, more preferably no further mineral acid, more preferably no further Brønsted acid, and even more preferably no further acid in addition to the one or more Lewis acids and/or secondary acid products of the Lewis acids.

According to further embodiments of the present invention which are particularly preferred, the mixture provided in step (1) of the inventive process comprises substantially no chloride, and preferably substantially no halides. In particular, a substantial amount of chloride or halides refers to an amount in the mixture of 1 wt.-% or less, preferably of 0.5 wt.-% or less, more preferably of 0.1 wt.-% or less, more preferably of 0.01 wt.-% or less, more preferably of 0.001 wt.-% or less, and even more preferably of 0.0001 wt.-% or less.

According to the inventive process, the pH of the mixture provided in step (1) is not particularly restricted, provided that the acidity is sufficient for allowing the reaction of the one or more metal compounds with the one or more layered silicate compounds for producing a pillared silicate compound. According to preferred embodiments, the pH of the mixture provided in step (1) is in the range of from −0.5 to 5, preferably of from 0 to 4, more preferably of from 0.1 to 3, more preferably of from 0.2 to 2, more preferably of from 0.3 to 1, and even more preferably of from 0.4 to 0.6.

With respect to reacting of the mixture obtained in step (1) in step (2), there is no particular limitation as to the reaction conditions, in particular with respect to temperature, pressure and/or duration of the reaction, provided that the one or more metal compounds react with the one or more layered silicate compounds in a chemical transformation leading to a pillared silicate compound according to the present invention. According to preferred embodiments of the inventive process, reacting of the mixture in step (2) involves heating of said mixture. According to preferred embodiments involving the heating of the mixture obtained in step (1) in step (2), there is no particular limitation as to the temperature at which the mixture is heated, nor with respect to the duration of heating, provided that a pillared silicate compound is obtained in step (2). According to particularly preferred embodiments, heating in step (2) is carried out at a temperature in the range of from 50 to 250° C., preferably of from 90 to 230° C., more preferably of from 110 to 210° C., more preferably of from 130 to 190° C., more preferably of from 140 to 180° C., more preferably of from 145 to 175° C., more preferably of from 150 to 170° C., and even more preferably of from 155 to 165° C. According to the process of the present invention it is further preferred that the mixture is reacted in step (2), preferably by heating, for a period of from 1 to 72 h, preferably of from 8 to 48 h, more preferably of from 10 to 36 h, more preferably of from 12 to 32 h, more preferably of from 14 to 28 h, more preferably of from 16 to 24 h, and even more preferably of from 18 to 22 h.

Furthermore, according to embodiments of the present invention which are particularly preferred, heating in step (2) is carried out at a temperature in the range of from 52 to 150° C. for a period of from 1 to 72 h, preferably at a temperature of from 92 to 130° C. for a period of from 8 to 48 h, more preferably at a temperature of from 110 to 210° C. for a period of from 10 to 36 h, more preferably at a temperature of from 130 to 190° C. for a period of from 12 to 32 h, more preferably at a temperature of from 140 to 180° C. for a duration of from 14 to 28 h, more preferably at a temperature of from 145 to 175° C. for a duration of from 16 to 24 h, and even more preferably at a temperature of from 150 to 170° C. for a duration of from 18 to 22 h.

According to preferred embodiments of the present invention wherein reacting of the mixture obtained in step (1) in step (2) involves heating of said mixture, there is no particular restriction as to the pressure at which said step of heating is conducted. According to the present invention, it is however preferred that said heating is performed under autogenous pressure such as in an autoclave. More preferably, the heating in step (2) is performed under solvothermal conditions, and even more preferably under hydrothermal conditions, solvothermal conditions generally referring to the heating of the reaction mixture under autogenous pressure at a temperature equal to or above the boiling point of any one of the one or more solvents contained in said mixture, or above the boiling point of the solvent mixture, and hydrothermal conditions referring to the heating of the reaction mixture under autogenous pressure at a temperature of 100° C. or higher.

Therefore, the present invention also relates to preferred embodiments, wherein the reacting of the mixture in step (2) comprises heating said mixture, wherein said heating is preferably performed under autogenous pressure, more preferably under solvothermal conditions, and even more preferably under hydrothermal conditions.

According to the present invention, the pillared silicate compound obtained in step (2) may be subjected to an appropriate work-up and/or further treatment thereof. In particular, the inventive process preferably includes a further step (3) of separating the pillared silicate compound from the mixture obtained according to step (2). In particular, the pillared silicate compound may be isolated from the one or more solvents present in the reaction product of step (2) by any conceivable means, such as by filtration, ultrafiltration, diafiltration, centrifugation, spray-drying and/or decantation methods, wherein filtration methods can involve suction and/or pressure filtration steps. Preferably, said separation of the pillared silicate is achieved by filtration and/or spray drying of the reaction mixture.

Furthermore, in addition to or alternatively to step (3), the inventive process preferably further includes a step (4) of washing and/or drying the optionally separated pillared silicate compound obtained in step (2). Said washing may be achieved by any conceivable means using any conceivable washing agents. Washing agents which may be used are, for example, water, alcohols, such as methanol, ethanol or propanol, or mixtures of two or more thereof. Examples of mixtures are mixtures of two or more alcohols, such as methanol and ethanol or methanol and propanol or ethanol and propanol or methanol and ethanol and propanol, or mixtures of water and at least one alcohol, such as water and methanol or water and ethanol or water and propanol or water and methanol and ethanol or water and methanol and propanol or water and ethanol and propanol or water and methanol and ethanol and propanol. Water or a mixture of water and at least one alcohol, preferably water and ethanol, is preferred, distilled water being very particularly preferred as the only washing agent. Alternatively or in addition to said washing procedure, the pillared silicate compound may first be separated according to step (3) and subsequently washed with a solvent or solvent mixture as defined in the foregoing.

In addition to or alternatively to the preferred separation and/or washing the pillared silicate compound obtained in step (2), said pillared silicate compound may be subject to a step of drying. Said drying process may be conducted at any conceivable temperature, provided that solvent residues and/or moisture comprised in the pillared silicate compound is removed. Accordingly, said drying procedure may be achieved by desiccation, freeze-drying, heating, and/or applying vacuum to the pillared silicate compound obtained in step (2) or (3) or obtained after washing according to step (4). According to preferred embodiments of the present invention, drying is performed after having separated the pillared silicate compound from the mixture of step (2) according to step (3) and, more preferably, after having also washed the pillared silicate compound according to step (4), wherein, even more preferably, said compound is washed until pH neutrality of the one or more washing solvents is achieved which is preferably water and, even more preferably, distilled water.

Thus, according to preferred embodiments, the inventive process further comprises the steps of (3) separating the pillared silicate from the mixture obtained according to step (2); and/or (4) washing and/or drying the pillared silicate obtained from step (3).

According to particularly preferred embodiments, drying is achieved by heating of the pillared silicate compound at a temperature in the range of from 50 to 200° C., preferably in the range of from 80 to 160° C., more preferably in the range of from 100 to 140° C., and even more preferably in the range of from 110 to 130° C. In general, the optional drying procedure is performed for a duration which allows for the substantial removal of any solvents and/or moisture from the pillared silicate compound, wherein, preferably, drying is performed for a duration ranging from 1 to 48 h, preferably from 2 to 24 h, more preferably from 3 to 16 h, more preferably from 4 to 12 h, and even more preferably from 5 to 7 h.

According to a further preferred embodiment of the inventive process, the pillared silicate compound obtained in step (2) is directly subject to at least one step of drying, preferably to spray drying and or spray granulation, without isolating, washing, or drying of the pillared silicate compound beforehand. Directly subjecting the mixture obtained from step (2) of the inventive process to a spray drying or spray granulation stage has the advantage that isolation and drying is performed in a single stage.

In addition to or alternatively to any one of the separating, washing and/or drying procedures defined in optional steps (3) and (4), the pillared silicate compound obtained in step (2) is preferably subjected to a step (5) of calcination. In principle, calcination may be conducted at any conceivable temperature, provided that a thermally stable pillared silicate compound is obtained without substantial deterioration of the crystalline structure present in the pillared silicate compound as obtained in step (2). According to preferred embodiments, calcination of the pillared silicate compound is effected at a temperature in the range of from 250 to 850° C., more preferably at a temperature of from 350 to 750° C., more preferably of from 450 to 650° C., more preferably of from 460 to 600° C., more preferably of from 470 to 560° C., more preferably of from 480 to 540° C., and even more preferably of from 490 to 520° C.

Therefore, according to preferred embodiments, the inventive process for the preparation of a pillared silicate compound further comprises the step of (5) calcining the pillared silicate obtained in step (2) and/or (3) and/or (4), said calcining preferably being effected at a temperature in the range of from 250 to 850° C., more preferably at a temperature of from 350 to 750° C., more preferably of from 450 to 650° C., more preferably of from 460 to 600° C., more preferably of from 470 to 560° C., more preferably of from 480 to 540° C., and even more preferably of from 490 to 520° C.

In particular, calcination of the pillared silicate compound is particularly preferred in cases wherein one or more layered silicate compounds containing organic templating agents are employed in the inventive process, preferably wherein one or more layered silicate compounds contain tetraalkyl ammonium ions, more preferably diethyldimethylammonium, the calcination thus serving to remove said organic compounds from the pillared silicate product.

According to particular embodiments of the present invention, the specific one or more metal compounds used in the inventive process lead to covalent bridging of the silicate layers of the layered silicate compound via bridging metal atoms, wherein said metal atoms further bind organic moieties, said organic moieties preferably only being bound to the bridging metal atoms. Within the meaning of the present invention the term “organic moiety” preferably does not designate organic templating agents preferably contained in the one or more layered silicate compounds. In particular, it may be desirable according to said embodiments that said organic moieties are preserved in view of their hydrophobic properties and/or in view of a specific activation of the metal bridging centers for catalysis. Furthermore, according to yet further preferred embodiments of the inventive process, the one or more layered silicate compounds themselves may contain organic moieties in the silicate layers which at least in part may be preserved in the pillared silicate compound obtained in step (2). In either case, or in embodiments of the inventive process wherein the at least one pillared silicate compound obtained in step (2) contains organic moieties attached to the bridging metal atoms as well as organic moieties contained in and/or on the silicate layers, it may be preferable not to calcine said resulting pillared silicate compound for preserving the desired physical and/or catalytic properties which rely on the presence of said organic moieties. According to the present invention, there is no particular restriction with respect to the organic moieties which are preferably bound to the bridging metal atoms, as well as with respect to organic moieties preferably contained in and/or on the silicate layers of the layered silicate compound, provided that they do not impair the covalent binding of the metal atoms to the silicate layers for obtaining a pillared silicate compound in step (2).

Consequently, according to embodiments of the inventive process which are further preferred, the pillared silicate compound obtained in step (2) and/or (3) and/or (4) is not subject to a step of calcination.

In addition to the pillared silicate compound of the present invention as defined in the foregoing, the present invention also relates to a pillared silicate compound which is obtainable or obtained according to the inventive process. In particular, the same preferably applies with respect to a pillared silicate compound obtainable or obtained according to the inventive process as to the inventive pillared silicate compound as described in the foregoing, in particular with respect to the specific X-ray diffraction patterns of preferred pillared silicate compounds obtained according to the inventive process and/or regarding the preferred shift of the highest intensity reflection observed in the X-ray diffraction pattern of the pillared silicate compound relative to the highest intensity reflection contained in the X-ray diffraction pattern of one or more of the layered silicate compounds provided in step (1) of the inventive process.

Therefore, the present invention also relates to a pillared silicate compound which is obtainable or obtained by the process for the preparation of a pillared silicate compound according to the present invention as described in the foregoing.

According to the present invention, there is no particular restriction with respect to a pillared silicate compound which is obtainable or obtained according to the inventive process, in particular regarding the process by which said pillared silicate compound has been actually obtained. It is however preferred that said obtainable or obtained pillared silicate compound has an X-ray diffraction pattern of which the maximum peak (100% intensity) is at a 2 theta diffraction angle which is from 0.05 to 1.45° 2 theta lower than the 2 theta diffraction angle of the corresponding maximum peak (100% intensity) of at least one of the at least one layered silicate compound provided in step (1) when using the Cu K(alpha 1) wavelength in the diffraction experiment, more preferably from 0.10 to 0.95° 2 theta lower, more preferably from 0.15 to 0.75° 2 theta lower, more preferably from 0.20 to 0.55° 2 theta lower, more preferably from 0.25 to 0.50° 2 theta lower, more preferably from 0.30 to 0.45° 2 theta lower, and even more preferably from 0.35 to 0.40° 2 theta lower. According to said preferred embodiments, it is, however, not necessary that the pillared silicate compound which is obtainable or obtained according to the inventive process has actually been obtained according to a process using the at least on pillared silicate compound.

Furthermore no particular restriction applies according to the present invention regarding the location of the highest intensity peak in the X-ray diffractogramm of the pillared silicate compound which is obtainable or obtained according to the inventive process. It is, however, preferred according to the present invention that said pillared silicate compound has an X-ray diffraction pattern of which the maximum peak (100% intensity) is located at a 2 theta diffraction angle in the range of from 3 to 14° 2 theta when using the Cu K(alpha 1) wavelength in the diffraction experiment, preferably at a 2 theta diffraction angle in the range of from 4 to 12° 2 theta, more preferably of from 5 to 11° 2 theta, more preferably of from 6.0 to 9.5° 2 theta, more preferably of from 7.0 to 8.2° 2 theta, more preferably of from 7.2 to 8.0° 2 theta, more preferably of from 7.40 to 7.80° 2 theta, more preferably of from 7.45 to 7.75° 2 theta, more preferably of from 7.50 to 7.70° 2 theta, and even more preferably of from 7.55 to 7.65° 2 theta.

Regarding the physical properties of the pillared silicate compound which is obtainable or obtained according to the inventive process, no particular restrictions apply which are not necessarily due to the features of the pillared silicate compound obtainable or obtained according to the inventive process as defined herein. This applies, for example, to the specific surface area of the pillared silicate compound, wherein it is however preferred that the pillared silicate compound obtainable or obtained by the inventive process has a BET surface area determined according to DIN 66135 in the range of from 50 to 950 $m^2/g$, preferably of from 100 to 800 $m^2/g$, more preferably of from 200 to 600 $m^2/g$, more preferably of from 250 to 470 $m^2/g$, more preferably of from 280 to 450 $m^2/g$, more preferably of from 300 to 430 $m^2/g$, more preferably of from 320 to 420 $m^2/g$, and even more preferably of from 360 to 400 $m^2/g$. In general, the BET surface area of the pillared silicate compound obtainable or obtained according to the inventive process refers to the dried and/or calcined compound, wherein preferably the surface area refers to the calcined compound. Within the meaning of the present invention, the term "dried" preferably refers to a pillared silicate compound which has been subject to a drying procedure as defined above with respect to the inventive process for the preparation of a pillared silicate compound.

In addition to the pillared silicate compound defined in the foregoing including the pillared silicate compound obtainable or obtained according to the inventive process, the present invention further relates to a molding containing one or more of said pillared silicate compounds. In particular, in many technical applications, the user often desires to employ pillared silicate compounds which have been processed to moldings, instead of the pillared silicate compounds as such. Such moldings are necessary in particular in many industrial processes, in order, for example, to be able to expediently operate separations of substances from mixtures in, for example, tube reactors.

The present invention accordingly also relates to the pillared silicate compound according to the present invention, preferably to the calcined form thereof, as described above, which is comprised in a molding, and/or to a pillared silicate compound which is obtainable or obtained according to the inventive process which is comprised in a molding.

In general, the molding may comprise all conceivable further compounds in addition to the at least one pillared silicate compound of the present invention, provided that it is ensured that the resulting molding is suitable for the desired application.

In the context of the present invention, it is preferred if at least one suitable binder material is used in the production of the molding. In the context of this preferred embodiment, more preferably a mixture of at least one pillared silicate compound and the at least one binder is prepared. Suitable binders are in general all compounds which impart adhesion and/or cohesion between particles of the pillared silicate compound which are to be bound, over and above the physisorption which may be present without a binder. Examples of such binders are metal oxides, such as $SiO_2$, $Al_2O_3$, $TiO_2$, $ZrO_2$ or MgO, or clays or mixtures of two or more of these compounds. As $Al_2O_3$ binders, clay minerals and naturally occurring or synthetic aluminas, for example alpha-, beta-, gamma-, delta-, eta-, kappa-, chi- or theta-alumina and the inorganic or organometallic precursor compounds thereof, such as gibbsite, bayerite, boehmite, pseudo-boehmite or trialkoxyaluminates, such as aluminum triisopropylate are preferred in particular.

Further preferred binders are amphiphilic compounds having a polar and a nonpolar moiety, and graphite. Further binders are, for example, clays, such as montmorillonites, kaolins, bentonites, halloysites, dickites, nacrites or anaxites. These binders can be used as such. In the context of the present invention, it is also possible to use compounds from which the binder is formed in at least one further step in the production of the moldings. Examples of such binder precursors are tetraalkoxysilanes, tetraalkoxytitanates, tetraalkoxyzirconates or a mixture of two or more different tetraalkoxysilanes or a mixture of two or more different tetraalkoxytitanates or a mixture of two or more different tetraalkoxyzirconates or a mixture of at least one tetraalkoxysilane and at least one tetraalkoxytitanate or of at least one tetraalkoxysilane and at least one tetraalkoxyzirconate or of at least one tetraalkoxytitanate and at least one tetraalkoxyzirconate or a mixture of at least one tetraalkoxysilane and at least one tetraalkoxytitanate and at least one tetraalkoxyzirconate. In the context of the present invention, binders which either completely or partly consist of $SiO_2$ or are a precursor of $SiO_2$, from which $SiO_2$ is formed in at least one further step in the production of the moldings are to be mentioned. In this context, both colloidal silica and “wet process” silica as well as “dry process” silica can be used. These are very particularly preferably amorphous silica, the size of the silica particles being, for example, in the range of from 5 to 100 nm and the surface of the silica particles being in the range of from 50 to 500 $m^2/g$. Colloidal silica, preferably in the form of an alkaline and/or ammoniacal solution, more preferably in the form of an ammoniacal solution, is, for example, commercially available as, inter alia, Ludox®, Syton®, Nalco® or Snowtex®. “Wet process” silica is, for example, commercially available, inter alia, as Hi-Sil®, Ultrasil®, Vulcasil®, Santocel®, Valron-Estersil®, Tokusil® or Nipsil®. “Dry process” silica is, for example, commercially available, inter alia, as Aerosil®, Reolosil®, Cab-O-Sil®, Fransil® or Arc-Silica®. The binders are preferably used in an amount which leads to the finally resulting moldings whose binder content is up to 80% by weight, more preferably in the range of from 5 to 80% by weight, more preferably in the range of from 10 to 70% by weight, more preferably in the range of from 10 to 60% by weight, more preferably in the range of from 15 to 50% by weight, more preferably in the range of from 15 to 45% by weight, particularly preferably in the range of from 15 to 40% by weight, based in each case on the total weight of the finally resulting molding. The term “finally resulting molding” as used in the context of the present invention relates to a molding as obtained from the drying and calcining steps (IV) and/or (V), as described below, particularly preferably obtained from (V).

The mixture of binder or precursor of a binder and the at least one pillared silicate compound can be mixed with at least one further compound for further processing and for the formation of a plastic material. Here, inter alia, pore formers may preferably be mentioned. In the process of the present invention, all compounds which, with regard to the finished molding, provide a certain pore size and/or a certain pore size distribution and/or certain pore volumes can be used as pore formers. Preferably used pore formers in the process of the present invention are polymers which are dispersible, suspendable or emulsifiable in water or in aqueous solvent mixtures. Preferred polymers here are polymeric vinyl compounds, for example polyalkylene oxides, such as polyethylene oxides, polystyrene, polyacrylates, polymethacrylates, polyolefins, polyamides and polyesters, carbohydrates, such as cellulose or cellulose derivatives, for example methylcellulose, or sugars or natural fibers. Further suitable pore formers are, for example, pulp or graphite. If pore formers are used in the preparation of the mixture according to (I), the pore former content, preferably the polymer content of the mixture according to (I) is preferably in the range of from 5 to 90% by weight, preferably in the range of from 15 to 75% by weight, and particularly preferably in the range of from 25 to 55% by weight, based in each case on the amount of at least one pillared silicate compound in the mixture according to (I). If desired for the pore size distribution to be achieved, a mixture of two or more pore formers may also be used. In a particularly preferred embodiment of the process of the present invention, as described below, the pore formers are removed in a step (V) by calcination to give the porous molding.

In the context of a likewise preferred embodiment of the present invention, at least one pasting agent is added in the preparation of the mixture according to (I). Pasting agents which may be used are all compounds suitable for this purpose. These are preferably organic, in particular hydrophilic polymers, for example cellulose, cellulose derivatives, such as methylcellulose, starch, such as potato starch, wallpaper paste, polyacrylates, polymethacrylates, polyvinyl alcohol, polyvinylpyrrolidone, polyisobutene or polytetrahydrofuran. Accordingly, particular compounds which also act as pore formers can be used as pasting agents. In a particularly preferred embodiment of the process of the present invention as described below, these pasting agents are removed in a step (V) by calcination to give the porous molding.

According to a further embodiment of the present invention, at least one acidic additive may added during the preparation of the mixture according to (I). Organic acidic compounds which can be removed in the preferred step (V), as described below, by calcination are very particularly preferred. Carboxylic acids, for example formic acid, oxalic acid and/or citric acid, are particularly preferred. It is also possible to use two or more of these acidic compounds.

The order of addition of the components of the mixture according to (I) which contains the at least one pillared compound is not critical. It is both possible first to add the at least one binder, then the at least one pore former and the at least one acidic compound and finally the at least one pasting agent and to interchange the sequence with regard to the at least one binder, the at least one pore former, the at least one acidic compound and the at least one pasting agent.

After the addition of the binder to the at least one pillared silicate compound, to which, if appropriate, at least one of the compounds described above have already been added, the mixture according to (I) is, as a rule, homogenized for from 10 to 180 minutes. Inter alia, kneaders, edge mills or extruders are particularly preferably used for the homogenization. The mixture is preferably kneaded. On the industrial scale, treatment in an edge mill is preferably employed for the homogenization. The homogenization is carried out as a rule at temperatures in the range of from about 10° C. to the boiling point of the pasting agent and normal pressure or slightly superatmospheric pressure. Thereafter, if appropriate, at least one of the compounds described above can be added. The mixture thus obtained is homogenized, preferably kneaded, until an extrudable plastic material has formed.

According to a more preferred embodiment of the invention, the homogenized mixture is molded. In the context of the present invention, those processes in which the molding is effected by extrusion in conventional extruders, for example to give extrudates having a diameter of preferably from 1 to 10 mm, particularly preferably from 2 to 5 mm, are preferred for the shaping processes. Such extrusion apparatuses are described, for example, in Ullmann's Enzyklopädie der Technischen Chemie, 4th Edition, Vol. 2, page 295 et seq., 1972. In addition to the use of a screw-type extruder, a plunger-type extruder is also preferably used for the molding. In principle, however, all known and/or suitable kneading and molding apparatuses and processes may be used for the shaping. Examples of these are inter alia: briquetting, i.e. mechanical compression with or without addition of additional binder material; pelleting, i.e. compacting by circular and/or rotational movements; sintering, i.e. the material to be molded is subjected to a thermal treatment. The shape of the moldings produced according to the invention can be chosen as desired. In particular, inter alia spheres, oval shapes, cylinders or tablets are possible.

In the context of the present invention, step (III) is preferably followed by at least one drying step.

In the context of the present invention, the step (IV) is preferably followed by at least one calcination step. The calcination is carried out at temperatures in the range of, in general, from 300 to 700° C., preferably from 400 to 600° C. The calcination can be effected under any suitable gas atmosphere, air and/or lean air being preferred. Furthermore, the calcination is preferably carried out in a muffle furnace, a rotary kiln and/or a belt calcination oven. It is possible for the temperatures during a calcination step to remain constant or to be changed continuously or discontinuously. If calcination is effected twice or more often, the calcination temperatures can be different or identical in the individual steps.

Accordingly, the present invention also relates to a process for the production of a molding as described above, comprising the steps (I) preparing of a mixture containing the at least one pillared silicate compound as described above, and optionally at least one binder;

(II) kneading of the mixture;

(III) molding of the kneaded mixture to give at least one molding;

(IV) drying of the at least one molding;

(V) calcining of the at least one dried molding.

Before and/or after the drying and/or before and/or after the calcination, the at least one molding can, if appropriate, be treated with a concentrated or dilute Broenstedt acid or a mixture of two or more Broenstedt acids. Suitable acids are, for example, hydrochloric acid, sulfuric acid, phosphoric acid, nitric acid or carboxylic acids, dicarboxylic acids or oligo- or polycarboxylic acids, such as nitrilotriacetic acid, sulfosalicylic acid or ethylenediaminetetraacetic acid. If appropriate, this at least one treatment with at least one Broenstedt acid is followed by at least one drying step and/or at least one calcination step, which in each case is carried out under the conditions described above.

According to a further embodiment of the process of the present invention, the moldings obtained according to the invention can, for better hardening, be subjected to a water steam treatment, after which preferably drying is effected at least once again and/or calcination is effected at least once again. For example, after at least one drying step and at least one subsequent calcination step, the calcined molding is subjected to the steam treatment and is then dried at least once again and/or calcined at least once again.

Finally, the present invention relates to the use of a pillared silicate compound as defined in the foregoing and/or which is obtainable or obtained according to a process for the preparation of a pillared silicate compound as defined in the foregoing, as a molecular sieve, catalyst, catalyst component, catalyst support or binder thereof, as absorbents, for ion exchange, for the production of ceramics, and/or in polymers. According to the present invention, the pillared silicate compound is preferably used as a catalyst.

The present invention is explained in more detail with reference to the examples and figures described below.

The powder X-ray diffraction patterns displayed in the figures were recorded on a Siemens D-5000 with monochromatic Cu Kα-1 radiation, a capillary sample holder being used in order to avoid a preferred orientation. The diffraction data was collected using a position-sensitive detector from Braun, in the range of from 8 to 96° (2 theta) and with a step width of 0.0678 degrees. Indexing of the powder diagram was effected using the program Treor 90, implemented in powder-X (Treor 90 is a public domain program which is freely accessible via the URL http://www.ch.iucr.org/sincris-top/logiciel/). In the figures, the angle 2 theta in degrees is shown along the abscissa and the intensities are plotted along the ordinate.

The nitrogen adsorption isotherms displayed in the figures were determined according to DIN 66134 at 77K. In the figures, the relative pressure $P/P_0$ is plotted along the abscissa and the pore volume in ml/g at standard pressure and temperature (STP) is plotted along the ordinate.

EXAMPLES

Example 1

Preparation of a Pillared Silicate Compound 651.6 g of aqueous diethyldimethylammonium hydroxide (20.62 wt.-%) solution were weighed into a beaker, to which 136.5 g of amorphous silica (Aerosil® 200) were added in portions and the mixture was stirred for 2 h, affording a yellowish suspension. 107.8 g of water were then removed from the resulting mixture using a rotary evaporator, and the concentrated mixture was stirred for 30 min. 135.3 g of the mixture were then weighed into a pressure digestion vessel and then heated therein under hydrothermal conditions at 140° C. for 19 days (456 h), thus affording a silvery-white shimmering suspension.

The resulting suspension was then separated by centrifugation and dried at 120° C. for 72 h, thus affording 27.1 g of RUB-36. The maximum peak (100% intensity) in the X-ray diffraction pattern of the RUB-36 sample was found at 7.95° 2 theta when using the Cu K(alpha 1) wavelength.

50.2 g of 1M hydrochloric acid and 2.8 g of RUB-36 were placed in a Teflon cup. The mixture was then stirred for 5 min after which 0.7 g of $TiCl_3$ were then added under stirring. The mixture was then stirred for an additional 15 min. The Teflon cup was then sealed shut and placed in an autoclave, where the vessel was heated to 170° C. and held at that temperature for 24 h.

The resulting mixture was filtered on a glass frit and washed with a total of 1.75 l of distilled water such that the washing water achieved a neutral pH. The obtained solid was then dried at 120° C. for 6 h, after which it was then calcined by heating to 500° C. at a rate of 1° C./min and holding the temperature at 500° C. for 6 h, thus obtaining 2.65 g of a white powder.

As may be taken from the XRD displayed in FIG. 1, compared to the RUB-36 structure, the 2 theta value of the most intense reflection is shifted to the left. Exact analysis of said reflection indicates a shift of 0.34° 2 theta to 7.61° 2 theta, thus indicating interlayer expansion of the RUB-36 structure due to titanium bridging between the silicate layers of the layered silicate structure.

The freshly calcined sample obtained according to Example 1 was degassed over night at 120° C. and a reduced pressure of about $10^{-6}$ mPa. The sample was then evaluated with respect to nitrogen adsorption at 77 k on a volumetric sorption apparatus (Autosorb AS-6, from Quantachrome) for obtaining the adsorption isotherm thereof according to DIN 66135. Evaluation of the data gave a BET surface area of 331 $m^2/g$ and a surface area of 436 $m^2/g$ according to the Langmuir method.

Example 2

Preparation of Pillared RUB-36 using $TiCl_4$

A pillared RUB-36 silicate compound was prepared according to the procedure in Example 1 using 0.9 g of $TiCl_4$ instead of $TiCl_3$, to obtain 2.47 g of a white powder.

The X-ray diffraction pattern of the obtained pillared silicate compound displayed its highest intensity reflection at a 2 theta angle of 7.95°, thus indicating a shift of 0.36° 2 theta relative to the RUB-36 precursor compound due to titanium bridging between the silicate layers of the layered silicate structure.

The adsorption isotherm for the sample was measured according to Example 1, affording a BET surface area of 352 $m^2/g$ and an equivalent surface of 464 $m^2/g$ according to the Langmuir method.

Example 3

Preparation of a Pillared RUB-36 Silicate Using Tetra-n-butyl Orthotitanate 651.6 g of aqueous diethyldimethylammonium hydroxide (20.62 wt.-%) solution were weighed into a beaker, to which 136.5 g of amorphous silica (Aerosil® 200) were added in portions and the mixture was stirred for 2 h, affording a yellowish suspension. 107.8 g of water were then removed from the resulting mixture using a rotary evaporator, and the concentrated mixture was stirred for 30 min. 169.0 g of the mixture were then weighed into a pressure digestion vessel and then heated therein under hydrothermal conditions at 140° C. for 14 days (336 h), thus affording a silvery-white shimmering suspension.

The resulting suspension was then separated by centrifugation and dried at 120° C. for 72 h, thus affording 32.6 g of RUB-36. The maximum peak (100% intensity) in the X-ray diffraction pattern of the RUB-36 sample was found at 7.95° 2 theta when using the Cu K(alpha 1) wavelength.

4.9 g of nitric acid (65%), 163.2 g of distilled water, and 2.8 g of the RUB-36 were placed in a Teflon cup. The mixture was then stirred for 5 min after which 1.2 g of tetra-n-butyl orthotitanate were then added under stirring. The mixture was then stirred for an additional 15 min. The Teflon cup was then sealed shut and placed in an autoclave, where the vessel was heated to 170° C. and held at that temperature for 24 h.

The resulting mixture was filtered on a glass frit and washed with a total of 21 of distilled water such that the washing water achieved a neutral pH. The obtained solid was then dried at 120° C. for 6 h, after which it was then calcined by heating to 500° C. at a rate of 1° C./min and holding the temperature at 500° C. for 6 h, thus obtaining 2.27 g of a white powder.

Figure 2:
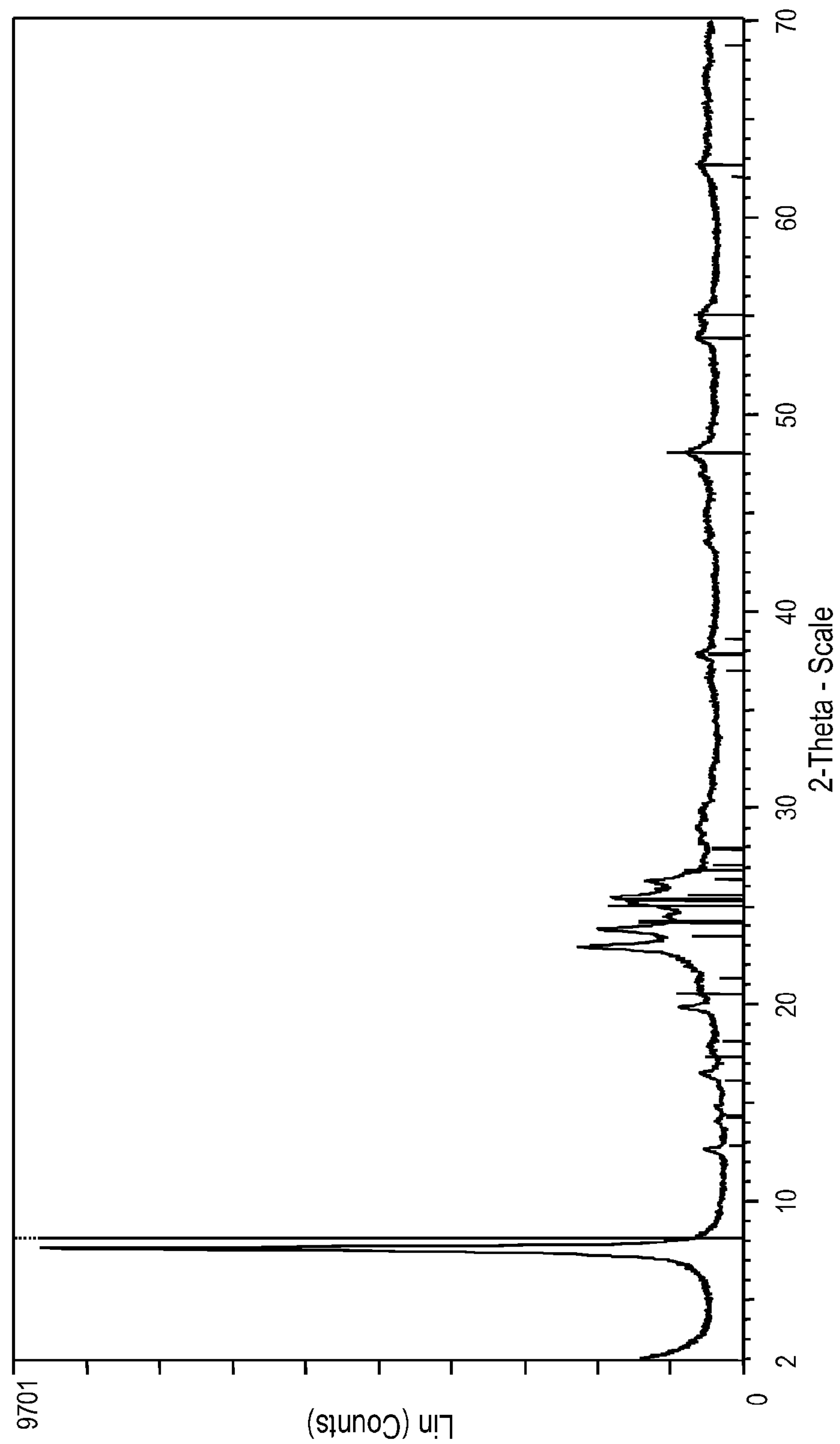
FIG. 2 shows the X-ray diffraction pattern of the pillared silicate compound obtained according to Example 3. Said figure further includes the line patterns of the RUB-36 structure and of anatase, respectively, for comparison.

As may be taken from the X-ray diffraction pattern obtained for the pillared silicate compound of Example 3 which is displayed in FIG. 2, the highest intensity reflection is shifted to lower 2 theta values compared to RUB-36, thus indicating interlayer expansion via titanium bridging. A closer analysis of the highest intensity reflection affords a 2 theta value of 7.61°, thus indicating a shift of 0.34° 2 theta with respect to RUB-36.

Example 4

Preparation of a Pillared RUB-36 Silicate Using Tetraethyl Orthotitanate

A pillared silicate compound was prepared using the procedure of Example 3 using 0.8 g of tetraethyl orthotitanate instead of tetra-n-butyl orthotitanate, thus obtaining 2.16 g of a white powder.

Figure 3:
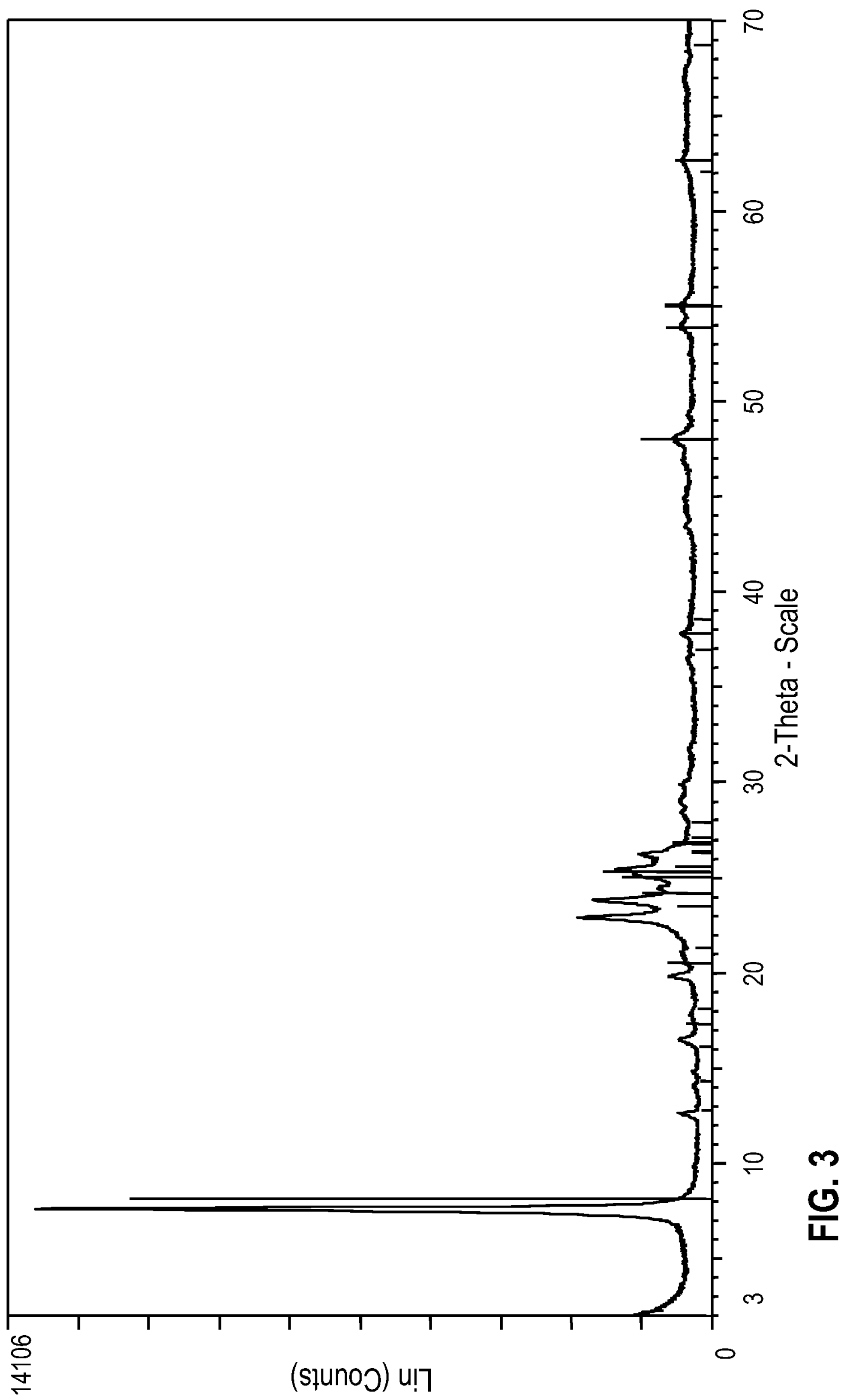
FIG. 3 shows the X-ray diffraction pattern of the pillared silicate compound obtained according to Example 4. Said figure further includes the line patterns of the RUB-36 structure and anatase, respectively, for comparison.

As may be taken from the X-ray diffraction pattern obtained for the pillared silicate compound of Example 4 which is displayed in FIG. 3, the highest intensity reflection is shifted towards lower 2 theta values, thus indicating interlayer expansion via titanium bridging. A closer analysis of the X-ray diffraction data affords a 2 theta value of the highest intensity reflection of 7.58°, which corresponds to a shift of 0.37° 2 theta relative to the highest intensity reflection of the RUB-36 precursor compound.

Example 5

Preparation of a Pillared RUB-36 Silicate Using $ZrCl_4$

A pillared silicate compound was obtained according to the procedure of Example 1 using 1.1 g of $ZrCl_4$ instead of $TiCl_3$, thus affording 2.83 g of a white powder.

Figure 4:
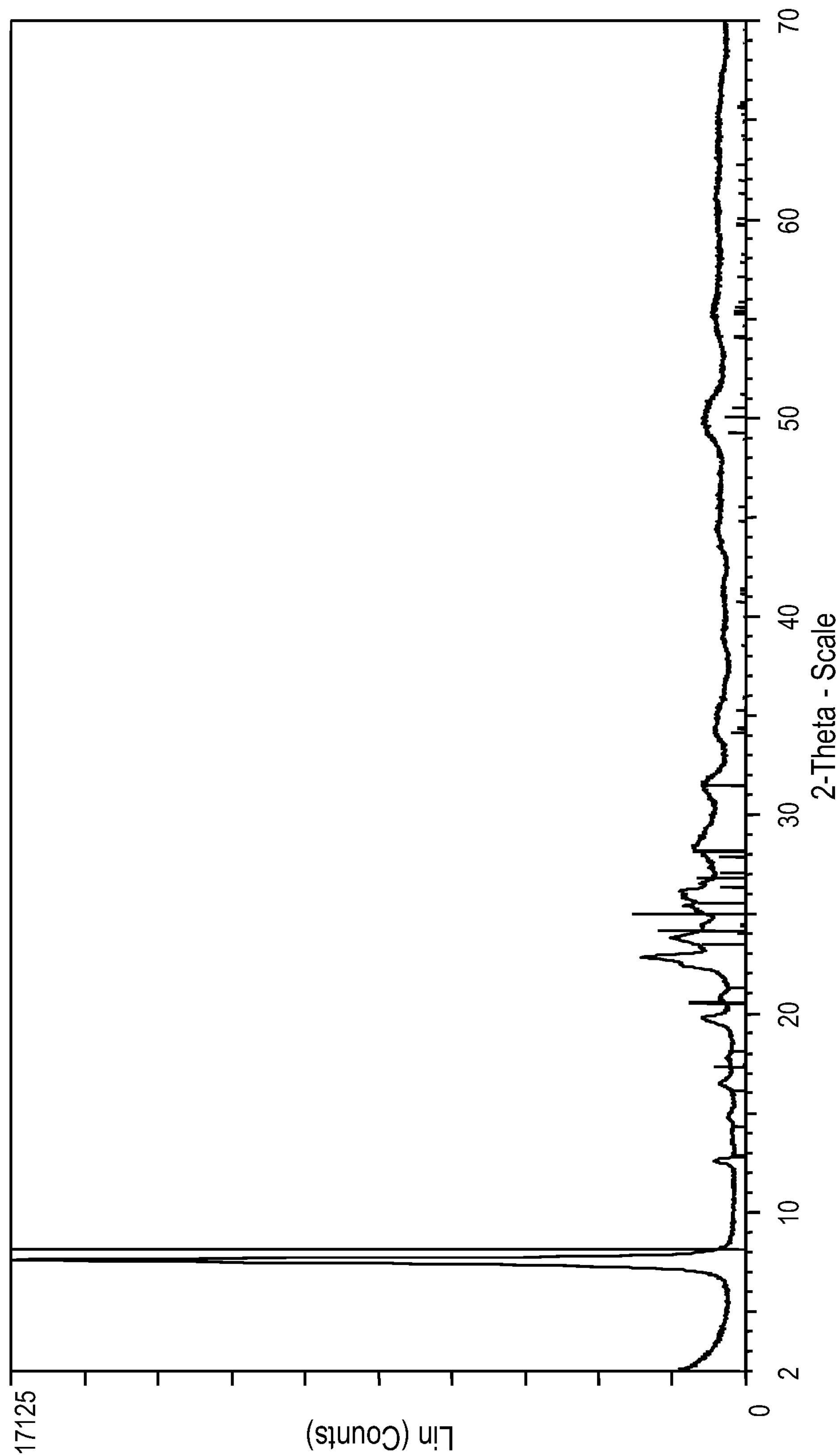
FIG. 4 shows the X-ray diffraction pattern of the pillared silicate compound obtained according to Example 5. Said figure further includes the line patterns of the RUB-36 structure and of baddeleyite, respectively, for comparison.

As may be taken from the X-ray diffraction pattern obtained for the pillared silicate compound of Example 5 displayed in FIG. 4, the highest intensity reflection is shifted to lower 2 theta values relative to the RUB-36 precursor compound, thus indicating pillaring of the silicate layers via Zr-bridging. In particular, a closer analysis of the X-ray diffraction data affords a value of 7.5° 2 theta for the highest intensity reflection, thus indicating a shift of 0.37° 2 theta relative to the corresponding reflection of the RUB-36 precursor compound.

The nitrogen adsorption isotherm obtained using the sample of Example 5 according to DIN 66135 afforded a BET surface area of 317 $m^2/g$ and an equivalent surface of 419 $m^2/g$ according to the Langmuir method.

Example 6

Preparation of a Pillared RUB-36 Silicate Using Manganese Dichloride 1628.2 g of aqueous diethyldimethylammonium hydroxide (20.62 wt.-%) solution were weighed into a beaker, to which 341.2 g of amorphous silica (Aerosil® 200) were added in portions and the mixture was stirred for 2 h, affording a yellowish suspension. 281.5 g of water were then removed from the resulting mixture using a rotary evaporator, and the concentrated mixture was stirred for 1 h. The mixture was then transferred to a pressure digestion vessel and then heated therein under hydrothermal conditions at 140° C. for 8 days (192 h), thus affording a silvery-white shimmering suspension.

The resulting suspension was then separated by filtration, washed with the mother liquor and subsequently with 9 l of distilled water, after which the solid residue was dried at 120° C. for 24 h, thus affording 254.6 g of RUB-36. The maximum peak (100% intensity) in the X-ray diffraction pattern of the RUB-36 sample was found at 7.92° 2 theta when using the Cu K(alpha 1) wavelength.

A pillared silicate compound was then obtained using the procedure of Example 1, wherein RUB-36 according to the present example was used, and wherein 0.6 g of $MnCl_2$ were used instead of $TiCl_3$, thus affording 2.18 g of a white powder.

Figure 5:
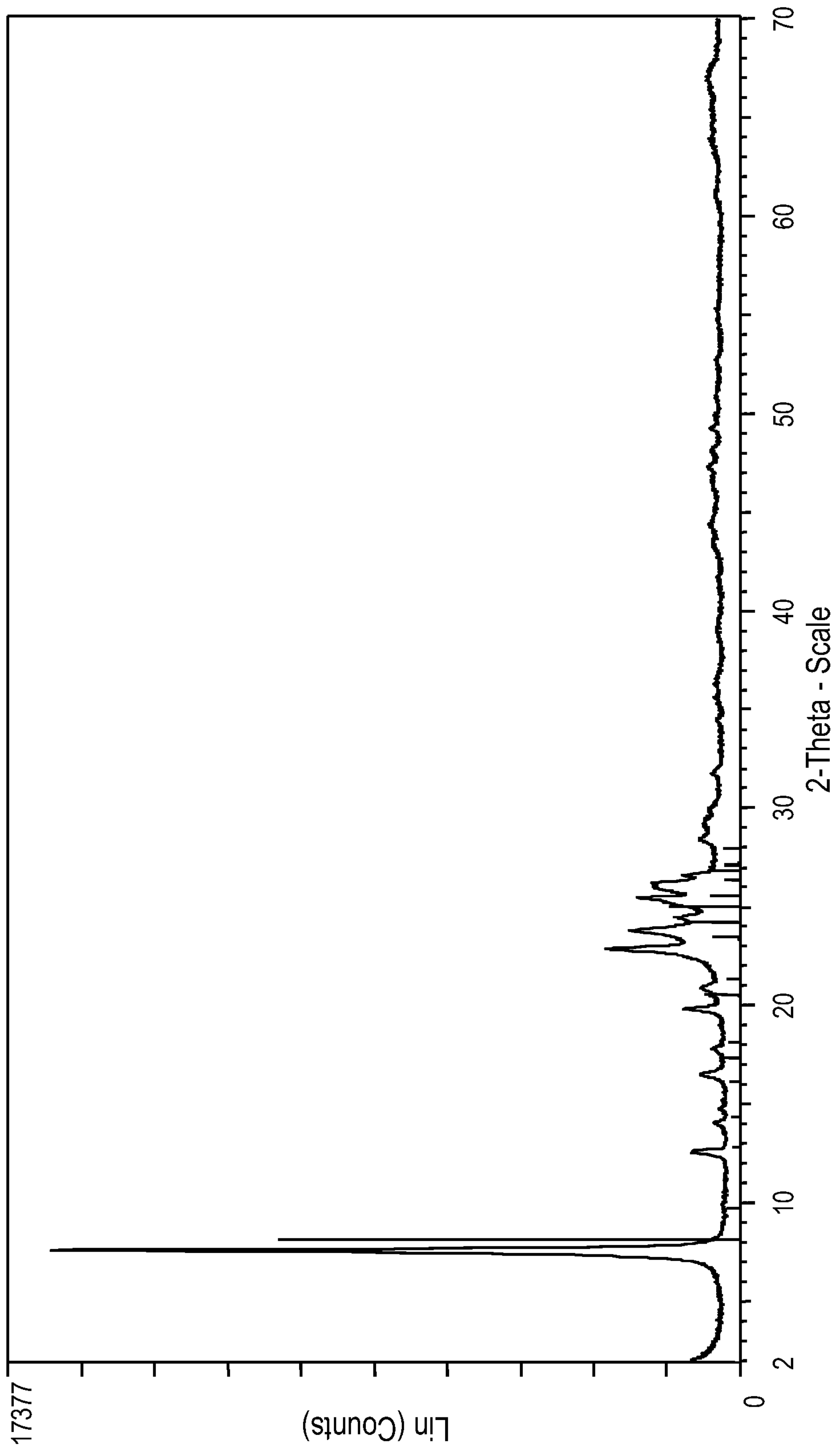
FIG. 5 shows the X-ray diffraction pattern of the pillared silicate compound obtained according to Example 6. Said figure further includes the line patterns of the RUB-36 and of the RUB-37 structures, respectively, for comparison.

As may be taken from the X-ray diffraction pattern obtained for the sample of Example 6 displayed in FIG. 5, the highest intensity reflection is shifted towards lower 2 theta values relative to the RUB-36 precursor compound, thus indicating interlayer expansion via manganese bridging between the silicate layers of the layered silicate structure. In particular, a value of 7.58° 2 theta is obtained for said reflection, indicating a shift of 0.34° 2 theta relative to the RUB-36 precursor compound.

Figure 6:
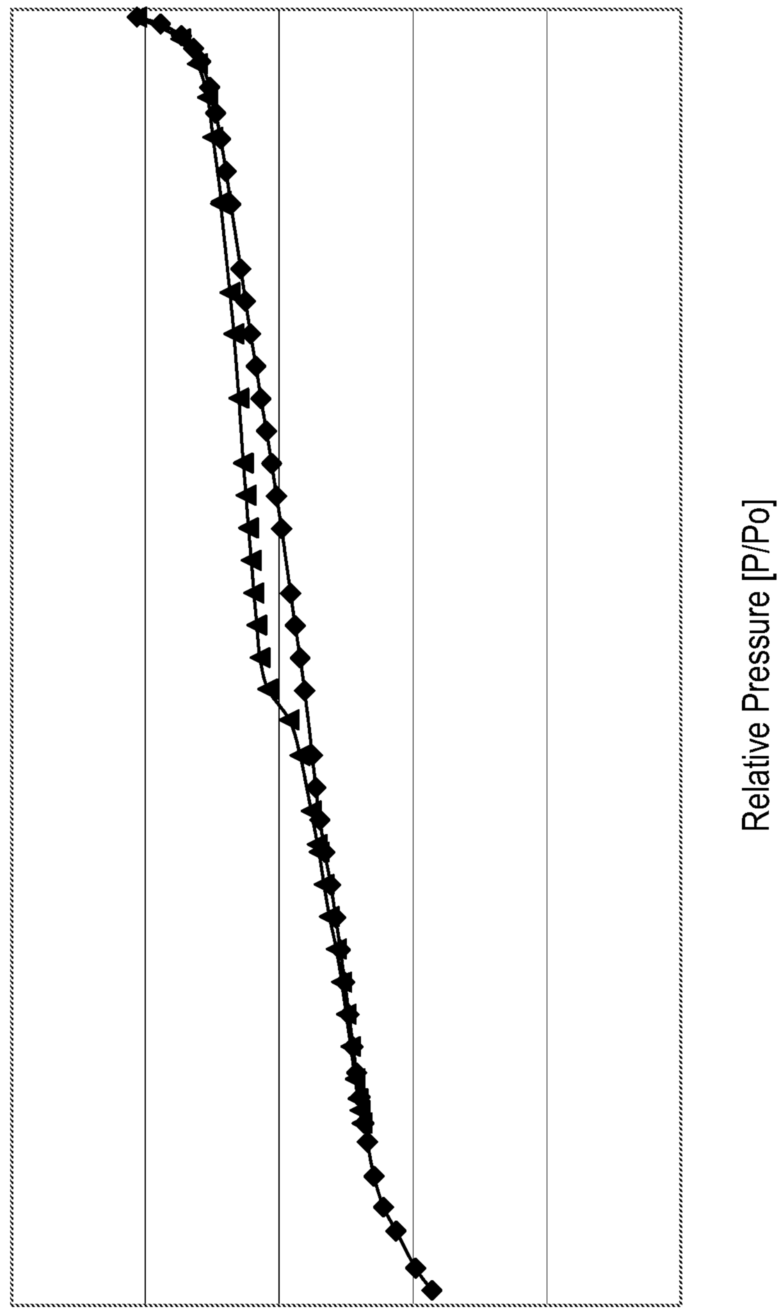
FIG. 6 shows the nitrogen adsorption isotherms obtained for the pillared silicate compound obtained according to Example 6. Said figure further includes the line patterns of the RUB-36 structure and of baddeleyiete, respectively, for comparison.

The nitrogen adsorption isotherm obtained for the sample of Example 6 is displayed in FIG. 6, wherein the evaluation according to DIN 66135 affords a BET surface area of 425 $m^2/g$.

Example 7

Preparation of a Pillared RUB-36 Silicate Using $Mn(acac)_3$

A pillared silicate compound was prepared using the procedure of Example 3, using RUB-36 obtained according to Example 6, and using 1.6 g of manganese(III) 2,4-pentanedionate instead of tetra-n-butyl orthotitanate, thus obtaining 2.11 g of a white powder.

Figure 7:
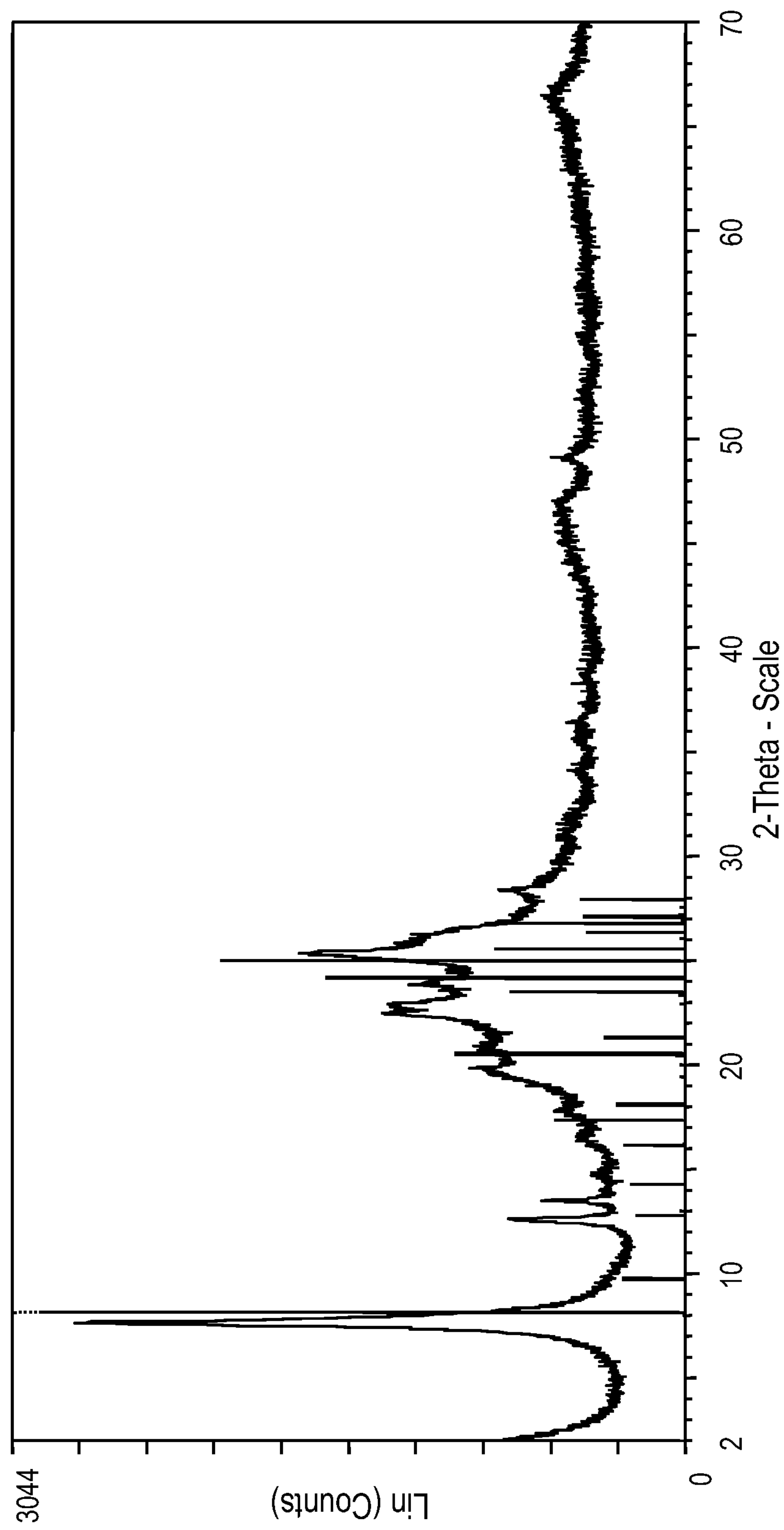
FIG. 7 shows the X-ray diffraction pattern of the pillared silicate compound obtained according to Example 7. Said figure further includes the line patterns of the FIG. 8 shows the X-ray diffraction pattern for the pillared silicate compound obtained from Example 8. Said figure further includes the line pattern of the RUB-36 structure for comparison.

As may be taken from the X-ray diffraction pattern obtained for the sample of Example 7 displayed in FIG. 7, the highest intensity reflection is shifted towards lower 2 theta values, thus indicating interlayer expansion due to bridging of the silicate layers by manganese. In particular, a closer analysis reveals a 2 theta value of 7.62° 2 for said reflection, corresponding to a shift of 0.30° 2 theta

Comparative Example 1

The procedure of Example 6 was repeated without adding any hydrochloric acid, thus affording 2.21 g of a brown powder.

X-ray diffraction of the sample obtained according to Comparative Example 1 revealed a highly amorphous product. Accordingly, the pH of the reaction mixture appears to be essential for producing a pillared silicate compound according to the present invention. In particular, conducting the reaction procedure at a pH outside the inventive range may even lead to complete disintegration of the layered silicate precursor as observed in the present comparative example.

Example 8

Preparation of a Pillared RUB-36 Silicate Using Iron(II) Chloride

A pillared silicate compound was synthesized using the procedure according to Example 1, wherein 0.9 g of $FeCl_2.4H_2O$ were used instead of $TiCl_3$, thus affording 1.85 g of a white powder.

Figure 8:
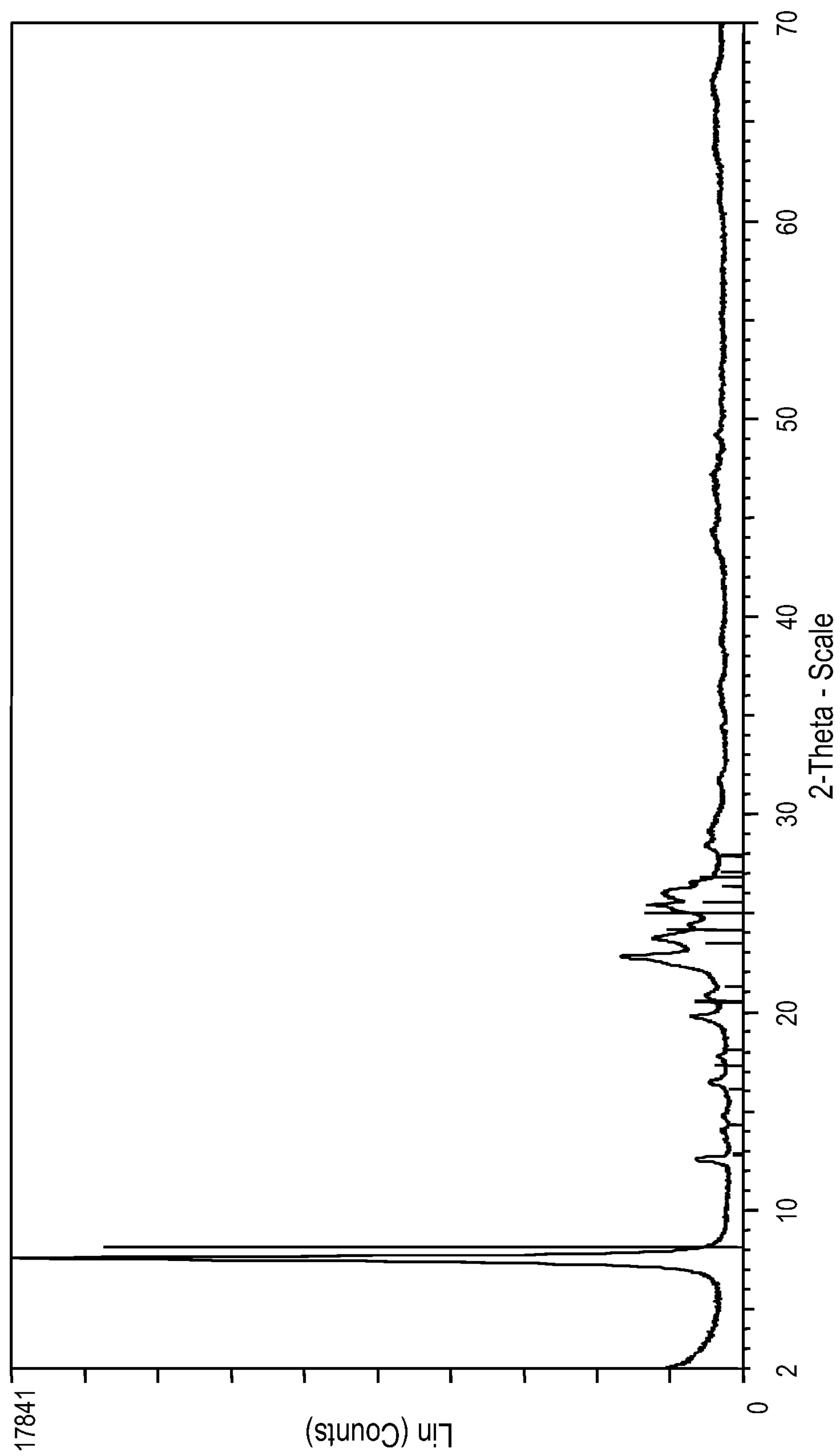

As may be taken from the X-ray diffraction pattern obtained for the sample of Example 8 displayed in FIG. 8, the 2 theta value of the highest intensity reflection is shifted towards lower 2 theta values compared to the highest intensity reflection of the RUB-36 precursor compound. In particular, a closer analysis reveals a 2 theta value of 7.55° 2 for said reflection, corresponding to a shift of 0.4° 2 theta.

The nitrogen adsorption isotherm obtained using the sample of Example 8 according to DIN 66135 afforded a BET surface area of 375 $m^2/g$ and an equivalent surface of 494 $m^2/g$ according to the Langmuir method.

Example 9

Preparation of a Pillared RUB-36 Silicate Using Iron(III) Chloride

A pillared silicate compound was obtained using the procedure of Example 1, wherein 1.2 g of $FeCl_3.6H_2O$ were used instead of $TiCl_3$, thus affording 2.213 g of a light brown powder.

X-ray diffraction performed on a sample obtained according to Example 9 revealed a 2 theta value for the highest intensity reflection of 7.55°, thus corresponding to the results obtained for Example 8.

The nitrogen adsorption isotherm obtained for said example according to DIN 66135 afforded a BET surface area of 409 $m^2/g$ and an equivalent surface of 538 $m^2/g$ according to the Langmuir method.

Example 10

Preparation of a Pillared RUB-36 Silicate Using Europium(III) Chloride

A pillared silicate compound was obtained according to the procedure described in Example 1, wherein RUB-36 obtained according to Example 6 was used, and wherein 1.7 g of $EuCl_3.6H_2O$ was used instead of $TiCl_3$, thus affording 2.04 g of a white powder.

Figure 9:
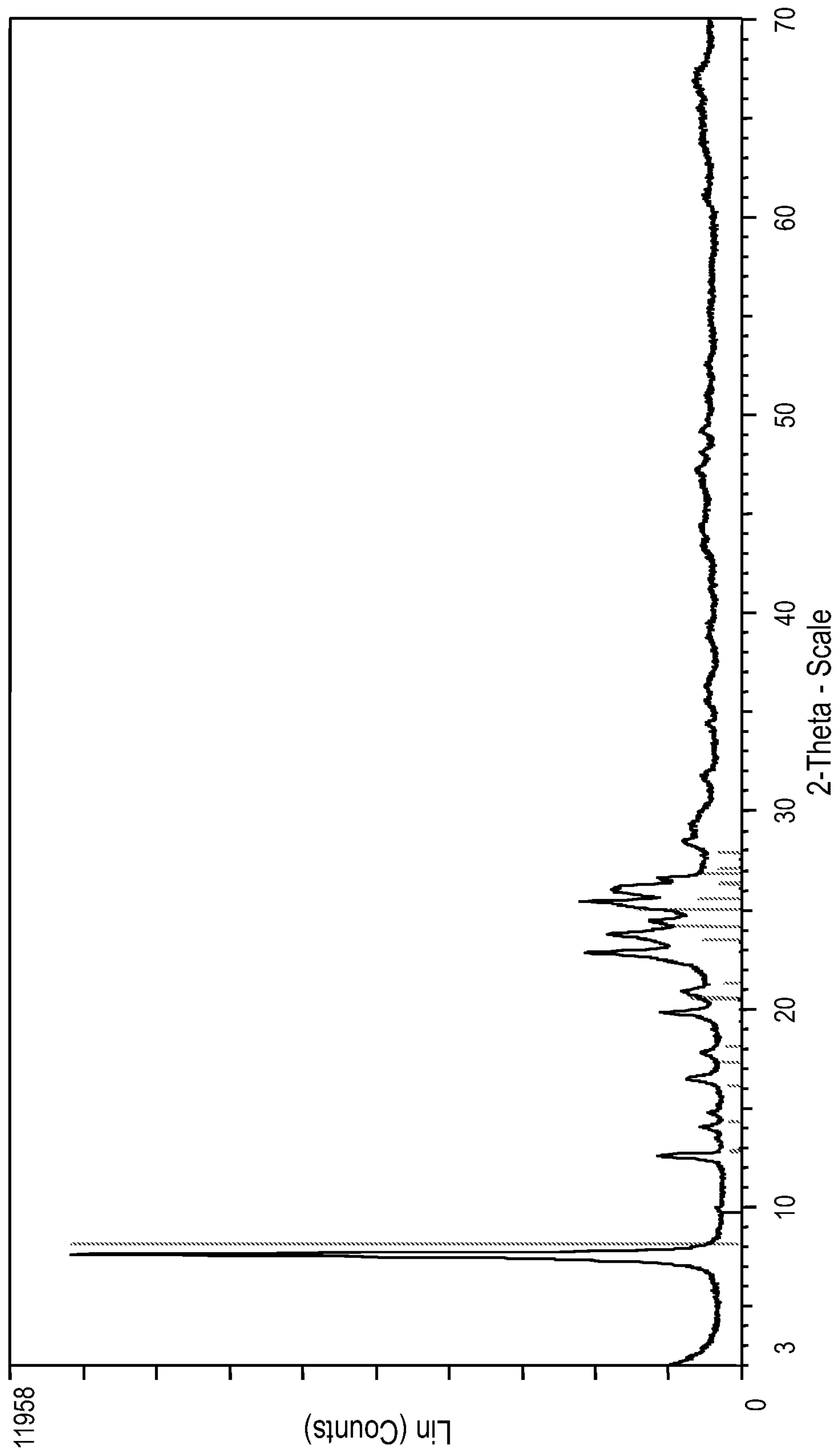
FIG. 9 shows the X-ray diffraction pattern for the pillared silicate compound obtained from Example 10. Said figure further includes the line patterns of the RUB-36 and of the RUB-37 structures, respectively, for comparison.

As may be taken from the X-ray diffraction pattern of the sample of Example 10 displayed in FIG. 9, the highest intensity reflection is shifted towards lower 2 theta values relative to the RUB-36 precursor compound, thus indicating interlayer expansion via bridging with europium. In particular, a value of 7.58° 2 theta is obtained for said reflection, corresponding to a shift of 0.34° 2 theta relative to RUB-36.

Figure 10:
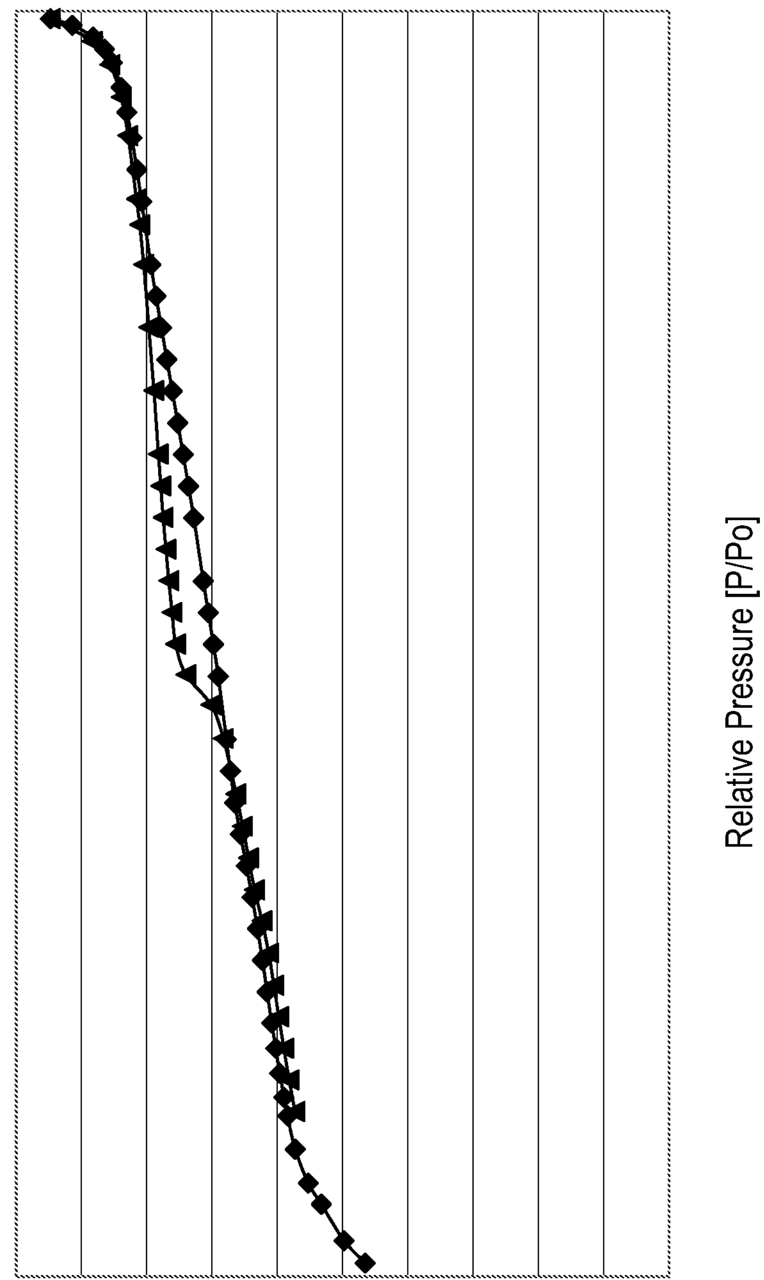
FIG. 10 shows the nitrogen adsorption isotherm obtained for the pillared silicate compound according to Example 10.

The nitrogen adsorption isotherm obtained for the sample of Example 10 is displayed in FIG. 10, wherein according to DIN 66135 a BET surface area of 422 $m^2/g$ and an equivalent surface of 560 $m^2/g$ according to the Langmuir method are respectively obtained.

Example 11

Preparation of a Pillared RUB-36 Silicate Using Iron(III) Chloride 50.2 g of 1M hydrochloric acid and 2.8 g of RUB-36 obtained according to Example 6 were placed in a Teflon cup. The mixture was then stirred for 10 min after which 1.2 g of $FeCl_3.6H_2O$ were then added under stirring. The mixture was then stirred for an additional 10 min. The Teflon cup was then sealed shut and placed in an autoclave, where the vessel was heated to 150° C. and held at that temperature for 24 h.

The resulting mixture was filtered on a glass frit and washed with a total of 5 l of distilled water such that the washing water achieved a neutral pH. The obtained solid was then dried at 120° C. for 16 h, after which it was then calcined by heating to 500° C. at a rate of 1° C./min and holding the temperature at 500° C. for 6 h, thus obtaining 2.4 g of a white powder.

Figure 11:
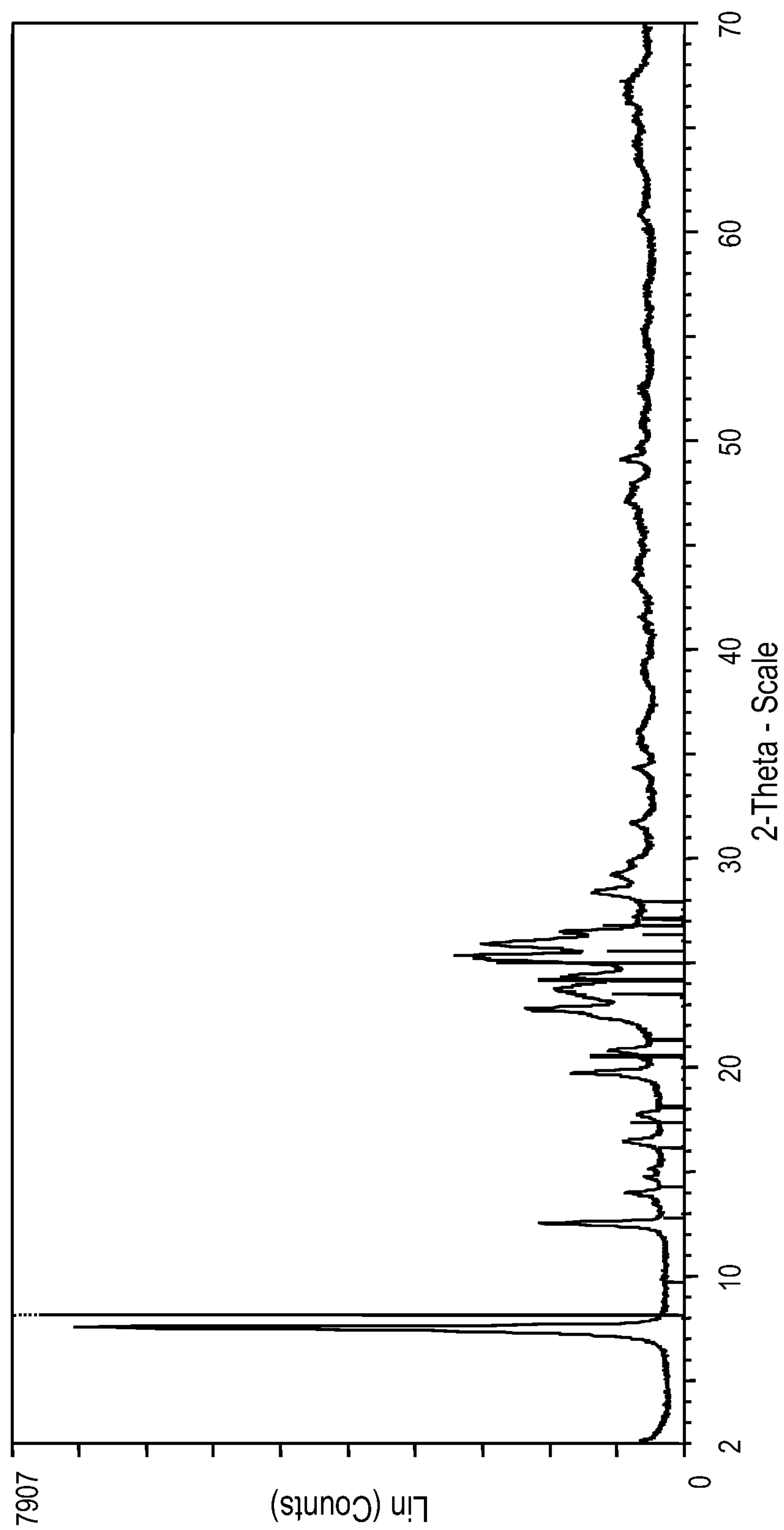
FIG. 11 shows the X-ray diffraction pattern obtained for the pillared silicate compound according to Example 11. The figure further includes the line patterns of the RUB-36 and of the RUB-37 structures, respectively, for comparison.
Figure 12:
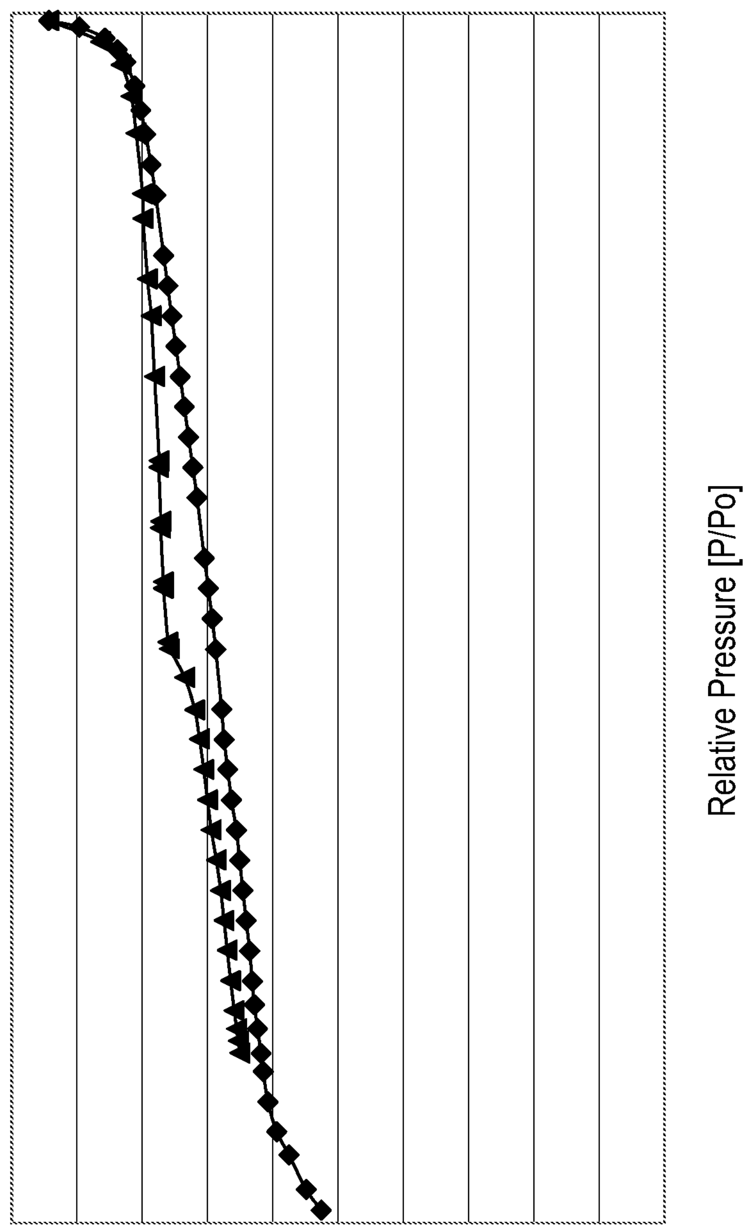
FIG. 12 shows the nitrogen adsorption isotherm obtained for the pillared silicate compound according to Example 11.

As may be taken from the X-ray diffraction pattern obtained for the sample of Example 11 displayed in FIG. 11, the highest intensity reflection is shifted towards lower 2 theta values relative to the RUB-36 precursor compound, thus indicating interlayer expansion via the presence of iron bridging between the silicate layers. As revealed by a closer analysis of the diffraction data, the highest intensity reflection has a 2 theta value of 7.56°, indicating a shift of 0.36° 2 theta relative to the RUB-36 precursor compound.

The nitrogen adsorption isotherm obtained for the sample of Example 11 reveals a BET surface area of 433 $m^2/g$ and an equivalent surface of 571 $m^2/g$ according to the Langmuir method.

Example 12

Preparation of a Pillared RUB-36 Silicate Using Ruthenium(III) Chloride

A pillared silicate compound was prepared using the procedure of Example 1, wherein 1.3 g of ruthenium(III) chloride hydrate were used instead of $TiCl_3$, thus affording 2.63 g of a black-gray powder.

As revealed by X-ray powder diffraction of the resulting sample, the highest intensity reflection appears at 2 theta values of 7.58°, thus indicating a shift of 0.39° 2 theta relative to the RUB-36 precursor compound as a result of interlayer expansion via ruthenium bridging of the silicate layers. As further revealed by X-ray diffraction, however, said sample apparently contains ruthenium oxide impurities.

The nitrogen adsorption isotherm obtained for the sample of Example 12 according to DIN 66135 reveals a BET surface area of 322 $m^2/g$ and an equivalent surface of 427 $m^2/g$ according to the Langmuir method.

Example 13

Preparation of a Pillared RUB-36 Silicate Using Cobalt(II) Chloride

A pillared silicate compound was prepared according to the method described in Example 1, wherein 1.1 g of $COCl_2.6H_2O$ were used instead of $TiCl_3$, thus affording 2.00 g of a white powder.

Figure 13:
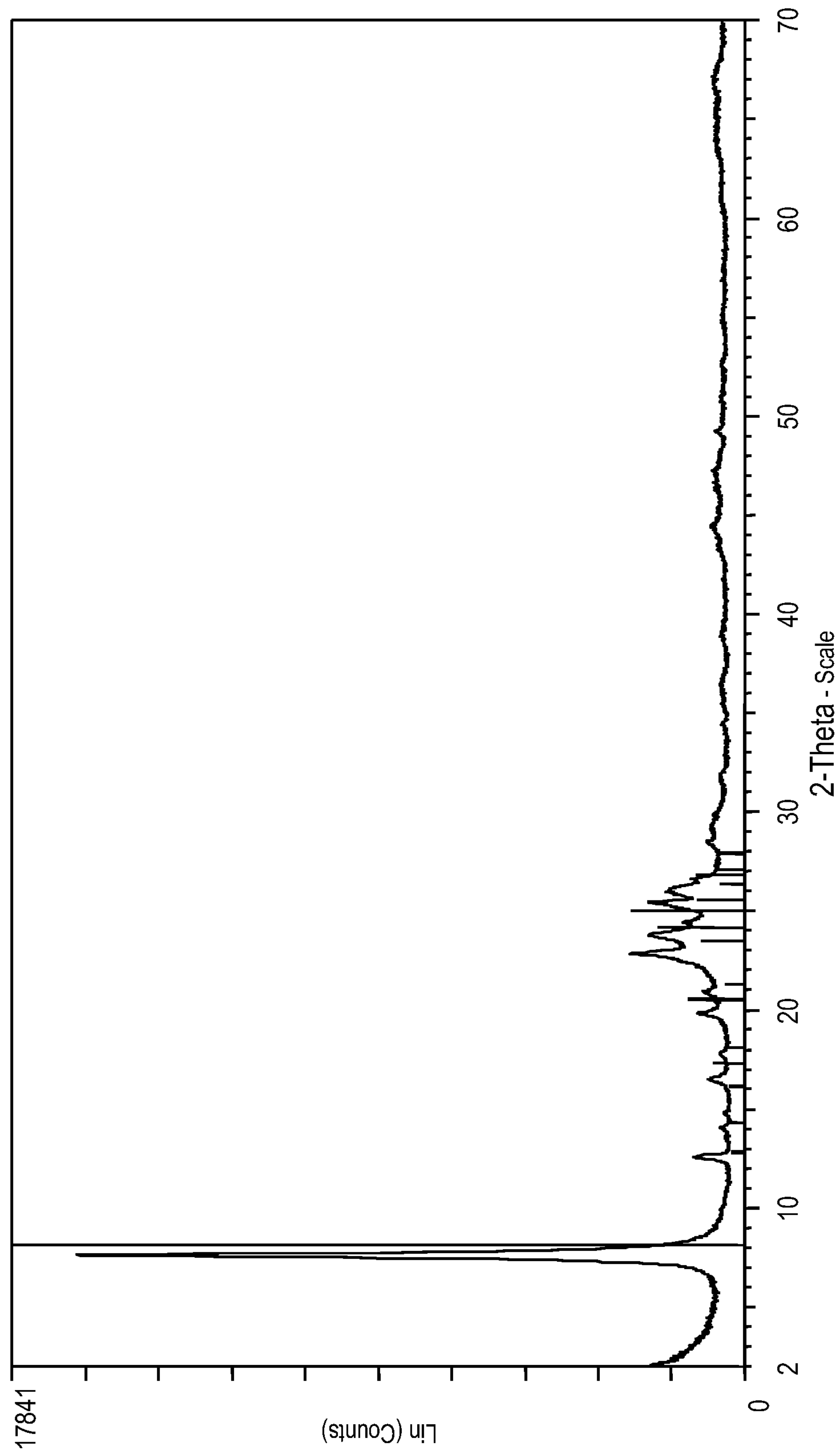
FIG. 13 shows the X-ray diffraction pattern of the pillared silicate compound obtained according to Example 13. Said figure further includes the line pattern of the RUB-36 structure for comparison.

As may be taken from the X-ray diffraction patterns obtained for the sample of Example 13 displayed in FIG. 13, the highest intensity reflection is shifted towards lower 2 theta values compared to the RUB-36 precursor compound, thus indicating interlayer expansion via cobalt bridging between the silicate layers. A closer analysis of the X-ray diffraction data reveals a 2 theta value of 7.60° for the highest intensity reflection, thus indicating a shift of 0.35° 2 theta relative to RUB-36.

The nitrogen adsorption isotherm obtained for the sample of Example 13 according to DIN 66135 affords a BET surface area of 385 $m^2/g$ and an equivalent surface of 509 $m^2/g$ according to the Langmuir method.

Example 14

Preparation of a Pillared RUB-36 Silicate Using Palladium(II) Chloride

A pillared silicate compound was obtained using the method of Example 1, wherein 0.8 g of $PdCl_2$ were used instead of $TiCl_3$, thus affording 1.95 g of a light brown powder.

Figure 14:
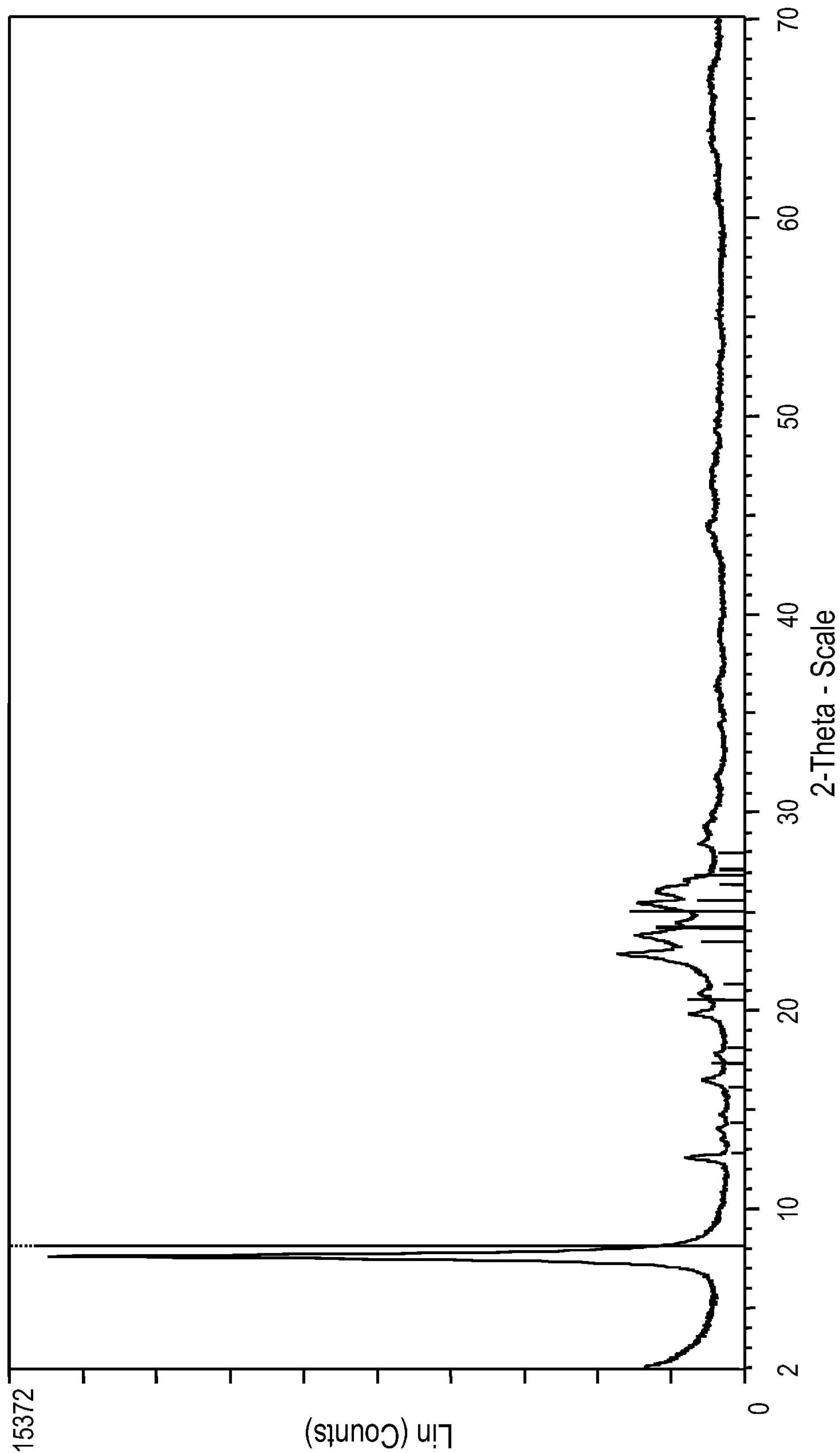
FIG. 14 shows the X-ray diffraction pattern of the pillared silicate compound obtained from Example 14. The figure further includes the line pattern of the RUB-36 structure for comparison.

As may be taken from the X-ray diffraction pattern obtained for the sample of Example 14 displayed in FIG. 14, the highest intensity reflection is shifted towards lower 2 theta values relative to the RUB-36 precursor compound. In particular, a 2 theta value of 7.58° is obtained, thus indicating a shift of 0.37° 2 theta.

The nitrogen adsorption isotherm obtained for the sample of Example 14 according to DIN 66135 affords a BET surface area of 319 $m^2/g$ and an equivalent surface of 420 $m^2/g$ according to the Langmuir method.

Example 15

Preparation of a Pillared RUB-36 Silicate Using Copper(I) Chloride 651.6 g of aqueous diethyldimethylammonium hydroxide (20.62 wt.-%) solution were weighed into a beaker, to which 136.5 g of amorphous silica (Aerosil® 200) were added in portions and the mixture was stirred for 2 h, affording a yellowish suspension. 107.8 g of water were then removed from the resulting mixture using a rotary evaporator, and the concentrated mixture was stirred for 30 min. 170.1 g of the mixture were then weighed into a pressure digestion vessel and then heated therein under hydrothermal conditions at 140° C. for 9 days (216 h), thus affording a silvery-white shimmering suspension.

The resulting suspension was then separated by centrifugation and dried at 120° C. for 72 h, thus affording 29.3 g of RUB-36. The maximum peak (100% intensity) in the X-ray diffraction pattern of the RUB-36 sample was found at 7.97° 2 theta when using the Cu K(alpha 1) wavelength.

A pillared silicate compound was then obtained according to the procedure of Example 1 using RUB-36 obtained according to the present example, and 0.6 g of CuCl instead of $TiCl_3$, thus affording 2.15 g of a white powder.

Figure 15:
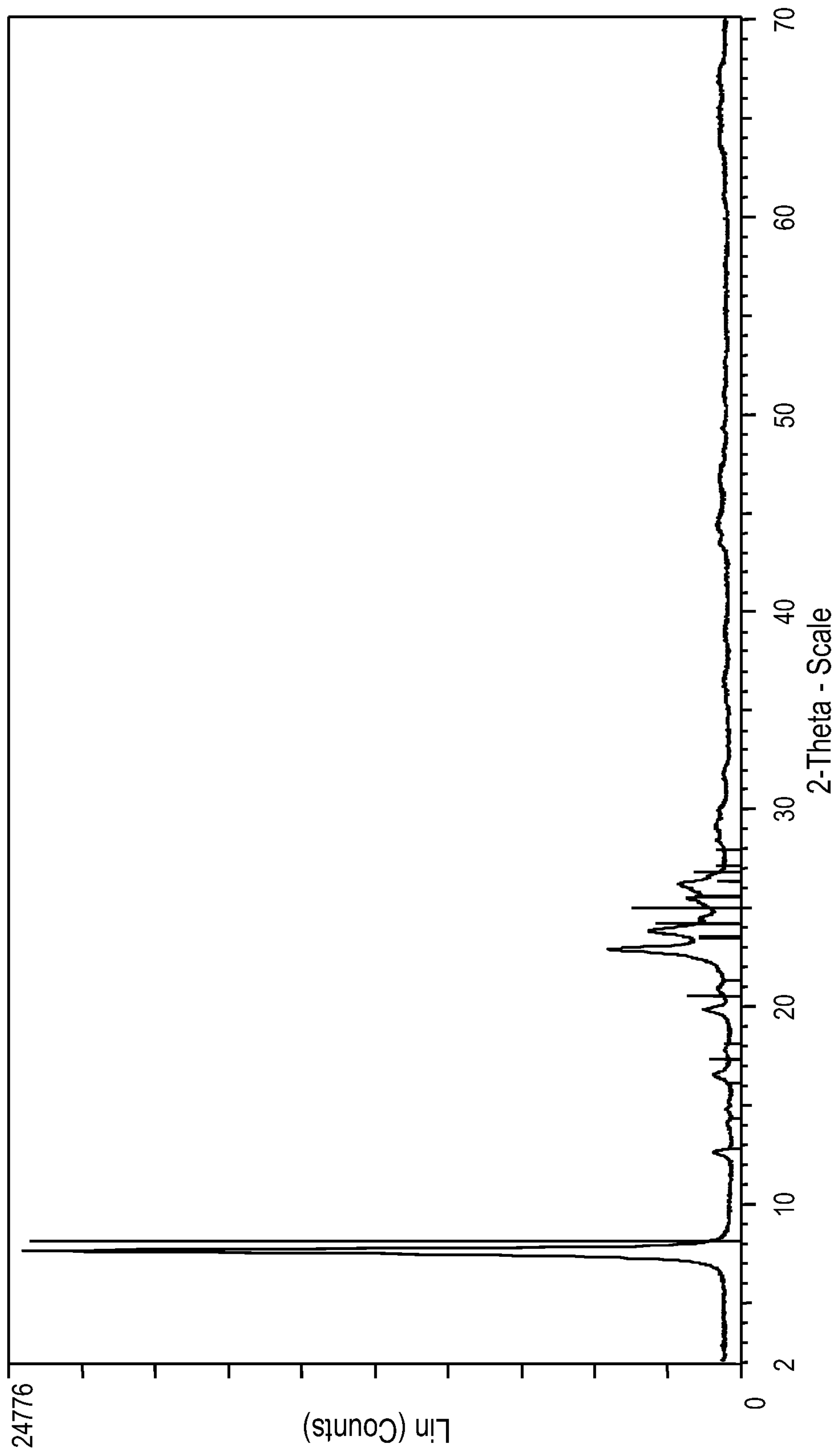
FIG. 15 shows the X-ray diffraction pattern of the pillared silicate compound obtained in Example 15. The figure further includes the line pattern of the RUB-36 structure for comparison.

As may be taken from the X-ray diffraction pattern obtained for the sample of Example 15 displayed in FIG. 15, the highest intensity reflection is shifted towards lower 2 theta values relative to the RUB-36, thus indicating interlayer expansion via bridging of the silicate layers with copper. In particular, the highest intensity reflection displays a 2 theta value of 7.62° indicating a shift of 0.35° 2 theta relative to RUB-36.

The nitrogen adsorption isotherm obtained for the sample of Example 15 according to DIN 66135 reveals a BET surface area of 363 $m^2/g$ and an equivalent surface of 476 $m^2/g$ according to the Langmuir method.

Example 16

Preparation of Pillared RUB-36 Silicate Using Copper(II) Chloride

A pillared silicate compound was obtained according to the method of Example 15, wherein 0.6 g of $CuCl_2$ were used instead of CuCl, thus affording 2.10 g of a white powder.

Figure 16:
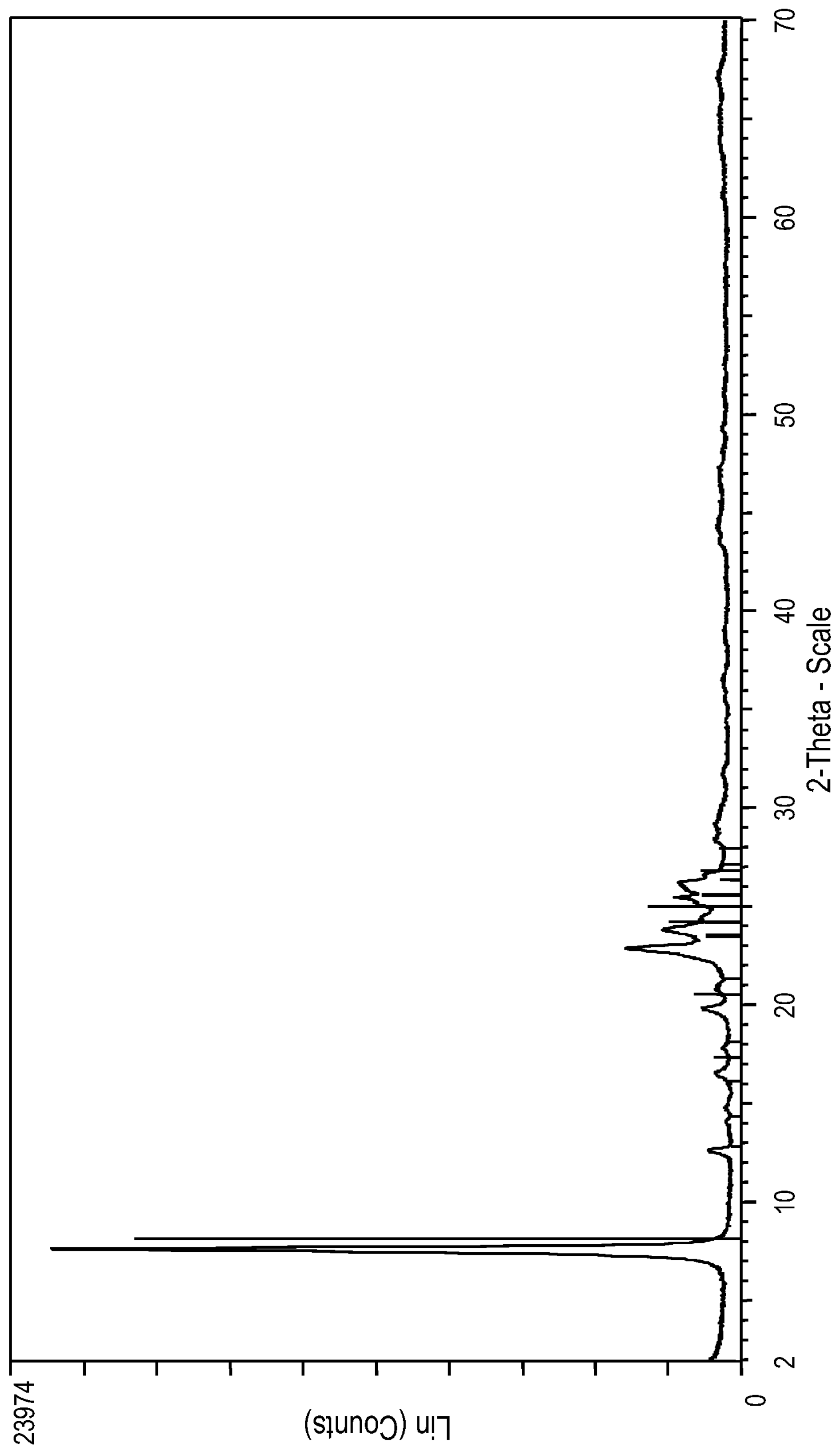
FIG. 16 shows the X-ray diffraction pattern for the pillared silicate compound of Example 16. The figure further includes the line pattern of the RUB-36 structure for comparison.

As may be taken from the X-ray diffraction pattern of the sample of Example 16 displayed in FIG. 16, the highest intensity reflection is shifted towards lower 2 theta values relative to the RUB-36 precursor compound. In particular, a value of 7.59° 2 theta is observed for said reflection, thus indicating a shift of 0.38° 2 theta relative to RUB-36.

The nitrogen adsorption isotherm obtained for the sample of Example 16 afforded a BET surface area of 366 $m^2/g$ and an equivalent surface of 481 $m^2/g$ according to the Langmuir method.

Example 17

Preparation of a Pillared RUB-36 Silicate Using Silver Chloride

A pillared silicate compound was obtained according to the method of Example 15, wherein 0.46 g of $AlCl_3$ were used instead of CuCl, thus affording 2.07 g of a white powder.

Figure 17:
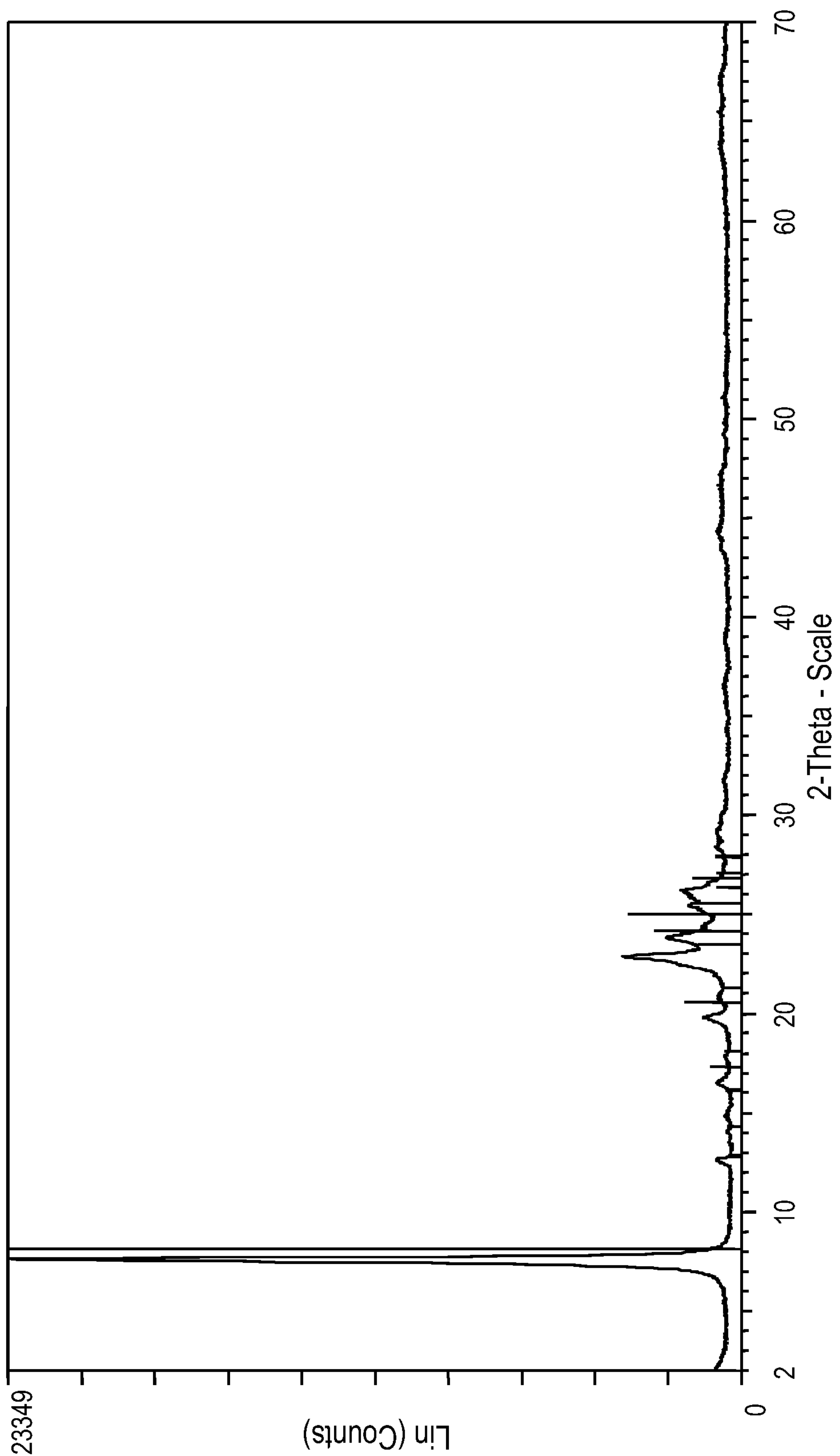
FIG. 17 shows the X-ray diffraction pattern of the pillared silicate compound obtained in Example 17. The figure further includes the line pattern of the RUB-36 structure for comparison.

As may be taken from the X-ray diffraction pattern of the sample of Example 17 displayed in FIG. 17, the highest intensity reflection is shifted towards lower 2 theta values relative to the RUB-36 precursor compound, thus indicating interlayer expansion via bridging of the silicate layers with aluminum. In particular, the highest intensity reflection is observed at a 2 theta value of 7.6°, thus indicating a shift of 0.37° 2 theta relative to RUB-36.

Example 18

Preparation of a Pillared RUB-36 Silicate Using Gold(III) Chloride

A pillared silicate compound was obtained according to the method of Example 15, wherein 0.4 g of $HAuCl_4.xH_2O$ were used instead of CuCl, thus affording 2.01 g of a white powder.

Figure 18:
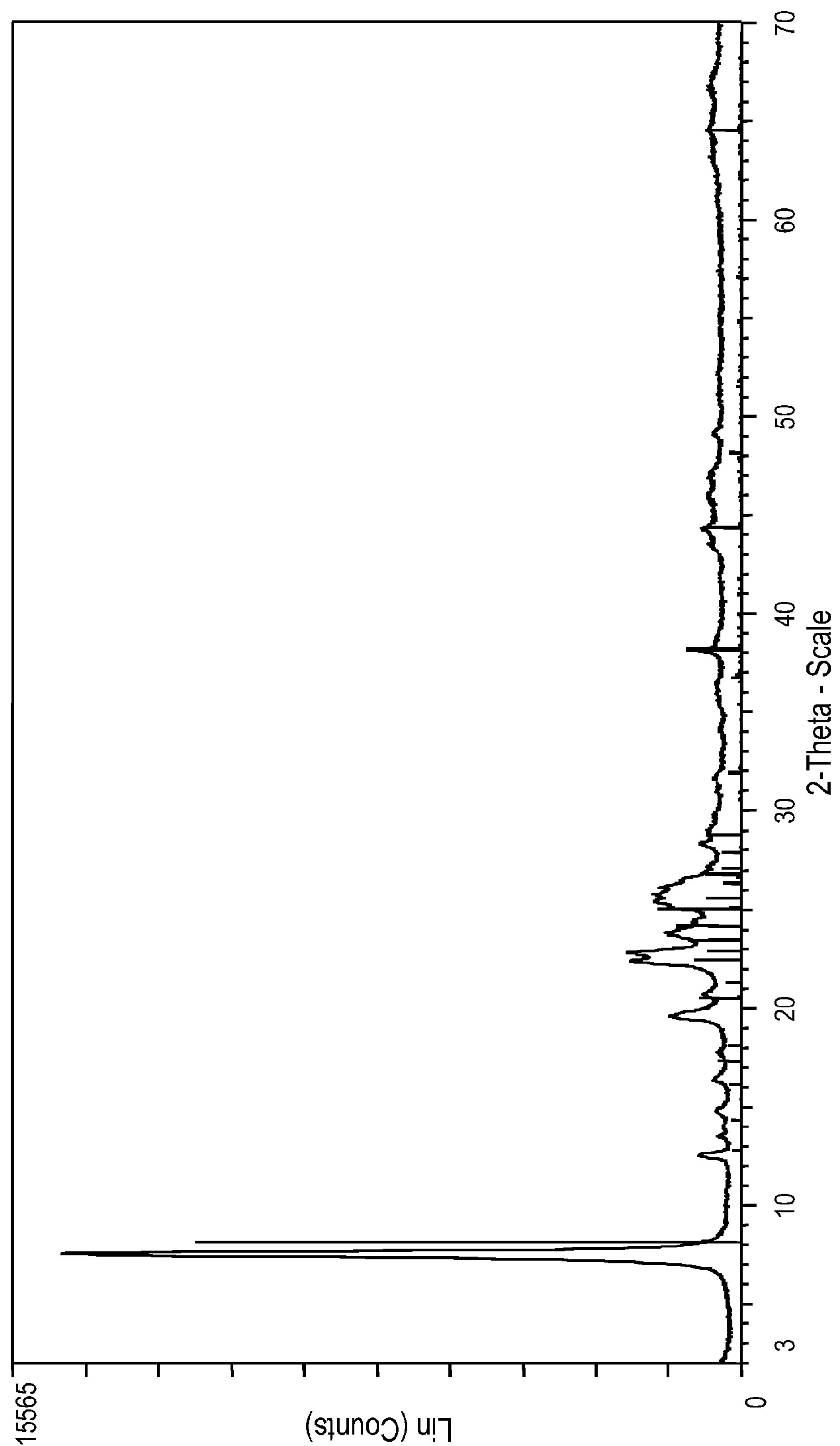
FIG. 18 shows the X-ray diffraction pattern obtained from the pillared silicate compound of Example 18. The figure further includes the line patterns of the RUB-36 structure and of gold, respectively, for comparison.

As may be taken from the X-ray diffraction pattern of the sample of Example 18 displayed in FIG. 18, the highest intensity reflection is shifted towards lower 2 theta values relative to the RUB-36 precursor compound, thus indicating interlayer expansion via bridging of the silicate layers with gold. In particular, the highest intensity reflection is observed at a 2 theta value of 7.53°, indicating a shift of 0.44° 2 theta.

Example 19

Preparation of a Pillared RUB-36 Silicate Using Zinc Chloride

A pillared silicate compound was obtained according to the method described in Example 1, wherein 0.6 g of zinc chloride were used instead of $TiCl_3$, thus affording 2.20 g of a white powder.

Figure 19:
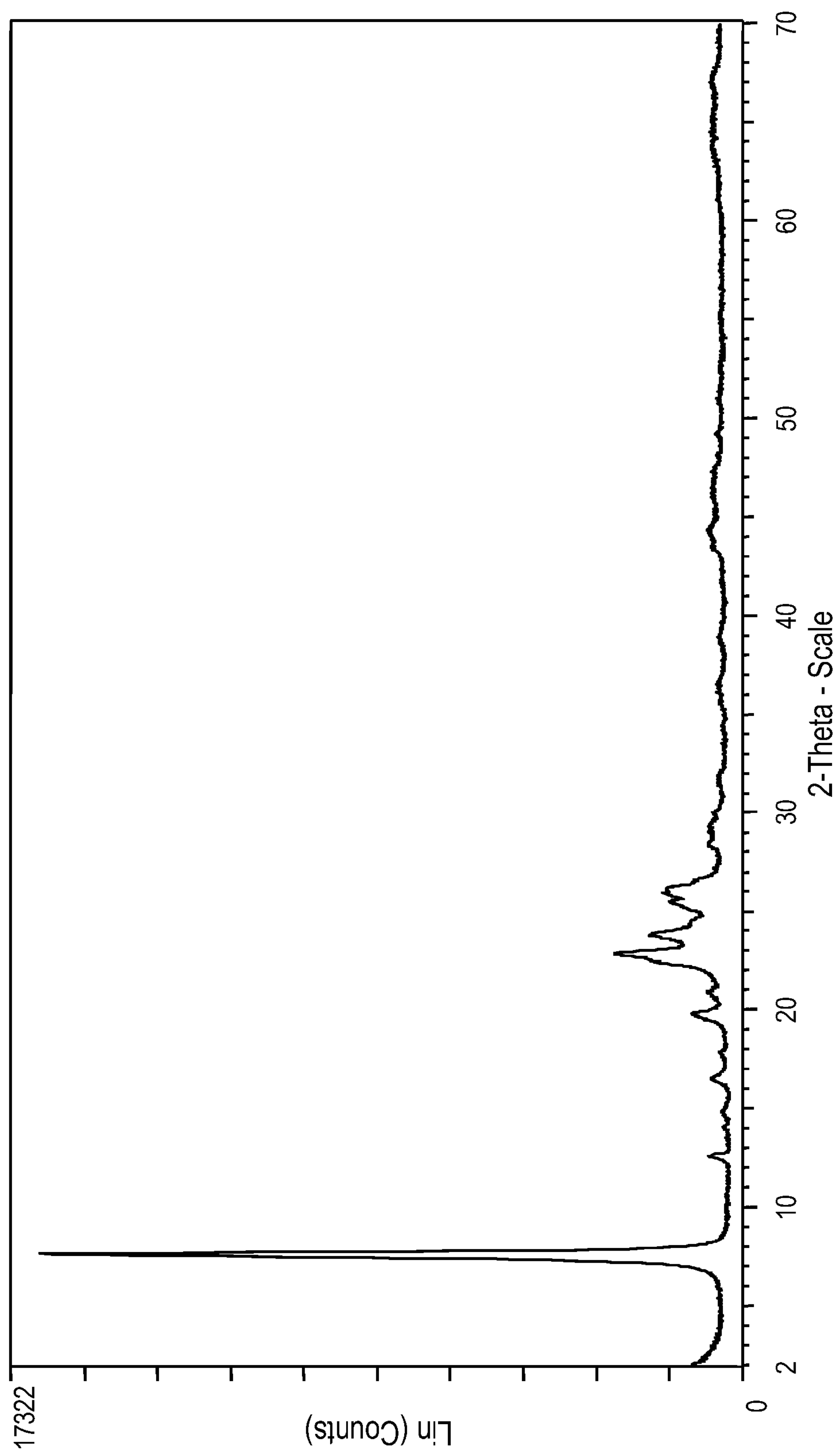
FIG. 19 shows the X-ray diffraction pattern of the pillared silicate compound obtained in Example 19.

As may be taken from the X-ray diffraction pattern of the sample of Example 19 displayed in FIG. 19, the highest intensity reflection is shifted towards lower 2 theta values relative to the RUB-36 precursor compound, thus indicating interlayer expansion of the silicate layers via bridging thereof with zinc. In particular, a value of 7.61° 2 theta is observed for said reflection, indicating a shift of 0.31° 2 theta.

The nitrogen adsorption isotherm obtained for the sample of Example 19 according to DIN 66135 affords a BET surface area of 409 $m^2/g$ and an equivalent surface of 539 $m^2/g$ according to the Langmuir method.

Example 20

Preparation of a Pillared RUB-36 Silicate Using Tin(II) Chloride

A pillared silicate compound was obtained according to the method described in Example 15, wherein 1.0 g of $SnCl_2.2H_2O$ were used instead of CuCl, thus affording 2.30 g of a white powder.

Figure 20:
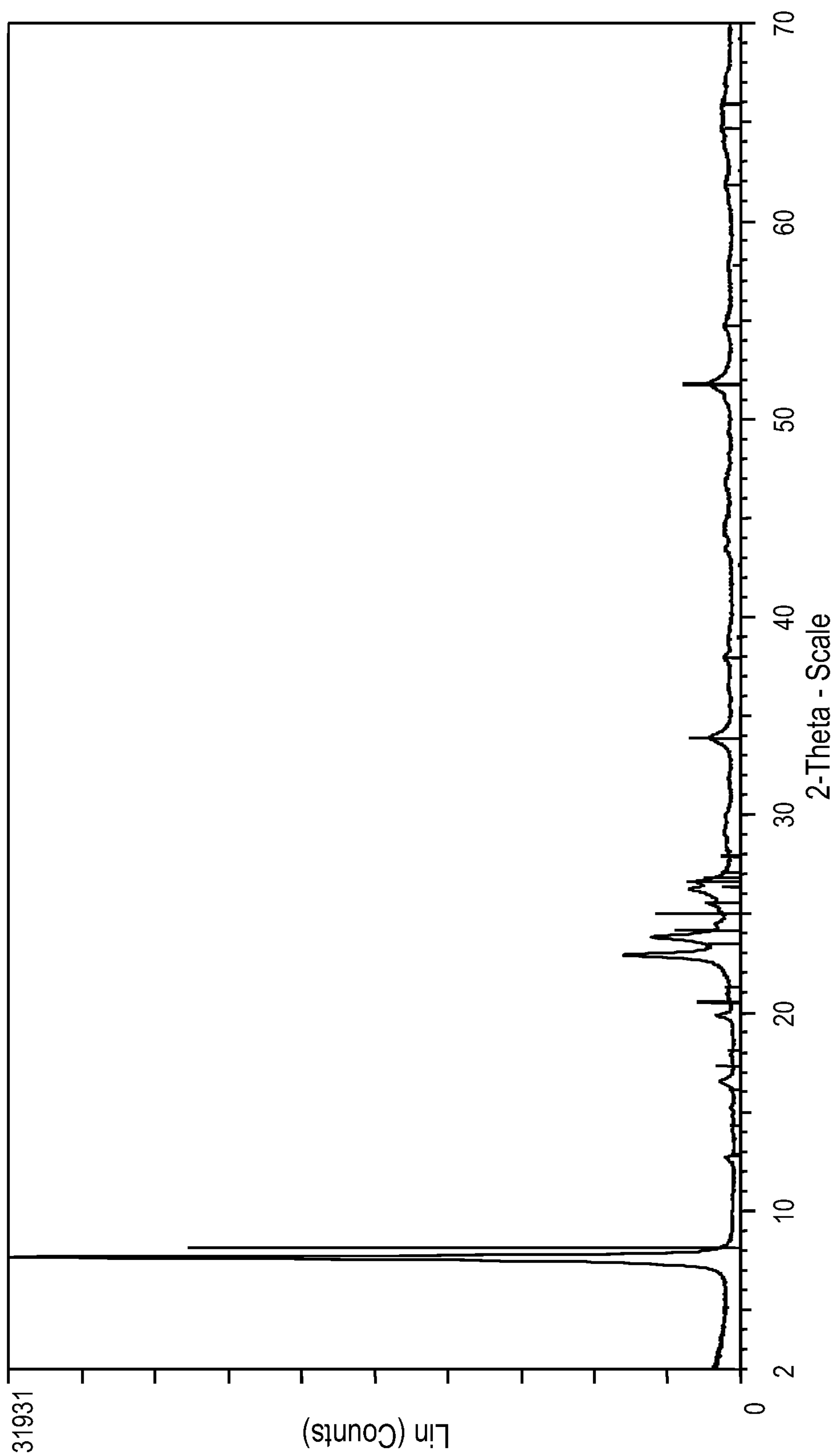
FIG. 20 shows the X-ray diffraction pattern of the pillared silicate compound obtained in Example 20. The figure further includes the line patterns of the RUB-36 structure and of cassiterite ($SnO_2$), respectively, for comparison.

As may be taken from the X-ray diffraction pattern of the sample of Example 20 displayed in FIG. 20, the highest intensity reflection is shifted towards lower 2 theta values relative to the RUB-36 precursor compound, thus indicating interlayer expansion of the silicate layers via bridging thereof with tin. In particular, a value of 7.64° 2 theta is obtained for said reflection, indicating a shift of 0.33° 2 theta relative to RUB-36.

Figure 21:
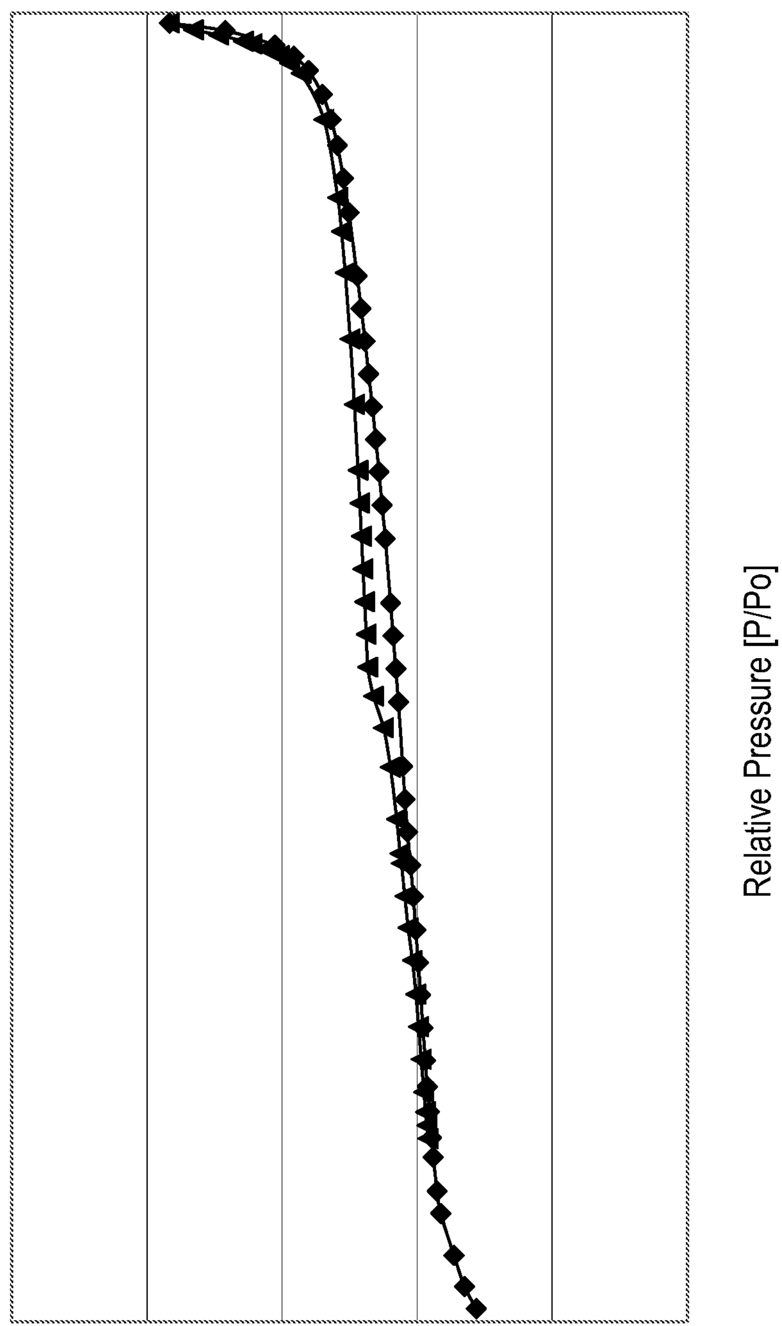
FIG. 21 shows the nitrogen adsorption isotherm obtained for the pillared silicate compound of Example 20.

The nitrogen adsorption isotherm obtained for the sample of Example 20 is displayed in FIG. 21, wherein according to DIN 66135 a BET surface area of 334 $m^2/g$ and an equivalent surface of 440 $m^2/g$ were respectively obtained.

Example 21

Preparation of a Pillared RUB-36 Silicate Using Tin(IV) Chloride

A pillared silicate compound was obtained according to the method of Example 15 using 1.2 g of $SnCl_4$ instead of CuCl, thus affording 2.86 g of a white powder.

Figure 22:
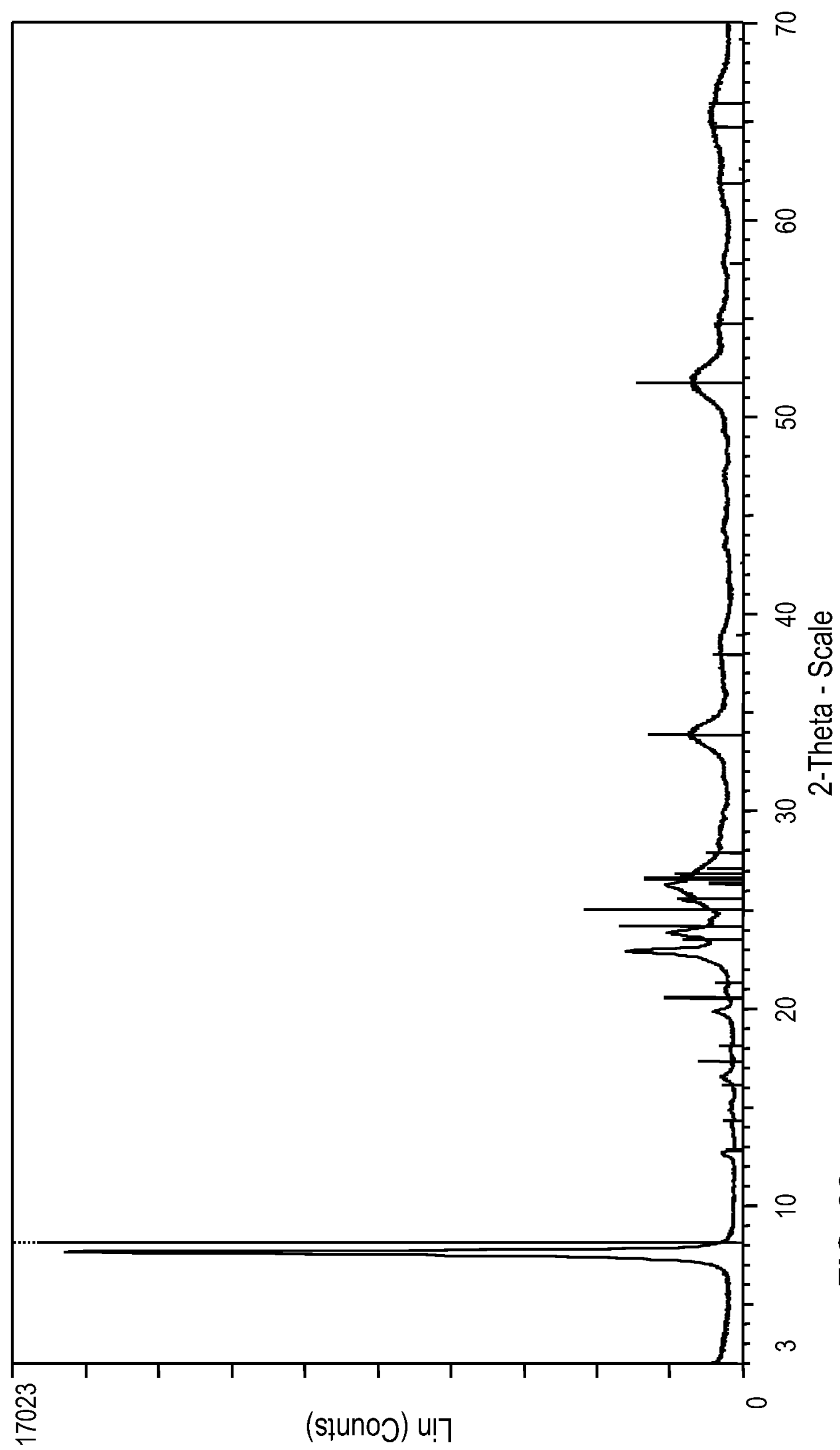
FIG. 22 shows the X-ray diffraction pattern of the pillared silicate compound obtained in Example 21. The figure further includes the line patterns of the RUB-36 structure and of cassiterite ($SnO_2$) for comparison.

As may be taken from the X-ray diffraction pattern of the sample of Example 21 displayed in FIG. 22, the highest intensity reflection is shifted towards lower 2 theta values relative to the RUB-36 precursor compound, thus indicating interlayer expansion of the silicate layers due to bridging thereof via tin. In particular, a value of 7.63° 2 theta is obtained for said reflection, corresponding to a shift of 0.34° 2 theta.

Figure 23:
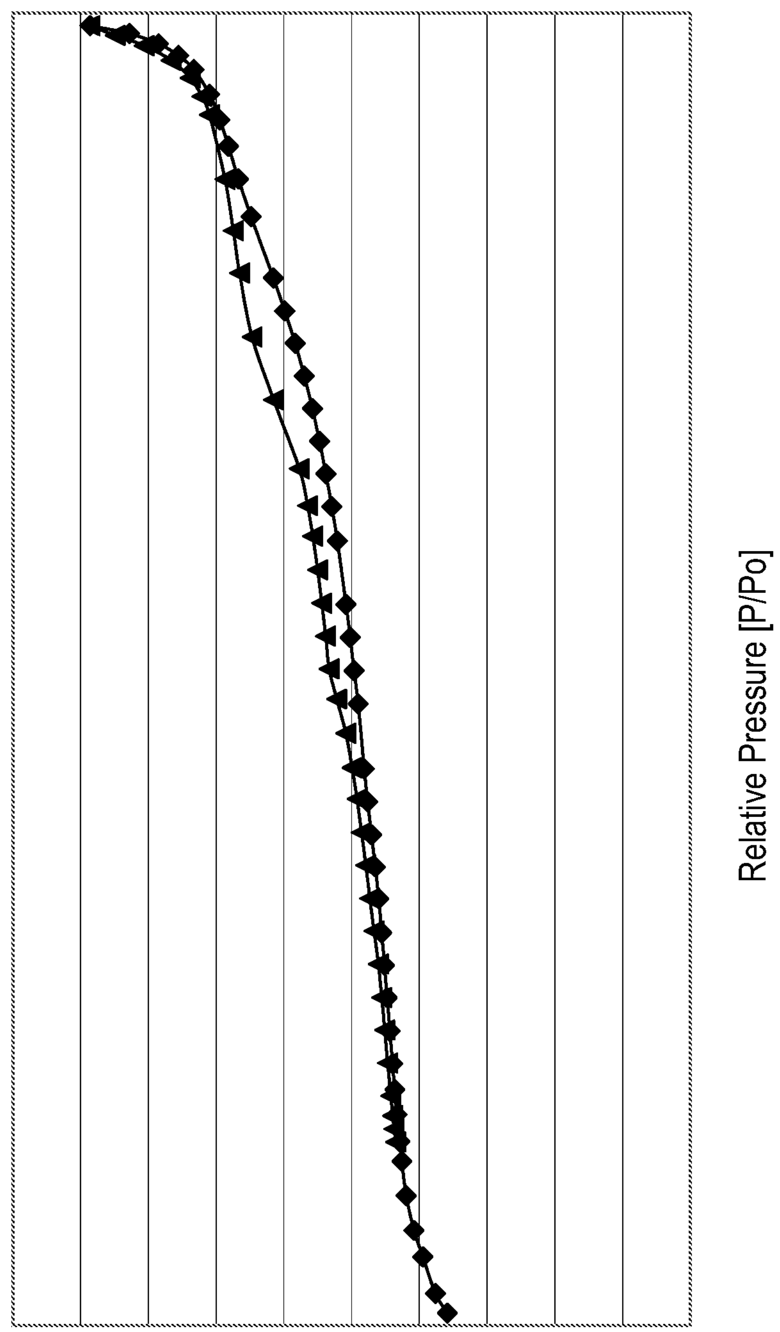
FIG. 23 shows the nitrogen adsorption isotherm of the pillared silicate compound obtained in Example 21.

The nitrogen adsorption isotherm obtained for the sample of Example 21 is displayed in FIG. 23, wherein according to DIN 66135 a BET surface area of 303 $m^2/g$ and an equivalent surface of 398 $m^2/g$ according to the Langmuir method are respectively obtained.

Example 22

Preparation of a Pillared RUB-36 Silicate Using Hexamethyl Ditin 2202.8 g of aqueous diethyldimethylammonium hydroxide (20.62 wt.-%) solution were weighed into a beaker, to which 461.7 g of amorphous silica (Aerosil® 200) were added in portions and the mixture was stirred for 2 h, affording a yellowish suspension. 425.9 g of water were then removed from the resulting mixture using a rotary evaporator, and the concentrated mixture was stirred for 1 h. The mixture was then transferred to a pressure digestion vessel and then heated therein under hydrothermal conditions at 140° C. for 10 days (240 h), thus affording a silvery-white shimmering suspension.

The resulting suspension was then separated by filtration, washed with the mother liquor and subsequently with 10 l of distilled water, after which the solid residue was dried at 120° C. for 24 h, thus affording 378.2 g of RUB-36. The maximum peak (100% intensity) in the X-ray diffraction pattern of the RUB-36 sample was found at 7.96° 2 theta when using the Cu K(alpha 1) wavelength.

A pillared silicate compound was prepared according to the procedure described in Example 1 using RUB-36 obtained according to the present example, wherein 1.5 g of hexamethyl ditin were used instead of $TiCl_3$, thus affording 2.4 g of a white powder.

Figure 24:
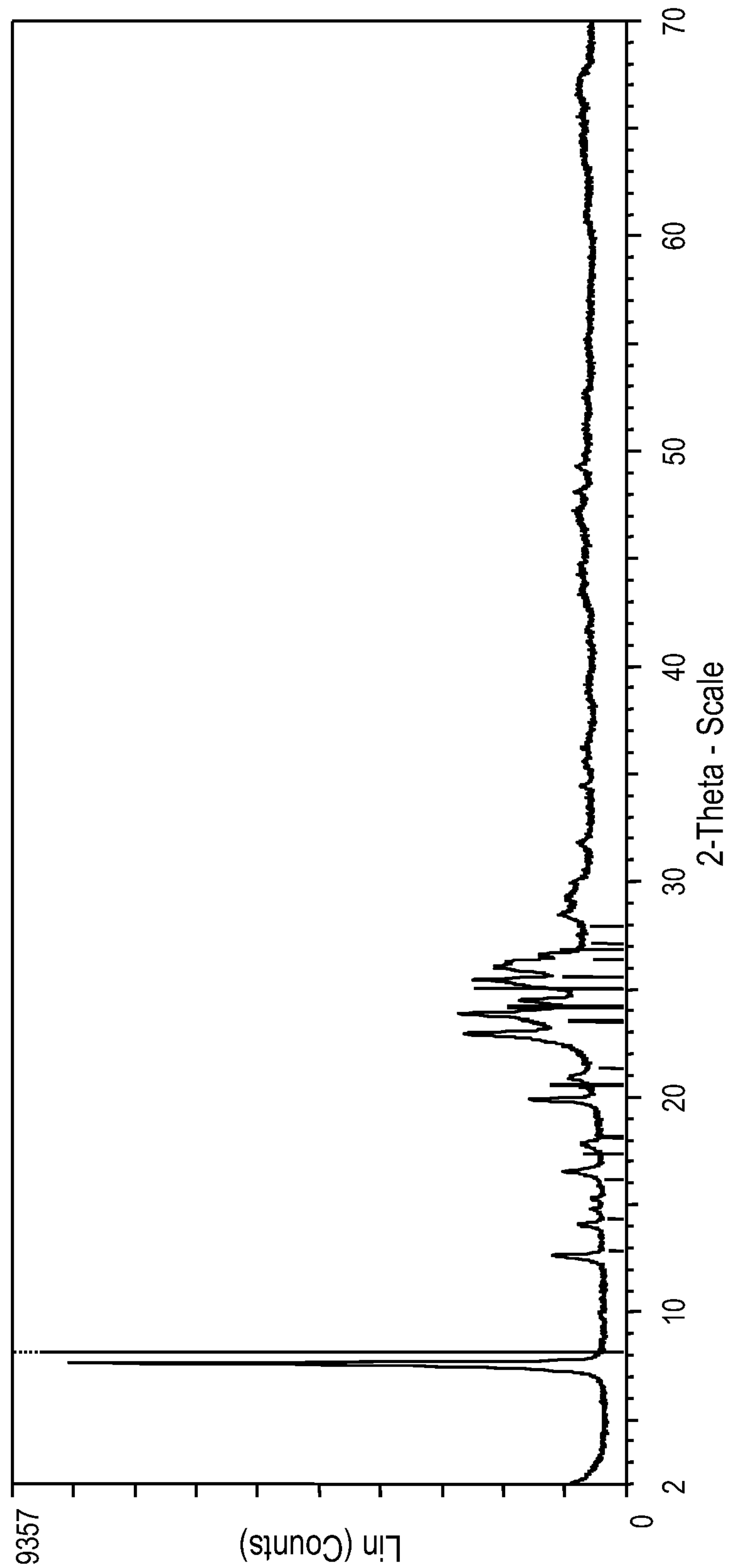
FIG. 24 shows the X-ray diffraction pattern of the pillared silicate compound obtained in Example 22. The figure further includes the line pattern of the RUB-36 structure for comparison.

As may be taken from the sample of Example 22 displayed in FIG. 24, the highest intensity reflection is shifted towards lower 2 theta values relative to the RUB-36 precursor compound, thus indicating interlayer expansion of the silicate layers via bridging with tin. In particular, a 2 theta value of 7.6° is obtained for said reflection, corresponding to a shift of 0.36° 2 theta.

Figure 25:
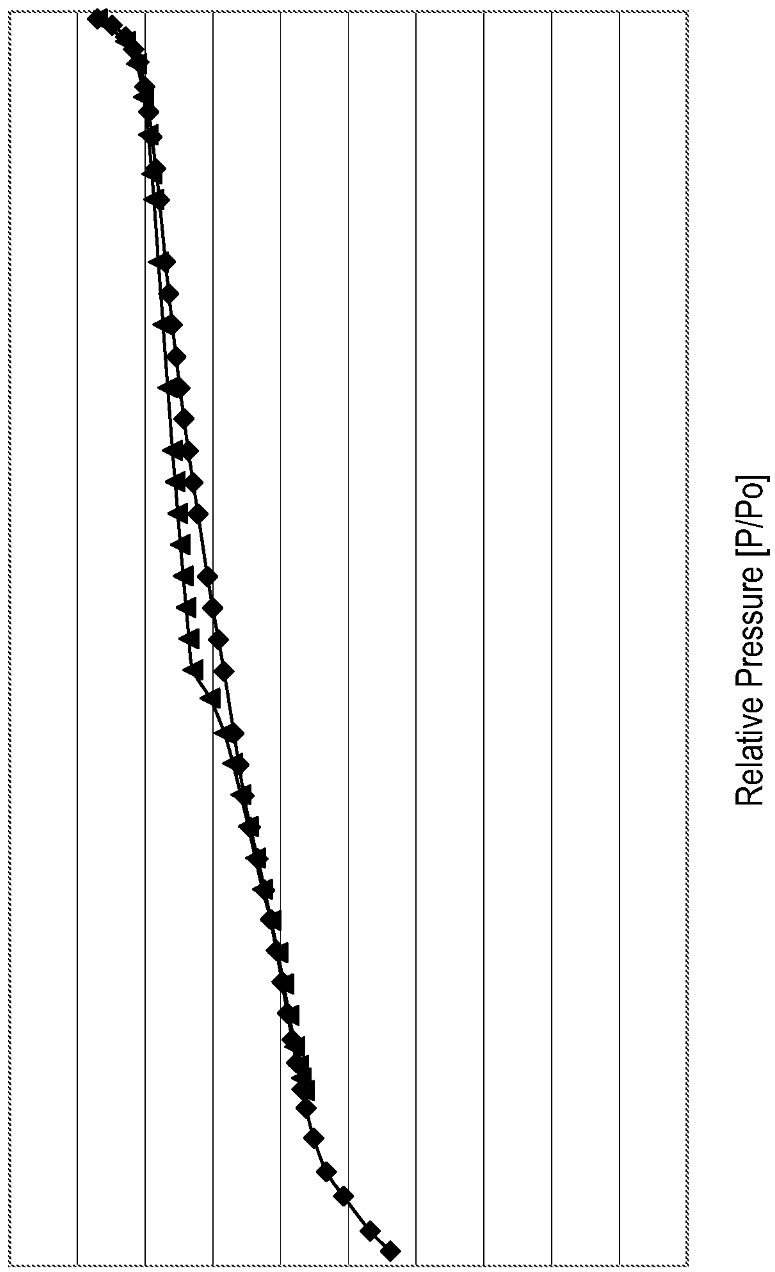
FIG. 25 shows the nitrogen adsorption isotherm of the pillared silicate compound of Example 22.

The nitrogen adsorption isotherm obtained for the sample of Example 22 is displayed in FIG. 25, wherein according to DIN 66135 a BET surface area of 410 $m^2/g$ and an equivalent surface of 546 $m^2/g$ according to the Langmuir method are respectively obtained.

Example 23

Preparation of a Pillared RUB-36 Silicate Using Dimethyl Tin Dichloride

A pillared silicate compound was obtained according to the method described in Example 22, wherein 1.0 g of dimethyl tin dichloride was used instead of hexamethyl ditin, thus affording 1.2 g of a white powder.

Figure 26:
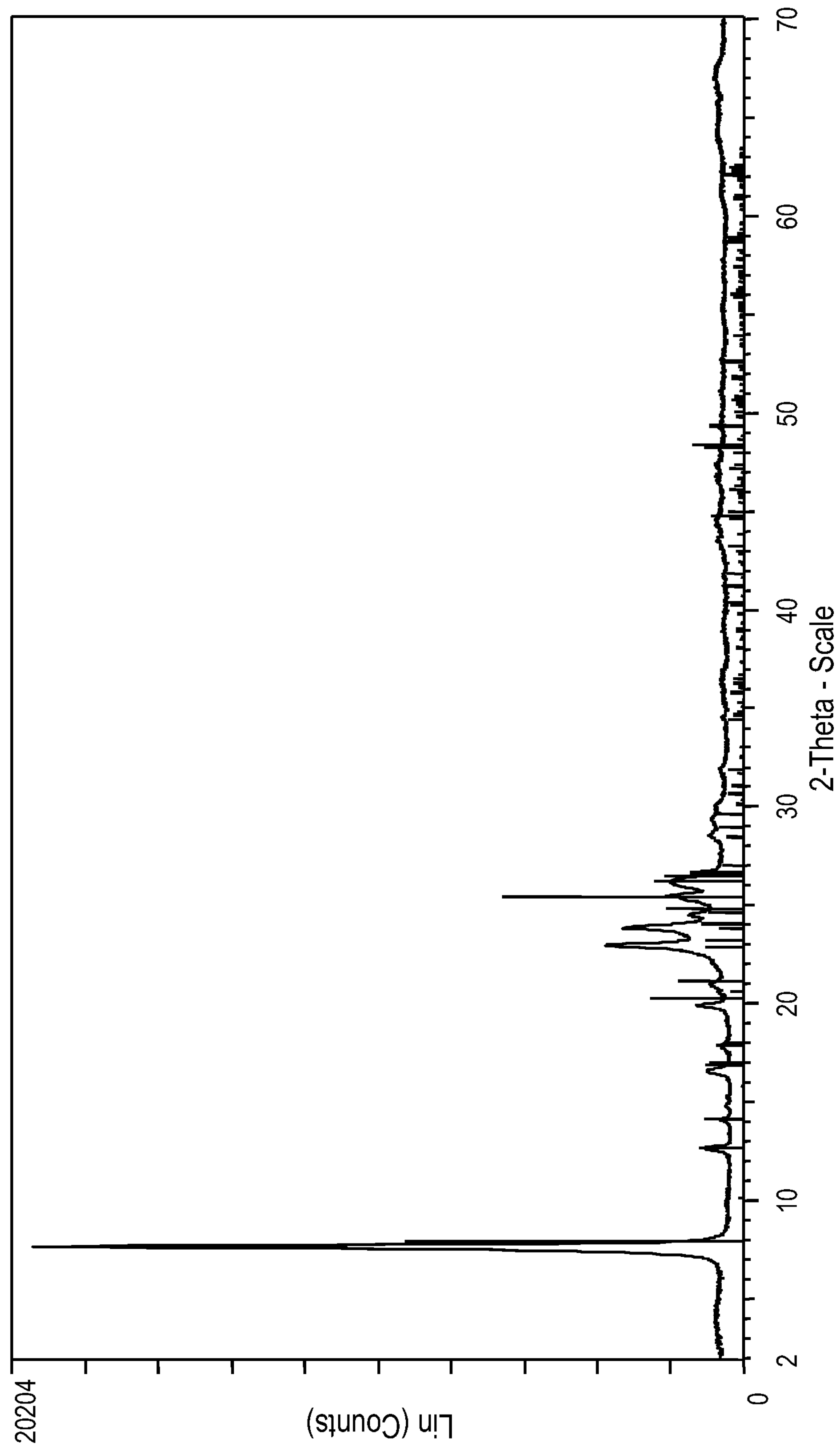
FIG. 26 shows the X-ray diffraction pattern of the pillared silicate compound obtained according to Example 23. The figure further includes the pattern of the RUB-36 structure for comparison.

As may be taken from the X-ray diffraction pattern of the sample of Example 23 displayed in FIG. 26, the highest intensity reflection is shifted towards lower 2 theta values relative to the RUB-36 precursor compound. In particular, a value of 7.62° 2 theta is obtained for said reflection, corresponding to a shift of 0.32° 2 theta.

The nitrogen adsorption isotherm obtained using the sample of Example 23 according to DIN 66135 afforded a BET surface area of 414 $m^2/g$ and an equivalent surface of 549 $m^2/g$ according to the Langmuir method.

Comparative Example 2

The procedure of Example 23 was repeated, wherein a temperature of 80° C. was chosen for the hydrothermal reaction which was conducted for a period of 72 h, thus affording 1.1 g of a white powder.

Figure 27:
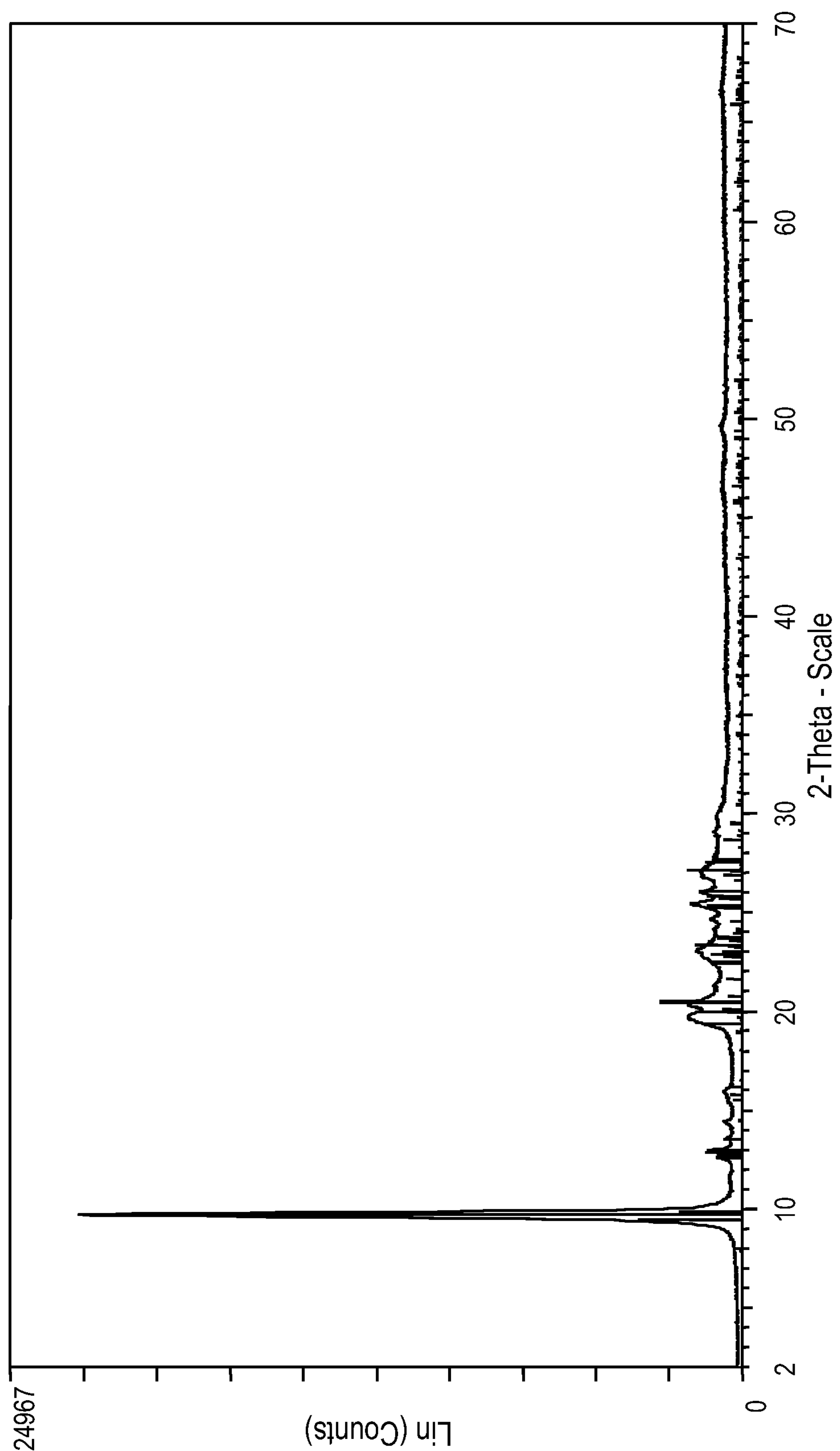
FIG. 27 shows the X-ray diffraction pattern of the compound obtained in Comparative Example 2. The figure further includes the line patterns of the RUB-37 structure and of orthorhombic $SiO_2$ for comparison.

As may be taken from the X-ray diffraction pattern of the sample of Comparative Example 2 in FIG. 27, the highest intensity reflection is shifted towards higher 2 theta values, thus indicating a decrease in interlayer spacing typical of topotactic condensation of the silicate layers of RUB-36 achieved during calcination thereof. In particular, the highest intensity reflection coincides with the corresponding reflection in RUB-37, which is the topotactic condensation product of RUB-36. Consequently, as opposed to Example 23, the procedure of Comparative Example 2 does not afford a pillared silicate compound.

Figure 28:
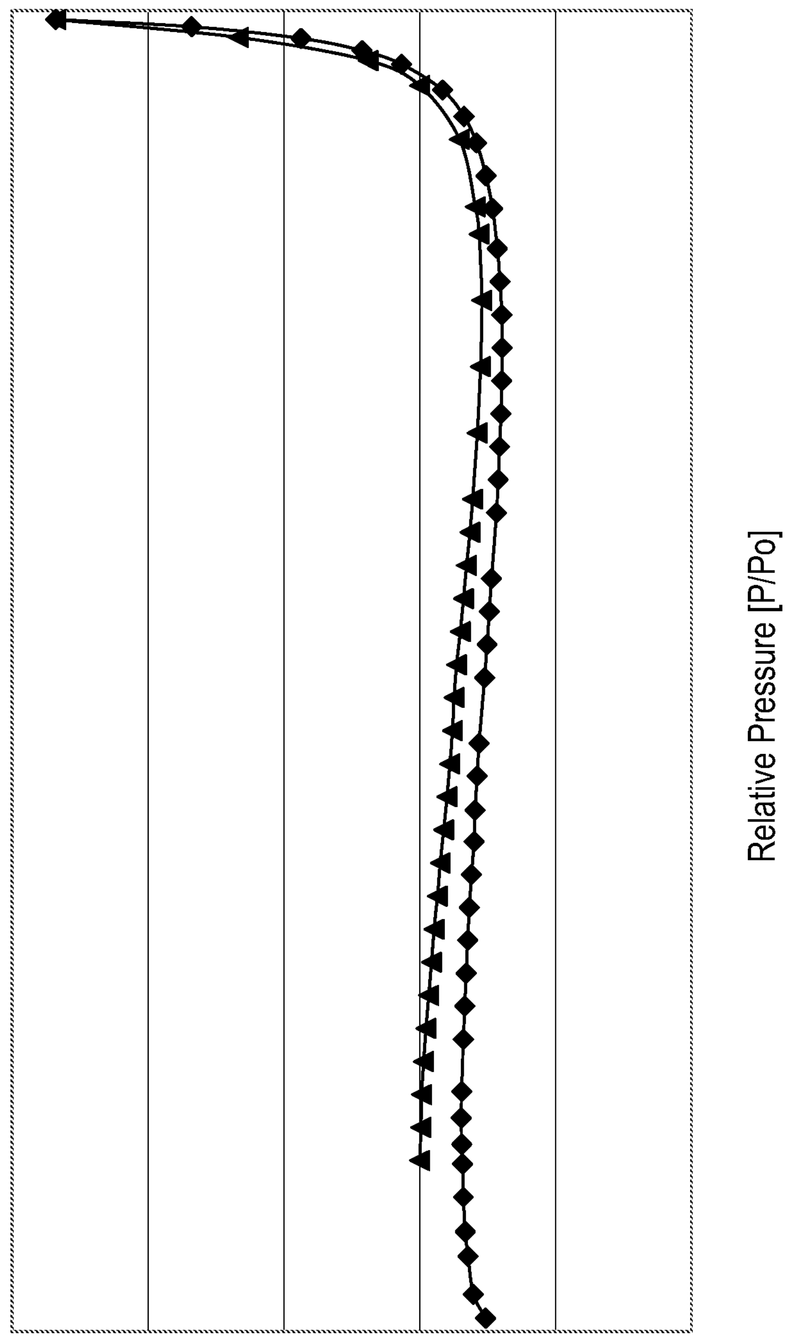
FIG. 28 shows the nitrogen adsorption isotherm obtained for the silicate compound of Comparative Example 2.

This is confirmed by the nitrogen adsorption isotherm obtained for the sample of Comparative Example 2 displayed in FIG. 28, wherein according to DIN 66135 a BET surface area of merely 28 $m^2/g$ and an equivalent surface of 37 $m^2/g$ according to the Langmuir method are respectively obtained.

Example 24

Preparation of a Pillared RUB-36 Silicate Using Samarium(III) Chloride

A pillared silicate compound was obtained according to the procedure described in Example 6 using 1.7 g of $SmCl_3.H_2O$ instead of $MnCl_2$, thus affording 2.04 g of a white powder.

Figure 29:
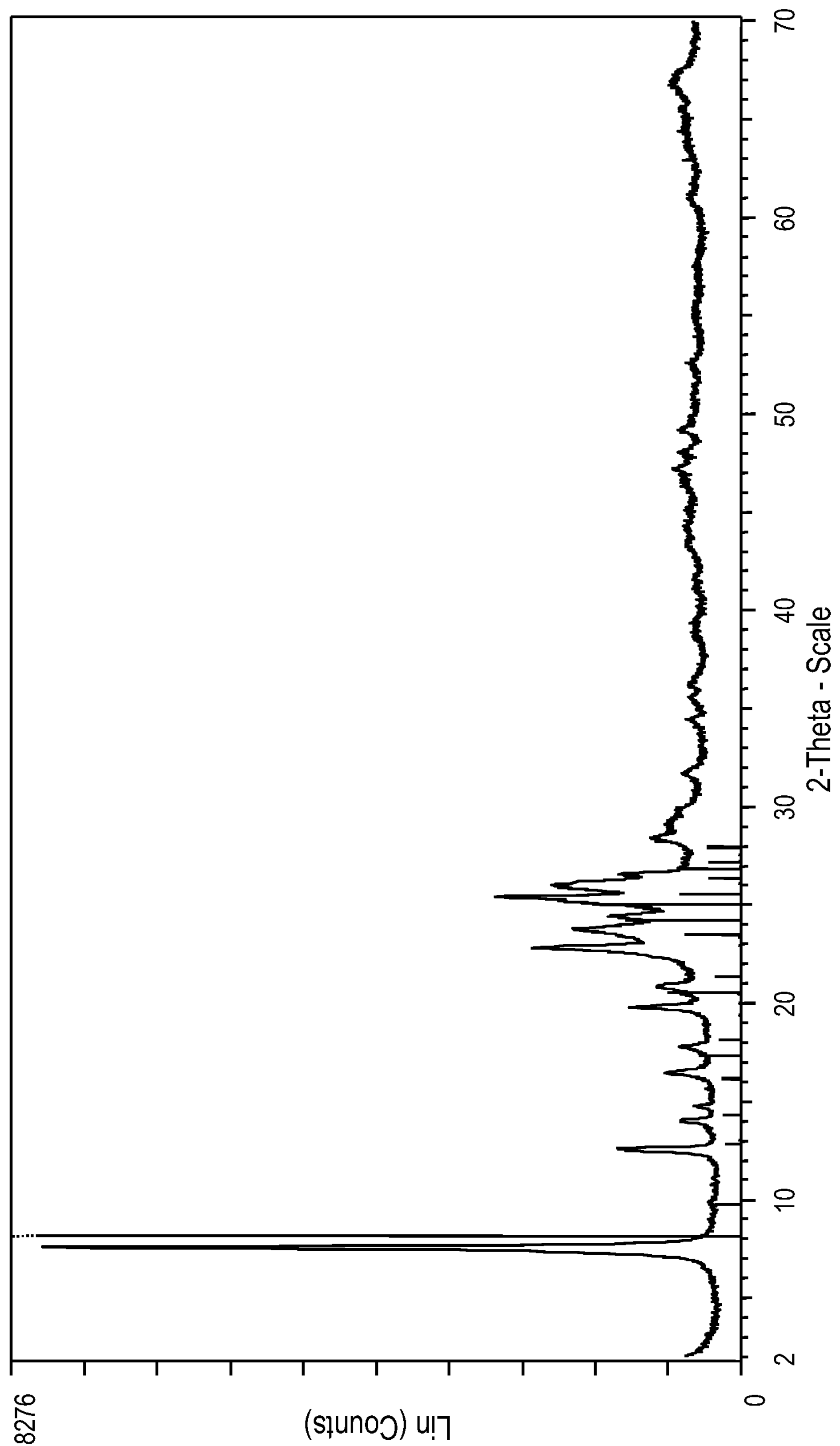
FIG. 29 shows the X-ray diffraction pattern of the pillared silicate compound obtained according to Example 24. The figure further contains the line patterns of the RUB-36 and RUB-37 structures for comparison.

As may be taken from the X-ray diffraction pattern of the sample of Example 24 displayed in FIG. 29, the highest intensity reflection is shifted towards lower 2 theta values, thus indicating interlayer expansion of the silicate layers via bridging thereof with samarium. In particular, said reflection is observed at a 2 theta value of 7.55°, corresponding to a shift of 0.37° 2 theta relative to the RUB-36 precursor compound.

Figure 30:
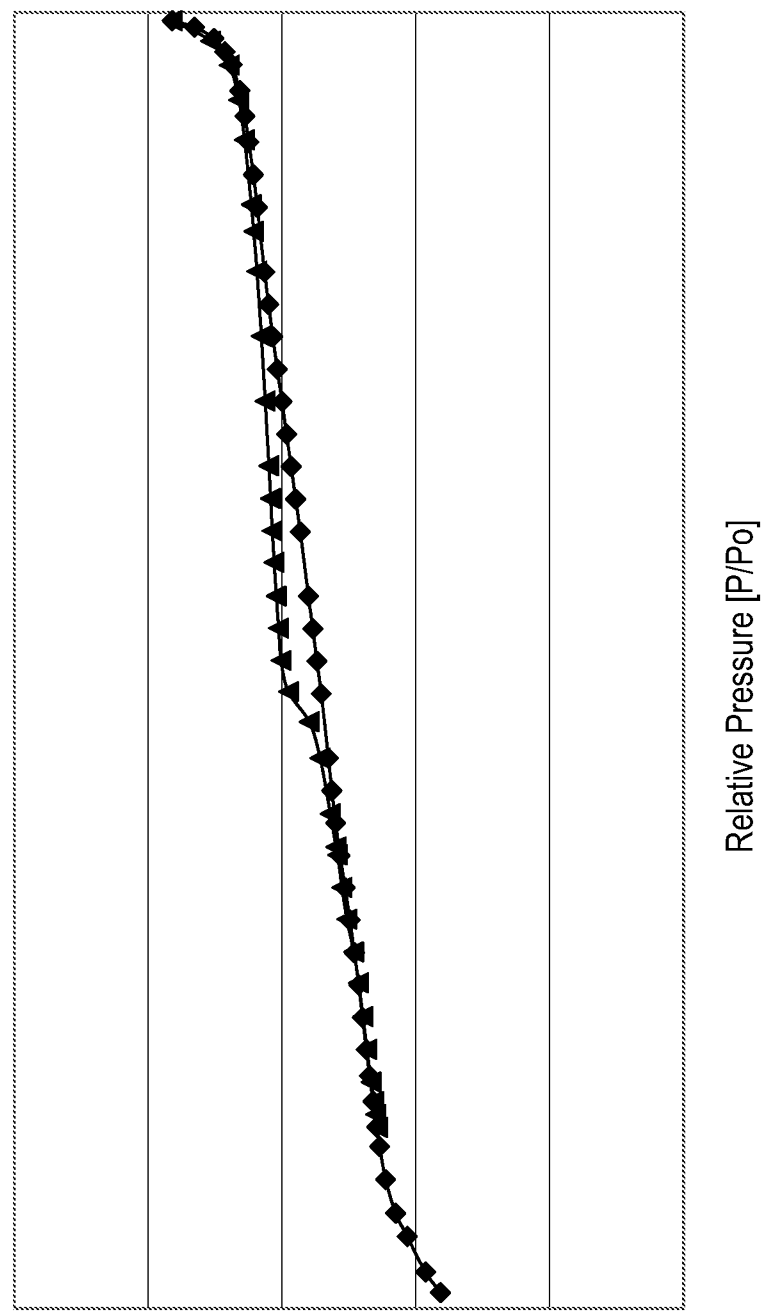
FIG. 30 shows the nitrogen adsorption isotherm of the pillared silicate compound of Example 24.

The nitrogen adsorption isotherm obtained from the sample of Example 24 is displayed in FIG. 30, wherein according to DIN 66135 a BET surface area of 411 $m^2/g$ and an equivalent surface of 546 $m^2/g$ according to the Langmuir method are respectively obtained.

The invention claimed is:

1. A pillared silicate compound comprising a layered silicate structure, and bridging metal atoms located between adjacent silicate layers of the silicate structure, wherein said bridging metal atoms form at least one covalent bond to each of the adjacent silicate layers.

2. The pillared silicate compound of claim 1, wherein the layered silicate structure comprises silicate layers selected from the group consisting of zeolite-type layers.

3. The pillared silicate compound of claim 1, wherein the layered silicate structure originates from one or more layered silicate compounds and/or is derived from one or more layered silicate compounds, said one or more layered silicate compounds comprising one or more layered silicates selected from the group consisting of MCM-22, PREFER, Nu-6(2), CDS-1, PLS-1, MCM-47, ERS-12, MCM-65, RUB-15, RUB-18, RUB-20, RUB-36, RUB-38, RUB-39, RUB-40, RUB-42, RUB-51, BLS-1, BLS-3, ZSM-52, ZSM-55, kanemite, makatite, magadiite, kenyaite, revdite, montmorillonite, and combinations of two or more thereof.

4. The pillared silicate compound of claim 1, wherein the silicate layers of the layered silicate structure are isomorphously substituted.

5. The pillared silicate compound of claim 1, wherein the bridging metal atoms comprise one or more metals selected from the group consisting of Li, Be, B, Mg, Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd, Hg, Al, Ga, In, Tl, Ge, Sn, Pb, Bi, Ce, Pr, Nd, Pm, Sm, Eu, Gd, Tb, Dy, Ho, Er, Tm, Yb, Lu, Ac, Th, Pa, U, Np, Pu, and combinations of two or more thereof.

6. The pillared silicate compound of claim 1, wherein the bridging metal atoms do not comprise one or more elements selected from the group consisting of Al, B, and Ti.

7. The pillared silicate compound of claim 3, wherein when using the Cu K(alpha 1) wavelength in the diffraction experiment, the 2 theta diffraction angle for the maximum peak (100% intensity) in the X-ray diffraction pattern of the pillared silicate compound is from 0.05 to 1.45° 2 theta lower than the 2 theta diffraction angle of the corresponding maximum peak (100% intensity) in the X-ray diffraction pattern of the layered silicate compound.

8. The pillared silicate compound of claim 1, having an X-ray diffraction pattern of which the maximum peak (100% intensity) is located at a 2 theta diffraction angle in the range of from 3 to 14° 2 theta when using the Cu K(alpha 1) wavelength in the diffraction experiment.

9. The pillared silicate compound of claim 1, having a BET surface area determined according to DIN 66135 in the range of from 50 to 950 $m^2/g$.

10. A process for the preparation of a pillared silicate compound according to claim 1, comprising the steps of:

(1) providing an acidic mixture comprising one or more layered silicate compounds, one or more metal compounds, and one or more solvents; and (2) reacting the mixture obtained in step (1) to obtain at least one pillared silicate compound, wherein the reacting of the mixture in step (2) comprises heating said mixture under autogenous pressure.

11. The process of claim 10, wherein the heating in step (2) is carried out at a temperature in the range of from 50 to 250° C.

12. The process of claim 10, wherein the one or more solvents comprised in the acidic mixture comprise water.

13. The process of claim 10, wherein one or more acids are further provided in step (1).

14. The process of claim 10, wherein the one or more metal compounds comprise one or more Lewis acids, the Lewis acidity being in particular with respect to the one or more solvents.

15. The process of claim 10, wherein the pH of the mixture provided in step (1) is in the range of from –0.5 to 5.

16. The process of claim 10, wherein the one or more layered silicate compounds comprise one or more layered silicates selected from the group consisting of MCM-22, PREFER, Nu-6(2), CDS-1, PLS-1, MCM-47, ERS-12, MCM-65, RUB-15, RUB-18, RUB-20, RUB-36, RUB-38, RUB-39, RUB-40, RUB-42, RUB-51, BLS-1, BLS-3, ZSM- 52, ZSM-55, kanemite, makatite, magadiite, kenyaite, revdite, montmorillonite, and combinations of two or more thereof.

17. The process of claim 10, wherein one or more of the one or more layered silicate compounds are isomorphously substituted.

18. The process of claim 10, wherein the one or more metal compounds comprise one or more metals selected from the group consisting of Li, Be, B, Mg, Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn Cd, Hg, Al, Ga, In, Tl, Ge, Sn, Pb, Bi, Ce, Pr, Nd, Pm, Sm, Eu, Gd, Tb, Dy, Ho, Er, Tm, Yb, Lu, Ac, Th, Pa, U, Np, Pu, and combinations of two or more thereof.

19. The process of claim 10, wherein the one or more metal compounds comprise one or more metal compounds selected from the group consisting of metal salts, metal complexes, organometallic compounds, and combinations of two or more thereof.

20. The process of claim 19, wherein the group of metal salts comprises one or more compounds selected from the group consisting of metal halides, metal hydroxides, metal carbonates, metal carboxylates, metal nitrates, metal nitrites, metal phosphates, metal phosphites, metal phosphonates, metal phosphinates, metal sulfates, metal sulfites, metal sulfonates, metal alkoxides, metal complexes, and combinations and/or mixtures of two or more thereof.

21. The process of claim 19, wherein the group of organometallic compounds comprises one or more organometallic compounds selected from the group consisting of organoaluminum compounds, organotitanium compounds, organomanganese compounds, organoiron compounds, organocobalt compounds, organocopper compounds, organozinc compounds, organopalladium compounds, organosilver compounds, organotin compounds, organoplatinum compounds, organogold compounds, and mixtures thereof.

22. The process of claim 10, wherein the mixture is reacted in step (2) for a period of from 1 to 72 h.

23. The process of claim 10, which further comprises the steps of:

(3) separating the pillared silicate from the mixture obtained according to step (2); and (4) washing and/or drying the pillared silicate obtained from step (3).

24. The process of claim 23, which further comprises the step of (5) calcining the pillared silicate obtained in step (2) and/or (3) and/or (4).

25. A pillared silicate compound obtained by a process according to claim 10.

26. The pillared silicate compound of claim 25, having an X-ray diffraction pattern of which the maximum peak (100% intensity) is located at a 2 theta diffraction angle in the range of from 3 to 14° 2 theta when using the Cu K(alpha 1) wavelength in the diffraction experiment.

27. The pillared silicate compound of claim 25, having a BET surface area determined according to DIN 66135 in the range of from 50 to 950 $m^2/g$.

28. The pillared silicate of claim 1, comprised in a molding.

29. A method comprising a step of contacting one or more chemical compounds with the pillared silicate compound according to claim 1 for catalyzing a chemical reaction, separating the one or more chemical compounds, absorbing one or more of the chemical compounds, ion-exchanging one or more of the chemical compounds, producing a ceramic, and/or for producing a polymer.

* * * * *

UNITED STATES PATENT AND TRADEMARK OFFICE

CERTIFICATE OF CORRECTION

PATENT NO. : 8,426,332 B2
APPLICATION NO. : 13/175125
DATED : April 23, 2013
INVENTOR(S) : Ulrich Müller et al.

It is certified that error appears in the above-identified patent and that said Letters Patent is hereby corrected as shown below:

On the title page, item (73), the Assignee "Tokyo Institute of Technology, Tokyo, Japan", should be added as the second assignee.

Signed and Sealed this
Twenty-first Day of January, 2014

Michelle K. Lee
*Deputy Director of the United States Patent and Trademark Office*